US008871478B2

(12) United States Patent
Yukawa et al.

(10) Patent No.: US 8,871,478 B2
(45) Date of Patent: Oct. 28, 2014

(54) CORYNEFORM BACTERIUM TRANSFORMANT AND PROCESS FOR PRODUCING ISOBUTANOL USING THE SAME

(75) Inventors: Hideaki Yukawa, Kyoto (JP); Masayuki Inui, Kyoto (JP)

(73) Assignee: Research Institute of Innovative Technology for the Earth, Kyoto (JP)

( * ) Notice: Subject to any disclaimer, the term of this patent is extended or adjusted under 35 U.S.C. 154(b) by 166 days.

(21) Appl. No.: 13/258,670

(22) PCT Filed: Mar. 29, 2010

(86) PCT No.: PCT/JP2010/055504
§ 371 (c)(1),
(2), (4) Date: Nov. 2, 2011

(87) PCT Pub. No.: WO2010/113832
PCT Pub. Date: Oct. 7, 2010

(65) Prior Publication Data
US 2012/0115196 A1  May 10, 2012

(30) Foreign Application Priority Data

Mar. 30, 2009 (JP) .................................. 2009-083668

(51) Int. Cl.
| | | |
|---|---|---|
| C12N 1/21 | (2006.01) | |
| C12P 7/16 | (2006.01) | |
| C12N 9/04 | (2006.01) | |
| C12N 9/88 | (2006.01) | |
| C12N 9/00 | (2006.01) | |
| C12N 15/00 | (2006.01) | |
| C12P 21/00 | (2006.01) | |

(52) U.S. Cl.
CPC .................. *C12P 7/16* (2013.01); *C12N 9/0006* (2013.01); *Y02E 50/10* (2013.01); *C12N 9/88* (2013.01)
USPC ................... 435/160; 435/252.32; 435/320.1; 435/69.1; 435/183

(58) Field of Classification Search
USPC ......... 435/160, 252.32, 440, 320.1, 69.1, 183
See application file for complete search history.

(56) References Cited

U.S. PATENT DOCUMENTS

| | | | | |
|---|---|---|---|---|
| 3,003,925 | A * | 10/1961 | Kinoshita et al. ............. | 435/110 |
| 3,136,702 | A * | 6/1964 | Okumura et al. ............. | 435/111 |
| 8,003,365 | B2 * | 8/2011 | Yoshikuni et al. ......... | 435/252.1 |
| 2007/0092957 | A1 | 4/2007 | Donaldson et al. | |
| 2008/0009046 | A1 * | 1/2008 | Sturmer et al. ............... | 435/160 |
| 2008/0274526 | A1 | 11/2008 | Bramucci et al. | |
| 2009/0081746 | A1 | 3/2009 | Liao et al. | |
| 2009/0111154 | A1 | 4/2009 | Liao et al. | |

FOREIGN PATENT DOCUMENTS

| | | |
|---|---|---|
| JP | 2009-039031 | 2/2009 |
| WO | 2007/050671 | 5/2007 |
| WO | 2008/098227 | 8/2008 |

OTHER PUBLICATIONS

Inui et al., Journal of Molecular Microbiology and Biotechnology 8:243-254, 2004.*
Blombach et al., Applied and Environmental Microbiology 73(7):2079-2084, 2007.*
Yukawa et al., Microbiology 153:1042-1058, 2007.*
Keilhauer et al., GenBank accession No. L09232, 1995.*
Inui et al., GenBank accession No. E08232, 2005.*
Kalinowski et al., GenBank accession No. BX927151, 2006.*
International Search Report issued Apr. 20, 2010 in International (PCT) Application No. PCT/JP2010/055504.
S. Atsumi et al., "Non-Fermentative Pathways for Synthesis of Branched-Chain Higher Alcohols as Biofuels", Nature, vol. 451, pp. 86-89, Jan. 3, 2008.
H. Yoshimoto et al., "Genetic and Physiological Analysis of Branched-Chain Alcohols and Isoamyl Acetate Production in *Saccharomyces cerevisiae*", Applied Microbiology and Biotechnology, vol. 59, Nos. 4-5, pp. 501-508, Jan. 1, 2002.
S. Atsumi et al., "Acetolactate Synthase from *Bacillus subtilis* Serves as a 2-Ketoisovalerate Decarboxylase for Isobutanol Biosynthesis in *Escherichia coli*", Applied and Environmental Microbiology, vol. 75, No. 19, pp. 6306-6311, Oct. 2009.
S. Atsumi et al., "Direct Photosynthetic Recycling of Carbon Dioxide to Isobutyraldehyde", Nature Biotechnology, vol. 27, No. 12, pp. 1177-1180, Dec. 2009.
Extended European Search Report issued Aug. 3, 2012 in corresponding European Application No. 10758603.4.
Blombach, Bastian, et al., "*Corynebacterium glutamicum* Tailored for Efficient Isobutanol Production", Applied and Environmental Microbiology, vol. 77, No. 10, May 2011, pp. 3300-3310.
Smith, Kevin Michael, et al., "Engineering *Corynebacterium glutamicum* for isobutanol production", Applied Microbiology and Biotechnology, vol. 87, No. 3, Apr. 2010, pp. 1045-1055.

* cited by examiner

*Primary Examiner* — Delia Ramirez
(74) *Attorney, Agent, or Firm* — Wenderoth, Lind & Ponack, L.L.P.

(57) ABSTRACT

A *Corynebacterium glutamicum* transformant having the capability of producing isobutanol and the following genes (1) to (5):
(1) a gene which encodes an enzyme having acetohydroxy acid synthase activity;
(2) a gene which encodes an enzyme having acetohydroxy acid isomeroreductase activity;
(3) a gene which encodes an enzyme having dihydroxy acid dehydratase activity;
(4) a gene which encodes an enzyme having 2-keto acid decarboxylase activity; and
(5) a gene which encodes an enzyme having alcohol dehydrogenase activity,
at least one of the genes being endogenous, and at least one of the genes being exogenous, efficiently produces isobutanol.

4 Claims, 3 Drawing Sheets

SEQUENCE LISTING

```
<160> NUMBER OF SEQ ID NOS: 78

<210> SEQ ID NO 1
<211> LENGTH: 1195
<212> TYPE: DNA
<213> ORGANISM: Corynebacterium casei

<400> SEQUENCE: 1
atgaaaaccg accgtgcacg ctcgtgtgag aaagtcagct acatgagacc aactacccgc      60
cctgagggac gctttgagca gctgtggctg ccgctgtggc cattggcaag cgatgacctc     120
cgtgagggca tttaccgcac ctcacggaag aacgcgctgg ataagcgcta cgtcgaagcc     180
aatcccgacg cgctctctaa cctcctggtc gttgacatcg accaggagga cgcgcttttg     240
cgctctttgt gggacaggga ggactggaga cctaacgcgg tggttgaaaa ccccttaaac     300
gggcacgcac acgctgtctg ggcgctcgcg gagccattta cccgcaccga atacgccaaa     360
cgcaagcctt tggcctatgc cgcggctgtc accgaaggcc tacggcgctc tgtcgatggc     420
gatagcggat actccgggct gatcaccaaa aaccccgagc acactgcatg ggatagtcac     480
tggatcaccg ataagctgta tacgctcgat gagctgcgct tttggctcga agaaaccggc     540
tttatgccgc ctgcgtcctg gaggaaaacg cggcggttct cgccagttgg tctaggtcgt     600
aattgcgcac tctttgaaag cgcacgtacg tgggcatatc gggaggtcag aaagcatttt     660
ggagacgctg acggcctagg ccgcgcaatc caaaccaccg cgcaagcact taaccaagag     720
ctgtttgatg aaccactacc tgtggccgaa gttgactgta ttgccaggtc aatccataaa     780
tggatcatca ccaagtcacg catgtggaca gacggcgccg ccgtctacga cgccacattc     840
accgcaatgc aatccgcacg cgggaagaaa ggctggcaac gaagcgctga ggtgcgtcgt     900
gaggctggac atactctttg gaggaacatt ggctaaggtt tatgcacgtt atccacgcaa     960
cggaaaaaca gcccgcgagc tggcagaacg tgccggtatg tcggtgagaa cagctcaacg    1020
atggacttcc gaaccgcgtg aagtgttcat taaacgtgcc aacgagaagc gtgctcgcgt    1080
ccaggagctg cgcgccaaag gtctgtccat gcgcgctatc gcggcagaga ttggttgctc    1140
ggtgggcacg gttcaccgct acgtcaaaga agttgaagag aagaaaaccg cgtaa         1195

<210> SEQ ID NO 2
<211> LENGTH: 2675
<212> TYPE: DNA
<213> ORGANISM: Artificial Sequence
<220> FEATURE:
<223> OTHER INFORMATION: Synthetic Construct; Cloning vector pHSG298

<400> SEQUENCE: 2
gaggtctgcc tcgtgaagaa ggtgttgctg actcatacca ggcctgaatc gccccatcat      60
ccagccagaa agtgagggag ccacggttga tgagagcttt gttgtaggtg gaccagttgg     120
tgattttgaa cttttgcttt gccacggaac ggtctgcgtt gtcgggaaga tgcgtgatct     180
gatccttcaa ctcagcaaaa gttcgattta ttcaacaaag ccacgttgtg tctcaaaatc     240
```

```
tctgatgtta cattgcacaa gataaaaata tatcatcatg aacaataaaa ctgtctgctt    300
acataaacag taatacaagg ggtgttatga gccatattca acgggaaacg tcttgctcga    360
agccgcgatt aaattccaac atggatgctg atttatatgg gtataaatgg gctcgcgata    420
atgtcgggca atcaggtgcg acaatctatc gattgtatgg gaagcccgat gcgccagagt    480
tgtttctgaa acatggcaaa ggtagcgttg ccaatgatgt tacagatgag atggtcagac    540
taaactggct gacggaattt atgcctcttc cgaccatcaa gcattttatc cgtactcctg    600
atgatgcatg gttactcacc actgcgatcc ccgggaaaac agcattccag gtattagaag    660
aatatcctga ttcaggtgaa aatattgttg atgcgctggc agtgttcctg cgccggttgc    720
attcgattcc tgtttgtaat tgtcctttta acagcgatcg cgtatttcgt ctcgctcagg    780
cgcaatcacg aatgaataac ggtttggttg atgcgagtga ttttgatgac gagcgtaatg    840
gctggcctgt tgaacaagtc tggaaagaaa tgcataagct tttgccattc tcaccggatt    900
cagtcgtcac tcatggtgat ttctcacttg ataaccttat ttttgacgag ggaaaattaa    960
taggttgtat tgatgttgga cgagtcggaa tcgcagaccg ataccaggat cttgccatcc   1020
tatggaactg cctcggtgag ttttctcctt cattacagaa acggcttttt caaaaatatg   1080
gtattgataa tcctgatatg aataaattgc agtttcattt gatgctcgat gagttttct   1140 aatcagaatt ggttaattgg ttgtaacact ggcagagcat tacgctgact tgacgggacg   1200
gcggctttgt tgaataaatc gcattcgcca ttcaggctgc gcaactgttg ggaagggcga   1260
tcggtgcggg cctcttcgct attacgccag ctggcgaaag ggggatgtgc tgcaaggcga   1320
ttaagttggg taacgccagg gttttcccag tcacgacgtt gtaaaacgac ggccagtgcc   1380
aagcttgcat gcctgcaggt cgactctaga ggatccccgg gtaccgagct cgaattcgta   1440
atcatgtcat agctgtttcc tgtgtgaaat tgttatccgc tcacaattcc acacaacata   1500
cgagccggaa gcataaagtg taaagcctgg ggtgcctaat gagtgagcta actcacatta   1560
attgcgttgc gctcactgcc cgcttttcag tcgggaaacc tgtcgtgcca gctgcattaa   1620
tgaatcggcc aacgcgcggg gagaggcggt ttgcgtattg gcgaacttttt gctgagttga   1680 aggatcagat cacgcatctt cccgacaacg cagaccgttc cgtggcaaag caaaagttca   1740
aaatcagtaa ccgtcagtgc cgataagttc aaagttaaac ctggtgttga taccaacatt   1800
gaaacgctga tcgaaaacgc gctgaaaaac gctgctgaat gtgcgagctt cttccgcttc   1860
ctcgctcact gactcgctgc gctcggtcgt tcggctgcgg cgagcggtat cagctcactc   1920
aaaggcggta atacggttat ccacagaatc aggggataac gcaggaaaga acatgtgagc   1980
aaaaggccag caaaaggcca ggaaccgtaa aaaggccgcg ttgctggcgt ttttccatag   2040
gctccgcccc cctgacgagc atcacaaaaa tcgacgctca agtcagaggt ggcgaaaccc   2100
gacaggacta taaagatacc aggcgtttcc ccctggaagc tccctcgtgc gctctcctgt   2160
tccgaccctg ccgcttaccg gatacctgtc cgcctttctc ccttcgggaa gcgtggcgct   2220
ttctcaatgc tcacgctgta ggtatctcag ttcggtgtag gtcgttcgct ccaagctggg   2280
ctgtgtgcac gaaccccccg ttcagcccga ccgctgcgcc ttatccggta actatcgtct   2340
tgagtccaac ccggtaagac acgacttatc gccactggca gcagccactg gtaacaggat   2400
tagcagagcg aggtatgtag gcggtgctac agagttcttg aagtggtggc ctaactacgg   2460
ctacactaga aggacagtat ttggtatctg cgctctgctg aagccagtta ccttcggaaa   2520
aagagttggt agctcttgat ccggcaaaca aaccaccgct ggtagcggtg gttttttgt    2580 ttgcaagcag cagattacgc gcagaaaaaa aggatctcaa gaagatcctt tgatcttttc   2640
```

```
tacggggtct gacgctcagt ggaacgatcc gtcga                                   2675
```

<210> SEQ ID NO 3
<211> LENGTH: 25
<212> TYPE: DNA
<213> ORGANISM: Artificial Sequence
<220> FEATURE:
<223> OTHER INFORMATION: Synthetic Construct; Primer

<400> SEQUENCE: 3

```
atagatctag aacgtccgta ggagc                                                25
```

<210> SEQ ID NO 4
<211> LENGTH: 26
<212> TYPE: DNA
<213> ORGANISM: Artificial Sequence
<220> FEATURE:
<223> OTHER INFORMATION: Synthetic Construct; Primer

<400> SEQUENCE: 4

```
atagatctga cttggttacg atggac                                               26
```

<210> SEQ ID NO 5
<211> LENGTH: 27
<212> TYPE: DNA
<213> ORGANISM: Artificial Sequence
<220> FEATURE:
<223> OTHER INFORMATION: Synthetic Construct; Primer

<400> SEQUENCE: 5

```
atagatctag gtttcccgac tggaaag                                              27
```

<210> SEQ ID NO 6
<211> LENGTH: 28
<212> TYPE: DNA
<213> ORGANISM: Artificial Sequence
<220> FEATURE:
<223> OTHER INFORMATION: Synthetic Construct; Primer

<400> SEQUENCE: 6

```
atagatctcg tgccagctgc attaatga                                             28
```

<210> SEQ ID NO 7
<211> LENGTH: 1885
<212> TYPE: DNA
<213> ORGANISM: Corynebacterium glutamicum

<400> SEQUENCE: 7

```
agcatggtcg tcacagagct ggaagcggca gcgagaatta tccgcgatcg tggcgcggtg          60
cccgcaggca tgacaaacat cgtaaatgcc gcgtttcgtg tggccgtggc cgcccaggac         120
gtgtcagcgc cgccaccacc tgcaccgaat cggcagcagc gtcgcgcgtc gaaaaagcgc         180
acaggcggca agaagcgata agctgcacga atacctgaaa aatgttgaac gccccgtgag         240
cggtaactca cagggcgtcg gctaacccca gtccaaacc tgggagaaag cgctcaaaaa          300
tgactctagc ggattcacga gacattgaca caccggcctg gaaattttcc gctgatctgt         360
tcgacaccca tcccgagctc gcgctgcgat cacgtggctg gacgagcgaa gaccgccgcg         420
aattcctcgc tcacctgggc agagaaaatt tccagggcag caagaccgc gacttcgcca         480 gcgcttggat caaagacccg gacacgggag aaacacagcc gaagttatac cgagttggtt         540
caaaatcgct tgcccggtgc cagtatgttg ctctgacgca cgcgcagcac gcagccgtgc         600
```

```
ttgtcctgga cattgatgtg ccgagccacc aggccggcgg gaaaatcgag cacgtaaacc      660
ccgaggtcta cgcgattttg gagcgctggg cacgcctgga aaaagcgcca gcttggatcg      720
gcgtgaatcc actgagcggg aaatgccagc tcatctggct cattgatccg gtgtatgccg      780
cagcaggcat gagcagcccg aatatgcgcc tgctggctgc aacgaccgag gaaatgaccc      840
gcgttttcgg cgctgaccag gcttttccac ataggctgag ccggtggcca ctgcacgtct      900
ccgacgatcc caccgcgtac cgctggcatg cccagcacaa tcgcgtggat cgcctagctg      960
atcttatgga ggttgctcgc atgatctcag gcacagaaaa acctaaaaaa cgctatgagc     1020
aggagttttc tagcggacgg gcacgtatcg aagcggcaag aaaagccact gcggaagcaa     1080
aagcacttgc cacgcttgaa gcaagcctgc cgagcgccgc tgaagcgtct ggagagctga     1140
tcgacggcgt ccgtgtcctc tggactgctc cagggcgtgc cgcccgtgat gagacggctt     1200
ttcgccacgc tttgactgtg ggataccagt taaaagcggc tggtgagcgc ctaaaagaca     1260
ccaagatcat cgacgcctac gagcgtgcct acaccgtcgc tcaggcggtc ggagcagacg     1320
gccgtgagcc tgatctgccg ccgatgcgtg accgccagac gatggcgcga cgtgtgcgcg     1380
gctacgtcgc taaaggccag ccagtcgtcc ctgctcgtca gacagagacg cagagcagcc     1440
gagggcgaaa agctctggcc actatgggaa gacgtggcgg taaaaaggcc gcagaacgct     1500
ggaaagaccc aaacagtgag tacgcccgag cacagcgaga aaaactagct aagtccagtc     1560
aacgacaagc taggaaagct aaaggaaatc gcttgaccat gcaggttggg ttatgactg      1620 ttgagggaga gactggctcg tggccgacaa tcaatgaagc tatgtctgaa tttagcgtgt     1680
cacgtcagac cgtgaataga gcacttaagt ctgcgggcat tgaacttcca cgaggacgcc     1740
gtaaagcttc ccagtaaatg tgccatctcg taggcagaaa acggttcccc ccgtaggggt     1800
ctctctcttg gcctccttttc taggtcgggc tgattgctct tgaagctctc taggggggct     1860
cacaccatag gcagataacg gttcc                                            1885
```

<210> SEQ ID NO 8
<211> LENGTH: 2227
<212> TYPE: DNA
<213> ORGANISM: Artificial Sequence
<220> FEATURE:
<223> OTHER INFORMATION: Synthetic Construct; Cloning vector pHSG398

<400> SEQUENCE: 8

```
acggaagatc acttcgcaga ataaataaat cctggtgtcc ctgttgatac cgggaagccc       60
tgggccaact tttggcgaaa atgagacgtt gatcggcacg taagaggttc aactttcac      120 cataatgaaa taagatcact accgggcgta ttttttgagt tatcgagatt ttcaggagct      180
aaggaagcta aaatggagaa aaaaatcact ggatatacca ccgttgatat atcccaatgg      240
catcgtaaag aacattttga ggcatttcag tcagttgctc aatgtaccta taaccagacc      300
gttcagctgg atattacggc ctttttaaag accgtaaaga aaataagcac aagttttat      360 ccggccttta ttcacattct tgcccgcctg atgaatgctc atccggaatt tcgtatggca      420
atgaaagacg gtgagctggt gatatgggat agtgttcacc cttgttacac cgttttccat      480
gagcaaactg aaacgttttc atcgctctgg agtgaatacc acgacgattt ccggcagttt      540
ctacacatat attcgcaaga tgtggcgtgt tacggtgaaa acctggccta tttccctaaa      600
gggtttattg agaatatgtt tttcgtctca gccaatccct gggtgagttt caccagtttt      660
gatttaaacg tggccaatat ggacaacttc ttcgcccccg ttttcaccat gggcaaatat      720
tatacgcaag gcgacaaggt gctgatgccg ctggcgattc aggttcatca tgccgtctgt      780
```

```
gatggcttcc atgtcggcag aatgcttaat gaattacaac agtactgcga tgagtggcag      840
ggcggggcgt aattttttta aggcagttat tggtgccctt aaacgcctgg tgctacgcct      900
gaataagtga taataagcgg atgaatggca gaaattcagc ttggcccagt gccaagctcc      960
aatacgcaaa ccgcctctcc ccgcgcgttg gccgattcat taatgcagct ggcacgacag     1020
gtttcccgac tggaaagcgg gcagtgagcg caacgcaatt aatgtgagtt agctcactca     1080
ttaggcaccc caggctttac actttatgct tccggctcgt atgttgtgtg gaattgtgag     1140
cggataacaa tttcacacag gaaacagcta tgaccatgat tacgaattcg agctcggtac     1200
ccggggatcc tctagagtcg acctgcaggc atgcaagctt ggcactggcc gtcgttttac     1260
aacgtcgtga ctgggaaaac cctggcgtta cccaacttaa tcgccttgca gcacatcccc     1320
ctttcgccag ctggcgtaat agcgaagagg cccgcaccga tcgcccttcc caacagttgc     1380
gcagcctgaa tggcgaatga gcttcttccg cttcctcgct cactgactcg ctgcgctcgg     1440
tcgttcggct gcggcgagcg gtatcagctc actcaaaggc ggtaatacgg ttatccacag     1500
aatcagggga taacgcagga agaacatgt gagcaaaagg ccagcaaaag gccaggaacc     1560
gtaaaaaggc cgcgttgctg cgttttttcc ataggctccg cccccctgac gagcatcaca     1620
aaaatcgacg ctcaagtcag aggtggcgaa acccgacagg actataaaga taccaggcgt     1680
ttccccctgg aagctccctc gtgcgctctc ctgttccgac cctgccgctt accggatacc     1740
tgtccgcctt tctcccttcg ggaagcgtgg cgctttctca atgctcacgc tgtaggtatc     1800
tcagttcggt gtaggtcgtt cgctccaagc tgggctgtgt gcacgaaccc ccgttcagc      1860 ccgaccgctg cgccttatcc ggtaactatc gtcttgagtc caacccggta agacacgact     1920
tatcgccact ggcagcagcc actggtaaca ggattagcag agcgaggtat gtaggcggtg     1980
ctacagagtt cttgaagtgg tggcctaact acggctacac tagaaggaca gtatttggta     2040
tctgcgctct gctgaagcca gttaccttcg gaaaaagagt tggtagctct tgatccggca     2100
aacaaaccac cgctggtagc ggtggttttt tgtttgcaa gcagcagatt acgcgcagaa     2160
aaaaaggatc tcaagaagat cctttgatct tttctacggg gtctgacgct cagtggaact     2220
ccgtcga                                                               2227
```

<210> SEQ ID NO 9
<211> LENGTH: 26
<212> TYPE: DNA
<213> ORGANISM: Artificial Sequence
<220> FEATURE:
<223> OTHER INFORMATION: Synthetic Construct; Primer

<400> SEQUENCE: 9
atagatctag catggtcgtc acagag                                          26

<210> SEQ ID NO 10
<211> LENGTH: 28
<212> TYPE: DNA
<213> ORGANISM: Artificial Sequence
<220> FEATURE:
<223> OTHER INFORMATION: Synthetic Construct; Primer

<400> SEQUENCE: 10
atagatctgg aaccgttatc tgcctatg                                        28

<210> SEQ ID NO 11
<211> LENGTH: 28
<212> TYPE: DNA

```
<213> ORGANISM: Artificial Sequence
<220> FEATURE:
<223> OTHER INFORMATION: Synthetic Construct; Primer

<400> SEQUENCE: 11
atagatctgt cgaacggaag atcacttc                                          28

<210> SEQ ID NO 12
<211> LENGTH: 26
<212> TYPE: DNA
<213> ORGANISM: Artificial Sequence
<220> FEATURE:
<223> OTHER INFORMATION: Synthetic Construct; Primer

<400> SEQUENCE: 12
atagatctag ttccactgag cgtcag                                            26

<210> SEQ ID NO 13
<211> LENGTH: 4125
<212> TYPE: DNA
<213> ORGANISM: Artificial Sequence
<220> FEATURE:
<223> OTHER INFORMATION: Synthetic Construct; Cloning Vector pCRB11

<400> SEQUENCE: 13
ctgtcgaacg gaagatcact tcgcagaata aataaatcct ggtgtccctg ttgataccgg         60
gaagccctgg gccaactttt ggcgaaaatg agacgttgat cggcacgtaa gaggttccaa        120
ctttcaccat aatgaaataa gatcactacc gggcgtattt tttgagttat cgagattttc        180
aggagctaag gaagctaaaa tggagaaaaa atcactggat ataccaccg ttgatatatc         240 ccaatggcat cgtaaagaac attttgaggc atttcagtca gttgctcaat gtacctataa        300
ccagaccgtt cagctggata ttacggcctt tttaaagacc gtaaagaaaa ataagcacaa        360
gttttatccg gcctttattc acattcttgc ccgcctgatg aatgctcatc cggaatttcg        420
tatggcaatg aaagacggtg agctggtgat atgggatagt gttcacccct tgttacaccgt      480 tttccatgag caaactgaaa cgttttcatc gctctggagt gaataccacg acgatttccg        540
gcagtttcta cacatatatt cgcaagatgt ggcgtgttac ggtgaaaacc tggcctattt        600
ccctaaaggg tttattgaga atatgttttt cgtctcagcc aatccctggg tgagtttcac        660
cagttttgat ttaaacgtgg ccaatatgga caacttcttc gcccccgttt tcaccatggg        720
caaatattat acgcaaggcg acaaggtgct gatgccgctg gcgattcagg ttcatcatgc        780
cgtttgtgat ggcttccatg tcggcagaat gcttaatgaa ttacaacagt actgcgatga        840
gtggcagggc ggggcgtaat tttttaagg cagttattgg tgcccttaaa cgcctggttg        900
ctacgcctga ataagtgata taagcggat gaatggcaga aattcagctt ggcccagtgc         960
caagctccaa tacgcaaacc gcctctcccc gcgcgttggc cgattcatta atgcagctgg       1020
cacgacaggt ttcccgactg gaaagcgggc agtgagcgca acgcaattaa tgtgagttag       1080
ctcactcatt aggcacccca ggctttacac tttatgcttc cggctcgtat gttgtgtgga       1140
attgtgagcg gataacaatt tcacacagga acagctatg accatgatta cgaattcgag        1200
ctcggtaccc ggggatcctc tagagtcgac ctgcaggcat gcaagcttgg cactggccgt       1260
cgttttacaa cgtcgtgact gggaaaaccc tggcgttacc caacttaatc gccttgcagc      1320 acatcccct tcgccagct ggcgtaatag cgaagaggcc cgcaccgatc gcccttccca        1380
acagttgcgc agcctgaatg gcgaatgagc ttcttccgct tcctcgctca ctgactcgct       1440
gcgctcggtc gttcggctgc ggcgagcggt atcagctcac tcaaaggcgg taatacggtt       1500
```

```
atccacagaa tcaggggata acgcaggaaa gaacatgtga gcaaaaggcc agcaaaaggc    1560
caggaaccgt aaaaaggccg cgttgctggc gttttccat aggctccgcc ccctgacga     1620 gcatcacaaa aatcgacgct caagtcagag gtggcgaaac ccgacaggac tataaagata   1680
ccaggcgttt ccccctggaa gctccctcgt gcgctctcct gttccgaccc tgccgcttac   1740
cggataccng tccgcctttc tcccttcggg aagcgtggcg ctttctcata gctcacgctg   1800
taggtatctc agttcggtgt aggtcgttcg ctccaagctg ggctgtgtgc acgaaccccc   1860
cgttcagccc gaccgctgcg ccttatccgg taactatcgt cttgagtcca acccggtaag   1920
acacgactta tcgccactgg cagcagccac tggtaacagg attagcagag cgaggtatgt   1980
aggcggtgct acagagttct tgaagtggtg gcctaactac ggctacacta agaacagt    2040 atttggtatc tgcgctctgc tgaagccagt taccttcgga aaagagttg gtagctcttg    2100 atccggcaaa caaaccaccg ctggtagcgg tggttttttt gtttgcaagc agcagattac   2160
gcgcagaaaa aaggatctca agaagatcc tttgatcttt tctacggggt ctgacgctca    2220
gtggaactag atctagcatg gtcgtcacag agctggaagc ggcagcgaga attatccgcg   2280
atcgtggcgc ggtgcccgca ggcatgacaa acatcgtaaa tgccgcgttt cgtgtggccg   2340
tggccgccca ggacgtgtca gcgccgccac cacctgcacc gaatcggcag cagcgtcgcg   2400
cgtcgaaaaa gcgcacaggc ggcaagaagc gataagctgc acgaatacct gaaaatgtt    2460 gaacgccccg tgagcggtaa ctcacagggc gtcggctaac ccccagtcca aacctgggag   2520
aaagcgctca aaatgactc tagcggattc acgagacatt gacacaccgg cctggaaatt    2580
ttccgctgat ctgttcgaca cccatcccga gctcgcgctg cgatcacgtg gctggacgag   2640
cgaagaccgc cgcgaattcc tcgctcacct gggcagagaa aatttccagg gcagcaagac   2700
ccgcgacttc gccagcgctt ggatcaaaga cccggacacg ggagaaacac agccgaagtt   2760
ataccgagtt ggttcaaaat cgcttgcccg gtgccagtat gttgctctga cgcacgcgca   2820
gcacgcagcc gtgcttgtcc tggacattga tgtgccgagc caccaggccg gcgggaaaat   2880
cgagcacgta aaccccgagg tctacgcgat tttggagcgc tgggcacgcc tggaaaaagc   2940
gccagcttgg atcggcgtga atccactgag cgggaaatgc cagctcatct ggctcattga   3000
tccggtgtat gccgcagcag gcatgagcag cccgaatatg cgcctgctgg ctgcaacgac   3060
cgaggaaatg acccgcgttt tcggcgctga ccaggctttt tcacataggc tgagccggtg   3120
gccactgcac gtctccgacg atcccaccgc gtaccgctgg catgcccagc acaatcgcgt   3180
ggatcgccta gctgatctta tggaggttgc tcgcatgatc tcaggcacag aaaaacctaa   3240
aaaacgctat gagcaggagt tttctagcgg acgggcacgt atcgaagcgg caagaaaagc   3300
cactgcggaa gcaaaagcac ttgccacgct gaagcaagc ctgccgagcg ccgctgaagc    3360
gtctggagag ctgatcgacg gcgtccgtgt cctctggact gctccagggc gtgccgcccg   3420
tgatgagacg gcttttcgcc acgctttgac tgtgggatac cagttaaaag cggctggtga   3480
gcgcctaaaa gacaccaaga tcatcgacgc ctacgagcgt gcctacaccg tcgctcaggc   3540
ggtcggagca gacggccgtg agcctgatct gccgccgatg cgtgaccgcc agacgatggc   3600
gcgacgtgtg cgcggctacg tcgctaaagg ccagccagtc gtccctgctc gtcagacaga   3660
gacgcagagc agccgagggc gaaaagctct ggccactatg ggaagacgtg gcggtaaaaa   3720
ggccgcagaa cgctggaaag acccaaacag tgagtacgcc cgagcacagc gagaaaaact   3780
agctaagtcc agtcaacgac aagctaggaa agctaaagga aatcgcttga ccattgcagg   3840
```

| | |
|---|---|
| ttggtttatg actgttgagg gagagactgg ctcgtggccg acaatcaatg aagctatgtc | 3900 |
| tgaatttagc gtgtcacgtc agaccgtgaa tagagcactt aagtctgcgg gcattgaact | 3960 |
| tccacgagga cgccgtaaag cttcccagta aatgtgccat ctcgtaggca gaaaacggtt | 4020 |
| cccccgtag gggtctctct cttggcctcc tttctaggtc gggctgattg ctcttgaagc | 4080 |
| tctctagggg ggctcacacc ataggcagat aacggttcca gatct | 4125 |

<210> SEQ ID NO 14
<211> LENGTH: 465
<212> TYPE: DNA
<213> ORGANISM: Artificial Sequence
<220> FEATURE:
<223> OTHER INFORMATION: Synthetic Construct; Zeocin resistant gene

<400> SEQUENCE: 14

| | |
|---|---|
| tagcttatcc tcagtcctgc tcctctgcca caaagtgcac gcagttgccg gccgggtcgc | 60 |
| gcagggcgaa ctcccgcccc cacggctgct cgccgatctc ggtcatggcc ggcccggagg | 120 |
| cgtcccggaa gttcgtggac acgacctccg accactcggc gtacagctcg tccaggccgc | 180 |
| gcacccacac ccaggccagg gtgttgtccg gcaccacctg gtcctggacc gcgctgatga | 240 |
| acagggtcac gtcgtcccgg accacaccgg cgaagtcgtc ctccacgaag tcccgggaga | 300 |
| acccgagccg gtcggtccag aactcgaccg ctccggcgac gtcgcgcgcg gtgagcaccg | 360 |
| gaacggcact ggtcaacttg gccatgatgg ccctcctata gtgagtcgta ttatactatg | 420 |
| ccgatatact atgccgatga ttaattgtca aaacagcgtg gatgg | 465 |

<210> SEQ ID NO 15
<211> LENGTH: 28
<212> TYPE: DNA
<213> ORGANISM: Artificial Sequence
<220> FEATURE:
<223> OTHER INFORMATION: Synthetic Construct; Primer

<400> SEQUENCE: 15

| | |
|---|---|
| atgatatccg aagtgatctt ccgttcga | 28 |

<210> SEQ ID NO 16
<211> LENGTH: 28
<212> TYPE: DNA
<213> ORGANISM: Artificial Sequence
<220> FEATURE:
<223> OTHER INFORMATION: Synthetic Construct; Primer

<400> SEQUENCE: 16

| | |
|---|---|
| atgatatcaa ggcagttatt ggtgccct | 28 |

<210> SEQ ID NO 17
<211> LENGTH: 28
<212> TYPE: DNA
<213> ORGANISM: Artificial Sequence
<220> FEATURE:
<223> OTHER INFORMATION: Synthetic Construct; Primer

<400> SEQUENCE: 17

| | |
|---|---|
| atgatatcta gcttatcctc agtcctgc | 28 |

<210> SEQ ID NO 18
<211> LENGTH: 28
<212> TYPE: DNA
<213> ORGANISM: Artificial Sequence
<220> FEATURE:
<223> OTHER INFORMATION: Synthetic Construct; Primer

<400> SEQUENCE: 18
atgatatccc atccacgctg ttttgaca                                              28

<210> SEQ ID NO 19
<211> LENGTH: 5018
<212> TYPE: DNA
<213> ORGANISM: Artificial Sequence
<220> FEATURE:
<223> OTHER INFORMATION: Synthetic Construct; Cloning vector pCRC200

<400> SEQUENCE: 19

| | | | | | |
|---|---|---|---|---|---|
| atgaccatga | ttacgaatta | attcgagctc | aggcagccat | cggaagctgt | ggtatggctg | 60 |
| tgcaggtcgt | aaatcactgc | ataattcgtg | tcgctcaagg | cgcactcccg | ttctggataa | 120 |
| tgttttttgc | gccgacatca | taacggttct | ggcaaatatt | ctgaaatgag | ctgttgacaa | 180 |
| ttaatcatcg | gctcgtataa | tgtgtggaat | tgtgagcgga | taacaatttc | acacaggaaa | 240 |
| cagaattccc | ggggatccgt | cgacctgcag | ccaagcttgg | ctgttttggc | ggatgagaga | 300 |
| agattttcag | cctgatacag | attaaatcag | aacgcagaag | cggtctgata | aaacagaatt | 360 |
| tgcctggcgg | cagtagcgcg | tggtcccac | ctgaccccat | gccgaactca | gaagtgaaac | 420 |
| gccgtagcgc | cgatggtagt | gtggggtctc | cccatgcgag | agtagggaac | tgccaggcat | 480 |
| caaataaaac | gaaaggctca | gtcgaaagac | tgggcctttc | gttttatctg | ttgtttgtcg | 540 |
| gtgaacgctc | tcctgagtag | gacaaatccg | ccgggagcgg | atttgaacgt | tgcgaagcaa | 600 |
| cggcccggag | ggtggcgggc | aggacgcccg | ccataaactg | ccaggcatca | aattaagcag | 660 |
| aaggccatcc | tgacggatgg | cctttttgcg | tttctacaaa | ctcttttgtt | tatttttcta | 720 |
| aatacattca | aatatgtatc | cgctcatgag | acaataaccc | tgataaatgc | ttcaataata | 780 |
| ttgaaaaagg | aagagtatga | gtattcaaca | tttccgtgtc | gcccttattc | ccttttttgc | 840 |
| ggcattttgc | cttcctgttt | ttgctcaccc | agaaacgctg | gtgaaagtaa | aagatgctga | 900 |
| agatcagttg | ggtgcacgag | tgggttacat | cgaactggat | ctcaacagcg | gtaagatcct | 960 |
| tgagagtttt | cgccccgaag | aacgttttcc | aatgatgagc | acttttaaag | ttctgctatg | 1020 |
| tggcatgcaa | gctagcttgg | cactggccgt | cgttttacaa | cgtcgtgact | gggaaaaccc | 1080 |
| tggcgttacc | caacttaatc | gccttgcagc | acatccccct | ttcgccagct | ggcgtaatag | 1140 |
| cgaagaggcc | cgcaccgatc | gcccttccca | acagttgcgc | agcctgaatg | gcgaatgagc | 1200 |
| ttcttccgct | tcctcgctca | ctgactcgct | gcgctcggtc | gttcggctgc | ggcgagcggt | 1260 |
| atcagctcac | tcaaaggcgg | taatacggtt | atccacagaa | tcaggggata | acgcaggaaa | 1320 |
| gaacatgtga | gcaaaaggcc | agcaaaaggc | caggaaccgt | aaaaaggccg | cgttgctggc | 1380 |
| gttttccat | aggctccgcc | ccctgacga | gcatcacaaa | aatcgacgct | caagtcagag | 1440 |
| gtggcgaaac | ccgacaggac | tataaagata | ccaggcgttt | ccccctggaa | gctccctcgt | 1500 |
| gcgctctcct | gttccgaccc | tgccgcttac | cggatacctg | tccgcctttc | tcccttcggg | 1560 |
| aagcgtggcg | ctttctcaat | gctcacgctg | taggtatctc | agttcggtgt | aggtcgttcg | 1620 |
| ctccaagctg | ggctgtgtgc | acgaaccccc | cgttcagccc | gaccgctgcg | ccttatccgg | 1680 |
| taactatcgt | cttgagtcca | acccggtaag | acacgactta | tcgccactgg | cagcagccac | 1740 |
| tggtaacagg | attagcagag | cgaggtatgt | aggcggtgct | acagagttct | tgaagtggtg | 1800 |
| gcctaactac | ggctacacta | gaaggacagt | atttggtatc | tgcgctctgc | tgaagccagt | 1860 |
| taccttcgga | aaaagagttg | gtagctcttg | atccggcaaa | caaaccaccg | ctggtagcgg | 1920 |

-continued

```
tggttttttt gtttgcaagc agcagattac gcgcagaaaa aaaggatctc aagaagatcc    1980
tttgatcttt tctacggggt ctgacgctca gtggaacgat aacacatgca gtcatgtcgt    2040
gctaatgtgt aaaacatgta catgcagatt gctgggggtg caggggggcgg agccaccctg    2100 tccatgcggg gtgtggggct tgccccgccg gtacagacag tgagcaccgg ggcacctagt    2160
cgcggatacc ccccctaggt atcggacacg taaccctccc atgtcgatgc aaatctttaa    2220
cattgagtac gggtaagctg gcacgcatag ccaagctagg cggccaccaa acaccactaa    2280
aaattaatag tccctagaca agacaaaccc ccgtgcgagc taccaactca tatgcacggg    2340
ggccacataa cccgaagggg tttcaattga caaccatagc actagctaag acaacgggca    2400
caacacccgc acaaactcgc actgcgcaac cccgcacaac atcgggtcta ggtaacactg    2460
aaatagaagt gaacacctct aaggaaccgc aggtcaatga gggttctaag gtcactcgcg    2520
ctagggcgtg gcgtaggcaa aacgtcatgt acaagatcac caatagtaag gctctggcgg    2580
ggtgccatag gtggcgcagg gacgaagctg ttgcggtgtc ctggtcgtct aacggtgctt    2640
cgcagtttga gggtctgcaa aactctcact ctcgctgggg gtcacctctg gctgaattgg    2700
aagtcatggg cgaacgccgc attgagctgg ctattgctac taagaatcac ttggcggcgg    2760
gtggcgcgct catgatgttt gtgggcactg ttcgacacaa ccgctcacag tcatttgcgc    2820
aggttgaagc gggtattaag actgcgtact cttcgatggt gaaaacatct cagtggaaga    2880
aagaacgtgc acggtacggg gtggagcaca cctatagtga ctatgaggtc acagactctt    2940
gggcgaacgg ttggcacttg caccgcaaca tgctgttgtt cttggatcgt ccactgtctg    3000
acgatgaact caaggcgttt gaggattcca tgttttcccg ctggtctgct ggtgtggtta    3060
aggccggtat ggacgcgcca ctgcgtgagc acggggtcaa acttgatcag gtgtctacct    3120
ggggtggaga cgctgcgaaa atggcaacct acctcgctaa gggcatgtct caggaactga    3180
ctggctccgc tactaaaacc gcgtctaagg ggtcgtacac gccgtttcag atgttggata    3240
tgttggccga tcaaagcgac gccggcgagg atatggacgc tgttttggtg gctcggtggc    3300
gtgagtatga ggttggttct aaaaaacctgc gttcgtcctg gtcacgtggg gctaagcgtg    3360 cttttgggcat tgattacata gacgctgatg tacgtcgtga aatggaagaa gaactgtaca    3420
agctcgccgg tctggaagca ccggaacggg tcgaatcaac ccgcgttgct gttgctttgg    3480
tgaagcccga tgattggaaa ctgattcagt ctgatttcgc ggttaggcag tacgttctag    3540
attgcgtgga taaggctaag gacgtggccg ctgcgcaacg tgtcgctaat gaggtgctgg    3600
caagtctggg tgtggattcc accccgtgca tgatcgttat ggatgatgtg gacttggacg    3660
cggttctgcc tactcatggg gacgctacta agcgtgatct gaatgcggcg gtgttcgcgg    3720
gtaatgagca gactattctt cgcacccact aaaaagcggca taaacccgt tcgatatttt    3780 gtgcgatgaa tttatggtca atgtcgcggg ggcaaactat gatgggtctt gttgtgttat    3840
ctccgtcgaa cggaagatca cttcgcagaa taaataaatc ctggtgtccc tgttgatacc    3900
gggaagccct gggccaactt ttggcgaaaa tgagacgttg atcggcacgt aagaggttcc    3960
aactttcacc ataatgaaat aagatcacta ccgggcgtat ttttgagtt atcgagattt    4020 tcaggagcta aggaagctaa aatggagaaa aaaatcactg gatataccac cgttgatata    4080
tcccaatggc atcgtaaaga acattttgag gcatttcagt cagttgctca atgtacctat    4140
aaccagaccg ttcagctgga tattacggcc ttttaaaga ccgtaaagaa aaataagcac    4200
aagttttatc cggcctttat tcacattctt gcccgcctga tgaatgctca tccggaattt    4260
cgtatggcaa tgaaagacgg tgagctggtg atatgggata gtgttcaccc ttgttacacc    4320
```

```
gttttccatg agcaaactga aacgttttca tcgctctgga gtgaatacca cgacgatttc   4380
cggcagtttc tacacatata ttcgcaagat gtggcgtgtt acggtgaaaa cctggcctat   4440
ttccctaaag ggtttattga gaatatgttt ttcgtctcag ccaatccctg ggtgagtttc   4500
accagttttg atttaaacgt ggccaatatg gacaacttct tcgcccccgt tttcaccatg   4560
ggcaaatatt atacgcaagg cgacaaggtg ctgatgccgc tggcgattca ggttcatcat   4620
gccgtctgtg atggcttcca tgtcggcaga atgcttaatg aattacaaca gtactgcgat   4680
gagtggcagg gcggggcgta atttttttaa ggcagttatt ggtgccctta aacgcctggt   4740
gctacgcctg aataagtgat aataagcgga tgaatggcag aaattcagct tggcccagtg   4800
ccaagctcca atacgcaaac cgcctctccc cgcgcgttgg ccgattcatt aatgcagctg   4860
gcacgacagg tttcccgact ggaaagcggg cagtgagcgc aacgcaatta atgtgagtta   4920
gctcactcat taggcacccc aggctttaca ctttatgctt ccggctcgta tgttgtgtgg   4980
aattgtgagc ggataacaat ttcacacagg aaacagct                            5018

<210> SEQ ID NO 20
<211> LENGTH: 42
<212> TYPE: DNA
<213> ORGANISM: Artificial Sequence
<220> FEATURE:
<223> OTHER INFORMATION: Synthetic Construct; Primer

<400> SEQUENCE: 20
ctctactagt gtcgacggat ccttgtgtgg aattgtgagc gg                          42

<210> SEQ ID NO 21
<211> LENGTH: 30
<212> TYPE: DNA
<213> ORGANISM: Artificial Sequence
<220> FEATURE:
<223> OTHER INFORMATION: Synthetic Construct; Primer

<400> SEQUENCE: 21
ctctactagt catacgagcc ggaagcataa                                        30

<210> SEQ ID NO 22
<211> LENGTH: 551
<212> TYPE: DNA
<213> ORGANISM: Corynebacterium glutamicum

<400> SEQUENCE: 22
ccgaagatct gaagattcct gatacaaatt ctgttgtgac ggaagatttg ttggaagaaa     60
tctagtcgct cgtctcataa aaacgaccga gcctattggg attaccattg aagccagtgt    120
gagttgcatc acactggctt caaatctgag actttacttt gtggattcac gggggtgtag    180
tgcaattcat aattagcccc attcggggga gcagatcgcg gcgcgaacga tttcaggttc    240
gttccctgca aaaactattt agcgcaagtg ttggaaatgc cccgtctgg ggtcaatgtc     300 tattttttgaa tgtgtttgta tgattttgaa tccgctgcaa aatctttgtt tccccgctaa   360
agttggggac aggttgacac ggagttgact cgacgaatta ccaatgtga gtaggtttgg     420 tgcgtgagtt ggaaaatttc gccatactcg cccttgggtt ctgtcagctc aagaattctt    480
gagtgaccga tgctctgatt gacctaactg cttgacacat tgcatttcct acaatcttta    540
gaggagacac a                                                          551

<210> SEQ ID NO 23
```

-continued

<211> LENGTH: 425
<212> TYPE: DNA
<213> ORGANISM: Artificial Sequence
<220> FEATURE:
<223> OTHER INFORMATION: Synthetic Construct; Cloning vector pKK223-2

<400> SEQUENCE: 23

```
ctgttttggc ggatgagaga agattttcag cctgatacag attaaatcag aacgcagaag      60
cggtctgata aaacagaatt tgcctggcgg cagtagcgcg gtggtcccac ctgaccccat     120
gccgaactca gaagtgaaac gccgtagcgc cgatggtagt gtggggtctc cccatgcgag     180
agtagggaac tgccaggcat caaataaaac gaaaggctca gtcgaaagac tgggcctttc     240
gttttatctg ttgtttgtcg gtgaacgctc tcctgagtag gacaaatccg ccgggagcgg     300
atttgaacgt tgcgaagcaa cggcccggag ggtggcgggc aggacgcccg ccataaactg     360
ccaggcatca aattaagcag aaggccatcc tgacggatgg cctttttgcg tttctacaaa     420
ctctt                                                                 425
```

<210> SEQ ID NO 24
<211> LENGTH: 31
<212> TYPE: DNA
<213> ORGANISM: Artificial Sequence
<220> FEATURE:
<223> OTHER INFORMATION: Synthetic Construct; Primer

<400> SEQUENCE: 24

```
ctctgtcgac ccgaagatct gaagattcct g                                     31
```

<210> SEQ ID NO 25
<211> LENGTH: 46
<212> TYPE: DNA
<213> ORGANISM: Artificial Sequence
<220> FEATURE:
<223> OTHER INFORMATION: Synthetic Construct; Primer

<400> SEQUENCE: 25

```
ctctgtcgac ggatccccat ggtgtgtctc tctaaagat tgtagg                      46
```

<210> SEQ ID NO 26
<211> LENGTH: 36
<212> TYPE: DNA
<213> ORGANISM: Artificial Sequence
<220> FEATURE:
<223> OTHER INFORMATION: Synthetic Construct; Primer

<400> SEQUENCE: 26

```
ctctgcatgc ccatggctgt tttggcggat gagaga                                36
```

<210> SEQ ID NO 27
<211> LENGTH: 41
<212> TYPE: DNA
<213> ORGANISM: Artificial Sequence
<220> FEATURE:
<223> OTHER INFORMATION: Synthetic Construct; Primer

<400> SEQUENCE: 27

```
ctctgcatgc tcatgaaaga gtttgtagaa acgcaaaaag g                          41
```

<210> SEQ ID NO 28
<211> LENGTH: 349
<212> TYPE: DNA
<213> ORGANISM: Corynebacterium glutamicum

<400> SEQUENCE: 28

```
cggaactagc tctgcaatga cctgcgcgcc agggaggcg aggtgggtgg caggttttag    60
tgcgggttta agcgttgcca ggcgagtggt gagcagagac gctagtctgg ggagcgaaac   120
catattgagt catcttggca gagcatgcac aattctgcag gcatagatt ggttttgctc    180 gatttacaat gtgatttttt caacaaaaat aacacatggt ctgaccacat tttcggacat   240
aatcgggcat aattaaaggt gtaacaaagg aatccgggca caagctcttg ctgattttct   300
gagctgcttt gtgggttgtc cggttaggga atcaggaag tgggatcga                349
```

<210> SEQ ID NO 29
<211> LENGTH: 30
<212> TYPE: DNA
<213> ORGANISM: Artificial Sequence
<220> FEATURE:
<223> OTHER INFORMATION: Synthetic Construct; Primer

<400> SEQUENCE: 29

```
ctctgtcgac cggaactagc tctgcaatga                                     30
```

<210> SEQ ID NO 30
<211> LENGTH: 42
<212> TYPE: DNA
<213> ORGANISM: Artificial Sequence
<220> FEATURE:
<223> OTHER INFORMATION: Synthetic Construct; Primer

<400> SEQUENCE: 30

```
ctctgtcgac ggatcccata tgcgatccca cttcctgatt tc                        42
```

<210> SEQ ID NO 31
<211> LENGTH: 1716
<212> TYPE: DNA
<213> ORGANISM: Bacillus subtilis

<400> SEQUENCE: 31

```
gtgttgacaa aagcaacaaa agaacaaaaa tcccttgtga aaaacagagg ggcggagctt    60
gttgttgatt gcttagtgga gcaaggtgtc acacatgtat ttggcattcc aggtgcaaaa   120
attgatgcgg tatttgacgc tttacaagat aaaggacctg aaattatcgt tgcccggcac   180
gaacaaaacg cagcattcat ggcccaagca gtcggccgtt taactggaaa accgggagtc   240
gtgttagtca catcaggacc gggtgcctct aacttggcaa caggcctgct gacagcgaac   300
actgaaggag accctgtcgt tgcgcttgct ggaaacgtga tccgtgcaga tcgtttaaaa   360
cggacacatc aatctttgga taatgcggcg ctattccagc cgattacaaa atacagtgta   420
gaagttcaag atgtaaaaaa tataccggaa gctgttacaa atgcatttag atagcgtca    480 gcagggcagg ctgggccgc ttttgtgagc tttccgcaag atgttgtgaa tgaagtcaca   540
aatacgaaaa acgtgcgtgc tgttgcagcg ccaaaactcg gtcctgcagc agatgatgca   600
atcagtgcgg ccatagcaaa aatccaaaca gcaaaacttc ctgtcgtttt ggtcggcatg   660
aaaggcggaa gaccggaagc aattaaagcg gttcgcaagc ttttgaaaaa ggttcagctt   720
ccatttgttg aaacatatca agctgccggt accctttcta gagatttaga ggatcaatat   780 tttgccgta tcggtttgtt ccgcaaccag cctggcgatt tactgctaga gcaggcagat   840
gttgttctga cgatcggcta tgacccgatt gaatatgatc cgaaattctg gaatatcaat   900
ggagaccgga caattatcca tttagacgag attatcgctg acattgatca tgcttaccag   960
cctgatcttg aattgatcgg tgacattccg tccacgatca atcatatcga acacgatgct  1020
```

```
gtgaaagtgg aatttgcaga gcgtgagcag aaaatccttt ctgatttaaa acaatatatg      1080
catgaaggtg agcaggtgcc tgcagattgg aaatcagaca gagcgcaccc tcttgaaatc      1140
gttaaagagt tgcgtaatgc agtcgatgat catgttacag taacttgcga tatcggttcg      1200
cacgccattt ggatgtcacg ttatttccgc agctacgagc cgttaacatt aatgatcagt      1260
aacggtatgc aaacactcgg cgttgcgctt ccttgggcaa tcggcgcttc attggtgaaa      1320
ccgggagaaa aagtggtttc tgtctctggt gacggcggtt tcttattctc agcaatggaa      1380
ttagagacag cagttcgact aaaagcacca attgtacaca ttgtatggaa cgacagcaca      1440
tatgacatgt ttgcattcca gcaattgaaa aaatataacc gtacatctgc ggtcgatttc      1500
ggaaatatcg atatcgtgaa atatgcggaa agcttcggag caactggctt gcgcgtagaa      1560
tcaccagacc agctggcaga tgttctgcgt caaggcatga cgctgaaggt cctgtcatc       1620 atcgatgtcc cggttgacta cagtgataac attaatttag caagtgacaa gcttccgaaa      1680
gaattcgggg aactcatgaa acgaaagct ctctag                                 1716

<210> SEQ ID NO 32
<211> LENGTH: 39
<212> TYPE: DNA
<213> ORGANISM: Artificial Sequence
<220> FEATURE:
<223> OTHER INFORMATION: Synthetic Construct; Primer

<400> SEQUENCE: 32
ctctccatgg tgacaaaagc aacaaaagaa caaaaatcc                              39

<210> SEQ ID NO 33
<211> LENGTH: 40
<212> TYPE: DNA
<213> ORGANISM: Artificial Sequence
<220> FEATURE:
<223> OTHER INFORMATION: Synthetic Construct; Primer

<400> SEQUENCE: 33
ctctccatgg agatctctag agagctttcg ttttcatgag                             40

<210> SEQ ID NO 34
<211> LENGTH: 3588
<212> TYPE: DNA
<213> ORGANISM: Corynebacterium glutamicum

<400> SEQUENCE: 34
gtgaatgtgg cagcttctca acagcccact cccgccacgg ttgcaagccg tggtcgatcc      60
gccgcccctg agcggatgac aggtgcacag gcaattgttc gatcgctcga ggagcttaac      120
gccgacatcg tgttcggtat tcctggtggt gcggtgctac cggtgtatga cccgctctat      180
tcctccacaa aggtgcgcca cgtcttggtg cgccacgagc agggcgcagg ccacgcagca      240
accggctacg cgcaggttac tggacgcgtt ggcgtctgca ttgcaacctc tggcccagga      300
gcaaccaact tggttacccc aatcgctgat gcaaacttgg actccgttcc catggttgcc      360
atcaccggcc aggtcggaag tggcctgctg gtaccgacg cttttccagga agccgatatc      420 cgcggcatca ccatgccagt gaccaagcac aacttcatgg tcaccgaccc caacgacatt      480
ccacaggcat tggctgaggc attccaccct gcgattactg gtcgccctgg ccctgttctg      540
gtggatattc ctaaggatgt ccagaacgct gaattggatt tcgtctggcc accaaagatc      600
gacctgccag gctaccgccc agtttcaaca ccacatgctc gccagatcga gcaggcagtc      660
aagctgatcg gtgaggccaa gaagcccgtc ctttacgttg gaggcggcgt tatcaaggct      720
```

```
gacgcacacg aagagcttcg tgcgttcgct gagtacaccg gcatcccagt tgtcaccacc    780
ttgatggctt tgggtacttt cccagagtct cacgagctgc acatgggtat gccaggcatg    840
catggcactg tgtccgctgt tggtgcactg cagcgcagcg acctgctgat tgctatcggc    900
tcccgctttg atgaccgcgt caccggtgac gttgacacct tcgcgcctga cgccaagatc    960
attcacgccg atattgatcc tgccgaaatc ggaaagatca agcaggttga ggttccaatc   1020
gtgggcgatg cccgcgaagt tcttgctcgt ctgctggaaa ccaccaaggc aagcaaggca   1080
gagaccgagg acatctccga gtgggttgac tacctcaagg gcctcaaggc acgtttccca   1140
cgtggctacg acgagcagcc aggcgatctg ctggcaccac agtttgtcat tgaaaccctg   1200
tccaaggaag ttggccccga cgcaatttac tgcgccggcg tcggacagca ccaaatgtgg   1260
gcagctcagt tcgttgactt tgaaaagcca cgcacctggc tcaactccgg tggactgggc   1320
accatgggct acgcagttcc tgcggccctt ggagcaaagg ctggcgcacc tgacaaggaa   1380
gtctgggcta tcgacggcga cggctgtttc cagatgacca accaggaact caccaccgcc   1440
gcagttgaag gtttccccat taagatcgca ctaatcaaca cggaaacct gggcatggtt    1500
cgccaatggc agaccctatt ctatgaagga cggtactcaa atactaaact tcgtaaccag   1560
ggcgagtaca tgcccgactt tgttgccctt tctgagggac ttggctgtgt tgccatccgc   1620
gtcaccaaag cggaggaagt actgccagcc atccaaaagg ctcgagaaat caacgaccgc   1680
ccagtagtca tcgacttcat cgtcggtgaa gacgcacagg tatggccaat ggtgtctgct   1740
ggatcatcca actccgatat ccagtacgca ctcggattgc gcccattctt tgacggcgac   1800
gaatcagctg cagaagaccc tgcagacatt catgcttccg ttgattcgac cgaggcataa   1860
ggagagaccc aagatggcta attctgacgt caccccgccac atcctgtccg tactcgttca   1920
ggacgtagac ggaatcattt cccgcgtatc aggtatgttc acccgacgcg cattcaacct   1980
cgtgtccctc gtgtctgcaa agaccgaaac acacggcatc aaccgcatca cggttgttgt   2040
cgacgccgac gagctcaaca ttgagcagat caccaagcag ctcaacaagc tgatcccggt   2100
gctcaaagtc gtgcgacttg atgaagagac cactatcgcc cgcgcaatca tgctggttaa   2160
ggtctctgcg gacagcacca accgtccgca gatcgtcgac gccgcgaaca tcttccgcgc   2220
ccgagtcgtc gacgtggctc cagactctgt ggttattgaa tccacaggca ccccaggcaa   2280
gctccgcgct ctgcttgatg tgatggaacc attcggaatc cgcgaactga tccaatccgg   2340
acagattgca ctcaaccgcg gtccgaagac catggctccg gccaagatct aaacagcaat   2400
taatctgatt gcacctgctg cataaatgtg actagtcaaa caccgtctaa ttacatgtgt   2460
gtggtagaac aataatgtag ttgtctgccc aaccgagtga cactcccacg atttacagtg   2520
ggggcagaca tcttttcacc aaaattttta cgaaaggcga gattttctcc catggctatt   2580
gaactgcttt atgatgctga cgctgacctc tccttgatcc agggccgtaa ggttgccatc   2640
gttggctacg gctcccaggg ccacgcacac tcccagaacc tccgcgattc tggcgttgag   2700
gttgtcattg gtctgcgcga gggctccaag tccgcagaga aggcaaagga agcaggcttc   2760
gaagtcaaga ccaccgctga ggctgcagct tgggctgacg tcatcatgct cctggctcca   2820
gacacctccc aggcagaaat cttccaccaa cgacatcgag caaacctgaa cgcaggcgac   2880
gcactgctgt tcggccacgg cctgaacatt cacttcgacc tgatcaagcc agctgacgac   2940
atcatcgttg gcatggttgc gccaaagggc ccaggccact tggttcgccg tcagttcgtt   3000
gatggcaagg gtgttccttg cctcatcgca gtcgaccagg acccaaccgg aaccgcacag   3060
```

```
gctctgaccc tgtcctacgc agcagcaatc ggtggcgcac gcgcaggcgt tatcccaacc    3120
accttcgaag ctgagaccgt caccgacctc ttcggcgagc aggctgttct ctgcggtggc    3180
accgaggaac tggtcaaggt tggcttcgag gttctcaccg aagctggcta cgagccagag    3240
atggcatact tcgaggttct tcacgagctc aagctcatcg ttgacctcat gttcgaaggt    3300
ggcatcagca acatgaacta ctctgtttct gacaccgctg agttcggtgg ctacctctcc    3360
ggcccacgcg tcatcgatgc agacaccaag tcccgcatga aggacatcct gaccgatatc    3420
caggacggca ccttcaccaa gcgcctcatc gcaaacgttg agaacggcaa caccgagctt    3480
gagggtcttc gtgcttccta caacaaccac ccaatcgagg agaccggcgc taagctccgc    3540
gacctcatga gctgggtcaa ggttgacgct cgcgcagaaa ccgcttaa              3588

<210> SEQ ID NO 35
<211> LENGTH: 1842
<212> TYPE: DNA
<213> ORGANISM: Corynebacterium glutamicum

<400> SEQUENCE: 35
atgatcccac ttcgttcaaa agtcaccacc gtcggtcgca atgcagctgg cgctcgcgcc      60
ctttggcgtg ccaccggcac caaggaaaat gagttcggca agccaattgt tgccatcgtg     120
aactcctaca cccagttcgt gcccggacac gttcaccttg agaacgtcgg cgatattgtg     180
gcagatgcag tgcgcaaagc cggtggcgtt ccaaaagaat caacaccat cgccgtcgat      240 gacggcatcg ccatgggaca cggcggcatg ctgtactccc tgccatcccg tgaaatcatc     300
gccgactccg tcgaatacat ggtcaacgca cacaccgccg acgccatggt gtgtatctcc     360
aactgtgaca agatcacccc aggcatgctc aacgcagcaa tgcgcctgaa catcccagtg     420
gtcttcgttt ccggtggccc aatggaagct ggcaaggctg tcgtcgttga cggcgttgca     480
cacgcaccaa ccgacctcat caccgcgatc tccgcatccg caagcgatgc agtcgacgac     540
gcaggccttg cagccgttga agcatccgca tgcccaacct gtggctcctg ctccggtatg     600
ttcaccgcga actccatgaa ctgcctcacc gaagctctgg actttctct cccaggcaac     660 ggctccaccc tggcaaccca cgcagcacgt cgcgcactgt ttgaaaaggc cggcgaaacc     720
gtcgttgaac tgtgccgccg ctactacggt gaagaagacg aatccgttct gccacgtggc     780
attgccacca agaaggcatt cgaaaacgca atggcactgg atatggccat gggtggatcc     840
accaacacca tcctccacat cctcgcagct gcccaggaag gcgaagttga cttcgacctc     900
gcagacatcg acgaactgtc caaaaacgtc cctgcctgt ccaaggttgc accaaactcc     960
gactaccaca tggaagacgt ccaccgcgcc ggtggcattc agcactgct cggcgagctc    1020 aaccgcggtg gcctgctgaa taaggacgtc cactccgttc actccaacga ccttgaaggt    1080
tggttggatg actgggatat ccgctctggc aagaccaccg aagtagcaac cgaactcttc    1140
cacgcagccc aggtggcat ccgcaccacc gaagcattct ccaccgagaa ccgctgggac    1200
gaactcgaca ccgacgctgc caagggctgc atccgcgacg ttgaacacgc ctacaccgcc    1260
gacggcggcc tggttgttct tcgcggcaac atctccctg acggcgcagt gatcaagtcc    1320
gcaggtatcg aagaagagct gtggaacttc accggaccag cacgagttgt cgaaagccag    1380
gaagaggcag tctctgtcat cctgaccaag accatccaag ctggcgaagt tctggtcgtc    1440
cgctacgaag gccatcagg tggaccaggc atgcaggaaa tgcttcaccc aaccgcattc    1500
ctcaagggat ccggcctggg caagaagtgt gcactgatca ccgacggccg tttctccgga    1560
ggttcctcag gactgtccat cggccacgtc tccccagaag cagcacacgg cggagtcatt    1620
```

```
ggtctgatcg aaaacggcga catcgtttcc atcgacgttc acaaccgcaa gctcgaagtt    1680
caggtctcca acgaggaact ccagcgccgc cgcgacgcta tgaacgcctc cgagaagcca    1740
tggcagccag tcaaccgtaa ccgcgttgtc accaaggcac tgcgcgcata cgcaaagatg    1800
gctacctccg ctgataaggg tgcagtccgt caggtcgact aa                      1842
```

<210> SEQ ID NO 36
<211> LENGTH: 33
<212> TYPE: DNA
<213> ORGANISM: Artificial Sequence
<220> FEATURE:
<223> OTHER INFORMATION: Synthetic Construct; Primer

<400> SEQUENCE: 36

```
gacccgggag taaaggagcc agaaagtcgt gaa                                  33
```

<210> SEQ ID NO 37
<211> LENGTH: 41
<212> TYPE: DNA
<213> ORGANISM: Artificial Sequence
<220> FEATURE:
<223> OTHER INFORMATION: Synthetic Construct; Primer

<400> SEQUENCE: 37

```
gacccgggcc tgcaggtgcc ttatgtacaa agtgcacagc a                         41
```

<210> SEQ ID NO 38
<211> LENGTH: 30
<212> TYPE: DNA
<213> ORGANISM: Artificial Sequence
<220> FEATURE:
<223> OTHER INFORMATION: Synthetic Construct; Primer

<400> SEQUENCE: 38

```
ctcttcatga tcccacttcg ttcaaaagtc                                      30
```

<210> SEQ ID NO 39
<211> LENGTH: 28
<212> TYPE: DNA
<213> ORGANISM: Artificial Sequence
<220> FEATURE:
<223> OTHER INFORMATION: Synthetic Construct; Primer

<400> SEQUENCE: 39

```
ctcttcatga ttagtcgacc tgacggac                                        28
```

<210> SEQ ID NO 40
<211> LENGTH: 1011
<212> TYPE: DNA
<213> ORGANISM: Escherichia coli

<400> SEQUENCE: 40

```
atgaaggctg cagttgttac gaaggatcat catgttgacg ttacgtataa aacactgcgc     60
tcactgaaac atggcgaagc cctgctgaaa atggagtgtt gtggtgtatg tcataccgat    120
cttcatgtta agaatggcga ttttggtgac aaaaccggcg taattctggg ccatgaaggc    180
atcggtgtgg tggcagaagt gggtccaggt gtcacctcat aaaaccagg cgatcgtgcc    240 agcgtggcgt ggttctacga aggatgcggt cattgcgaat actgtaacag tggtaacgaa    300 acgtctctgcc gttcagttaa aaatgccgga tacagcgttg atggcgggat ggcggaagag    360
tgcatcgtgg tcgccgatta cgcggtaaaa gtgccagatg gtctggactc ggcggcggcc    420
```

| | |
|---|---|
| agcagcatta cctgtgcggg agtcaccacc tacaaagccg ttaagctgtc aaaaattcgt | 480 |
| ccagggcagt ggattgctat ctacggtctt ggcggtctgg gtaacctcgc cctgcaatac | 540 |
| gcgaagaatg tctttaacgc caaagtgatc gccattgatg tcaatgatga gcagttaaaa | 600 |
| ctggcaaccg aaatgggcgc agatttagcg attaactcac acaccgaaga cgccgccaaa | 660 |
| attgtgcagg agaaaactgg tggcgctcac gctgcggtgg taacagcggt agctaaagct | 720 |
| gcgtttaact cggcagttga tgctgtccgt gcaggcggtc gtgttgtggc tgtcggtcta | 780 |
| ccgccggagt ctatgagcct ggatatccca cgtcttgtgc tggatggtat tgaagtggtc | 840 |
| ggttcgctgg tcggcacgcg ccaggattta actgaagcct tccagtttgc cgccgaaggt | 900 |
| aaagtggtgc cgaaagtcgc cctgcgtccg ttagcggaca tcaacaccat ctttactgag | 960 |
| atggaagaag gcaaaatccg tggccgcatg gtgattgatt ccgtcacta a | 1011 |

<210> SEQ ID NO 41
<211> LENGTH: 30
<212> TYPE: DNA
<213> ORGANISM: Artificial Sequence
<220> FEATURE:
<223> OTHER INFORMATION: Synthetic Construct; Primer

<400> SEQUENCE: 41

| | |
|---|---|
| ctctccatgg aggctgcagt tgttacgaag | 30 |

<210> SEQ ID NO 42
<211> LENGTH: 40
<212> TYPE: DNA
<213> ORGANISM: Artificial Sequence
<220> FEATURE:
<223> OTHER INFORMATION: Synthetic Construct; Primer

<400> SEQUENCE: 42

| | |
|---|---|
| ctctccatgg agatctttag tgacggaaat caatcaccat | 40 |

<210> SEQ ID NO 43
<211> LENGTH: 1647
<212> TYPE: DNA
<213> ORGANISM: Lactococcus lactis

<400> SEQUENCE: 43

| | |
|---|---|
| atggatacag taggagatta cctattagac cgattacacg agttaggaat tgaagaaatt | 60 |
| tttggagtcc ctggagacta taacttacaa tttttagatc aaattatttc ccgcaaggat | 120 |
| atgaaatggg tcggaaatgc taatgaatta aatgcttcat atatggctga tggctatgct | 180 |
| cgtactaaaa aagctgccgc atttcttaca acctttggag taggtgaatt gagtgcagtt | 240 |
| aatggattag caggaagtta cgccgaaaat ttaccagtag tagaaatagt gggatcacct | 300 |
| acatcaaaag ttcaaaatga aggaaaattt gttcatcata cgctggctga cggtgatttt | 360 |
| aaacacttta tgaaaatgca cgaacctgtt acagcagctc gaactttact gacagcagaa | 420 |
| aatgcaaccg ttgaaattga ccgagtactt tctgcactat aaaagaaag aaaacctgtc | 480 |
| tatatcaact taccagttga tgttgctgct gcaaaagcag agaaaccctc actcccttg | 540 |
| aaaaagaaa actcaacttc aaatacaagt gaccaagaga tcttgaacaa aattcaagaa | 600 |
| agcttgaaaa atgccaaaaa accaatcgtg attacaggac atgaaataat tagttttggc | 660 |
| ttagaaaaaa cagtctctca atttattca aagacaaaac tacctattac gacattaaac | 720 |
| tttgaaaaaa gttcagttga tgaagctctc ccttcatttt taggaatcta taatggtaaa | 780 |
| ctctcagagc ctaatcttaa agaattcgtg gaatcagccg acttcatcct gatgcttgga | 840 |

```
gttaaactca cagactcttc aacaggagcc ttcactcatc atttaaatga aaataaaatg      900
atttcactga atatagatga aggaaaaata tttaacgaaa gcatccaaaa ttttgatttt      960
gaatccctca tctcctctct cttagaccta agcgaaatag aatacaaagg aaaatatatc     1020
gataaaaagc aagaagactt tgttccatca aatgcgcttt tatcacaaga ccgcctatgg     1080
caagcagttg aaaacctaac tcaaagcaat gaaacaatcg ttgctgaaca agggacatca     1140
ttctttggcg cttcatcaat tttcttaaaa ccaaagagtc attttattgg tcaacccttg     1200
tggggatcaa ttggatatac attcccagca gcattaggaa gccaaattgc agataaagaa     1260
agcagacacc ttttatttat tggtgatggt tcacttcaac ttacggtgca agaattagga     1320
ttagcaatca gagaaaaaat taatccaatt tgctttatta tcaataatga tggttataca     1380
gtcgaaagag aaattcatgg accaaatcaa agctacaatg atattccaat gtggaattac     1440
tcaaaattac cagaatcatt tggagcaaca gaagaacgag tagtctcgaa aatcgttaga     1500
actgaaaatg aatttgtgtc tgtcatgaaa gaagctcaag cagatccaaa tagaatgtac     1560
tggattgagt taattttggc aaaagaagat gcaccaaaag tactgaaaaa aatgggcaaa     1620
ctatttgctg aacaaaataa atcataa                                        1647
```

<210> SEQ ID NO 44
<211> LENGTH: 36
<212> TYPE: DNA
<213> ORGANISM: Artificial Sequence
<220> FEATURE:
<223> OTHER INFORMATION: Synthetic Construct; Primer

<400> SEQUENCE: 44

```
ctctccatgg atacagtagg agattaccta ttagac                                 36
```

<210> SEQ ID NO 45
<211> LENGTH: 49
<212> TYPE: DNA
<213> ORGANISM: Artificial Sequence
<220> FEATURE:
<223> OTHER INFORMATION: Synthetic Construct; Primer

<400> SEQUENCE: 45

```
ctctccatgg agatctttat gatttatttt gttcagcaaa tagtttgcc                   49
```

<210> SEQ ID NO 46
<211> LENGTH: 1011
<212> TYPE: DNA
<213> ORGANISM: Pseudomonas putida

<400> SEQUENCE: 46

```
atgaaagctg ctgtcgttgc accaggccgt cgcgtggacg tggtagagaa aaccctgcgc       60
cctctcgaat acggcgaagc gctgctgaag atgcagtgct gcggtgtgtg ccacaccgac      120
ctgcacgtga aaaatggcga ctttggtgac aagaccggtg tagtactggg ccacgaaggt      180
attggcgtgg ttcaggaagt tggcccgggc gtcacctcgc tcaagccagg cgaccgtgcc      240
agcgtcgcct ggttctacca gggttgcgga cattgcgaat actgcaacag cggcaacgag      300
accctgtgcc gcgacgtgaa gaattccggt tacaccgtgg acggcggcat ggccgaggcc      360
tgcatcgtca aggccgacta tcggttaaaa gtgcccgacg gcctcgactc cgctgccgcc      420
agcagcatca cctgcgccgg cgtcacgacc tacaaggcga tgaaaatctc caacgtccgc      480
cccggccaat ggatcgccat ctacgggctc ggcggcctgg gcaacctggc cctgcaatat      540
```

```
gccaagaacg tgttcaacgc caaagtcatc gccatcgacg tcaacgaaga gcaactgcgc    600
ttcgccagcg agatgggcgc ggacctggtg gtcaacccgc tcaacgaaga cgccgcgaag    660
gtcatccagg ccaagaccgg tggcgcacat gctgccgtcg ttactgctgt ggccaaaggc    720
gcgttcaact cagccgtcga tgccttgcgc gctggcgggc gactggtggc cgtcgggctt    780
ccgtcggagt ccatggacct gaatattcct cgcctggtgc ttgatgggat cgaagtggtg    840
ggctcgctgg taggtacacg ccaggacctg caggaagcct tccagtttgc cgctgaaggc    900
aaagtggtgc ccaaggtaac gctgcgaccg atcgaggata tcaaccagat ctttgacgag    960
atgctggagg gcaagatcaa aggccggatg gtgatacagt tcgaaggctg a            1011

<210> SEQ ID NO 47
<211> LENGTH: 26
<212> TYPE: DNA
<213> ORGANISM: Artificial Sequence
<220> FEATURE:
<223> OTHER INFORMATION: Synthetic Construct; Primer

<400> SEQUENCE: 47
ctcttcatga aagctgctgt cgttgc                                          26

<210> SEQ ID NO 48
<211> LENGTH: 37
<212> TYPE: DNA
<213> ORGANISM: Artificial Sequence
<220> FEATURE:
<223> OTHER INFORMATION: Synthetic Construct; Primer

<400> SEQUENCE: 48
ctcttcatga ctcgagtcag ccttcgaact gtatcac                              37

<210> SEQ ID NO 49
<211> LENGTH: 1047
<212> TYPE: DNA
<213> ORGANISM: Saccharomyces cerevisiae

<400> SEQUENCE: 49
atggctattc cagaaactca aaaagccatt atcttctacg aatccaacgg caagttggag     60
cataaggata tcccagttcc aaagccaaag cccaacgaat tgttaatcaa cgtcaagtac    120
tctggtgtct gccacaccga tttgcacgct tggcatggtg actggccatt gccaactaag    180
ttaccattag ttggtgggca cgaaggtgcc ggtgtcgttg tcggcatggg tgaaaacgtt    240
aagggctgga gatcggtga ctacgccggt atcaaatggt tgaacggttc ttgtatggcc    300
tgtgaatact gtgaattggg taacgaatcc aactgtcctc acgctgactt gtctggttac    360
acccacgacg gttcttttcca agaatacgct accgctgacg ctgttcaagc cgctcacatt    420
cctcaaggta ctgacttggc ccaagtcgcg ccaatcttgt gtgctggtat caccgtatac    480
aaggctttga gtctgccaa cttgagagca ggccactggg tggccatttc tggtgctgct    540
ggtggtctag gttctttggc tgttcaatat gctaaggcga tgggttacag agtcttaggt    600
attgatggtg gtccaggaaa ggaagaattg tttacctcgc tcggtggtga agtattcatc    660
gacttcacca agagaaggga cattgttagc gcagtcgtta aggctaccaa cggcggtgcc    720
cacggtatca tcaatgtttc cgtttccgaa gccgctatcg aagcttctac cagatactgt    780
agggcgaacg gtactgttgt cttggttggt ttgccagccg gtgcaaagtg ctcctctgat    840
gtcttcaacc acgttgtcaa gtctatctcc attgtcggct cttacgtggg gaacagagct    900
gataccagag aagccttaga tttctttgcc agaggtctag tcaagtctcc aataaaggta    960
```

```
gttggcttat ccagtttacc agaaatttac gaaaagatgg agaagggcca aattgctggt    1020
agatacgttg ttgacacttc taaataa                                        1047

<210> SEQ ID NO 50
<211> LENGTH: 38
<212> TYPE: DNA
<213> ORGANISM: Artificial Sequence
<220> FEATURE:
<223> OTHER INFORMATION: Synthetic Construct; Primer

<400> SEQUENCE: 50
ctctccatgg ctattccaga aactcaaaaa gccattat                              38

<210> SEQ ID NO 51
<211> LENGTH: 45
<212> TYPE: DNA
<213> ORGANISM: Artificial Sequence
<220> FEATURE:
<223> OTHER INFORMATION: Synthetic Construct; Primer

<400> SEQUENCE: 51
ctctccatgg agatctttat ttagaagtgt caacaacgta tctac                      45

<210> SEQ ID NO 52
<211> LENGTH: 1650
<212> TYPE: DNA
<213> ORGANISM: Staphylococcus epidermidis

<400> SEQUENCE: 52
atgaaacaac gcgtaggaca atatttaatg gacgcggttt attcagcagg tgctgacaaa      60 gttttttggtg tcccaggaga ttttaatcta gcctttttag acgatattat tgcacataat    120
gatattaaat ggattggtaa tacaaatgag cttaatgcaa gttatgctgc cgacggatat    180
gcacgtatta atggcatagg tgcaatggta acaacatttg gagtgggtga attaagtgct    240
gtcaacggaa tcgctggatc ttatgctgag cgtgtgccag ttattgccat cactggggca    300
cctactcgag ctgtagaaca agaaggcaaa tacgttcacc attcccttgg cgaaggaact    360
tttgatgatt atagaaaaat gtttgagcct attacaacag cgcaagctta tattacacct    420
gataatgcta ccacagaaat tccaagagta atcaatacgg cgcttcaaca acgtcgtcca    480
gttcacattc atttacctat tgatgtcgca ctaacagaga ttgaaatttc aaacccattc    540
aaaccagaag tcgaaccaca aaaaaacgtt caaagttata tcaatatggt tcaagacaaa    600
cttgaatcgg catcacaacc tgtcattatt acaggacatg aaataaatag tttccatctg    660
cataaagaac tcgaacaatt cgttaatcaa actcaaattc cagttgttca gttatcttta    720
ggtaaaggtg catttaatga agaaaatcct tattatatgg gtatctttga tggttcaata    780
gcagaacaag atattcaaga ttatgttaat caaagtgatg ctattttgaa tattggtgct    840
aaattaacag attctgcaac agctgggttc tcatatcaat ttgatattaa tgaagtgatt    900
atgctaaatc ataatgaatt taaaattaat gatacatgca tcgaagcatt ttcattacca    960
aatatattaa atggttttaaa taagtatatt cactacaaaa acactaatga tttcccacaa    1020
tatgagagac cacaatcaca caattacgaa cttagtgatc agccattaac tcaagagact    1080
tatttcaata tgatgcaaga ttttttacaa caagatgata ttttaatcgc tgaacaaggt    1140
acatcattct ttggtgctta tgacttagcc ttgtacaaag ataatacttt tatcgggcaa    1200
ccattatggg gatctatcgg ctatacacta ccagcaacgc taggaacaca aattgcaaat    1260
```

```
ccatatcgtc gaaacattct attaattggt gatggatcac tacaattaac tgttcaatca    1320
ttatctacaa tgattcgtca aaatttaaac cctgtgatat ttgtaattaa taacgatggt    1380
tatacagttg agagaatgat tcatggtatg aaagaacctt acaatgacat tcgcatgtgg    1440
gattacaaat cattaccttc tgtatttggt ggtgacaatg ttttagttca tgatgtaaac    1500
acttcagaag aactcatgct caccttcgaa aatattaaat ctaatagtga tcgcatgcac    1560
tttgtagaag tgaaaatggc tgttgaagat gcaccagtta aattaagtaa tatagctaaa    1620
gcattcgcat cacaaaacaa atcatcttaa                                     1650
```

<210> SEQ ID NO 53
<211> LENGTH: 36
<212> TYPE: DNA
<213> ORGANISM: Artificial Sequence
<220> FEATURE:
<223> OTHER INFORMATION: Synthetic Construct; Primer
<400> SEQUENCE: 53

```
ctctccatgg aacaacgcgt aggacaatat ttaatg                                36
```

<210> SEQ ID NO 54
<211> LENGTH: 45
<212> TYPE: DNA
<213> ORGANISM: Artificial Sequence
<220> FEATURE:
<223> OTHER INFORMATION: Synthetic Construct; Primer
<400> SEQUENCE: 54

```
ctctccatgg agatctttaa gatgatttgt tttgtgatgc gaatg                      45
```

<210> SEQ ID NO 55
<211> LENGTH: 3913
<212> TYPE: DNA
<213> ORGANISM: Artificial Sequence
<220> FEATURE:
<223> OTHER INFORMATION: Synthetic Construct; Ptac-ilvB-ilvN-ilvC
<400> SEQUENCE: 55

```
ttcggctgtg caggtcgtaa atcactgcat aattcgtgtc gctcaaggcg cactcccgtt      60
ctggataatg ttttttgcgc cgacatcata acggttctgg caaatattct gaaatgagct     120
gttgacaatt aatcatcggc tcgtataatg tgtggaattg tgagcggata acaatttcac     180
acaggaaaca gaattcccgg gagtaaagga gccagaaagt cgtgaatgtg cagcttctc     240 aacagcccac tcccgccacg gttgcaagcc gtggtcgatc cgccgcccct gagcggatga     300
caggtgcaca ggcaattgtt cgatcgctcg aggagcttaa cgccgacatc gtgttcggta     360
ttcctggtgg tgcggtgcta ccggtgtatg acccgctcta ttcctccaca aaggtgcgcc     420
acgtcttggt gcgccacgag cagggcgcag gccacgcagc aaccggctac gcgcaggtta     480
ctggacgcgt tggcgtctgc attgcaacct ctggcccagg agcaaccaac ttggttaccc     540
caatcgctga tgcaaacttg gactccgttc ccatggttgc catcaccggc caggtcggaa     600
gtggcctgct gggtaccgac gctttccagg aagccgatat ccgcggcatc accatgccag     660
tgaccaagca caacttcatg gtcaccgacc caacgacat tccacaggca ttggctgagg     720
cattccacct cgcgattact ggtcgccctg gccctgttct ggtggatatt cctaaggatg     780
tccagaacgc tgaattggat ttcgtctggc caccaaagat cgacctgcca ggctaccgcc     840
cagtttcaac accacatgct cgccagatcg agcaggcagt caagctgatc ggtgaggcca     900
agaagcccgt cctttacgtt ggaggcggcg ttatcaaggc tgacgcacac gaagagcttc     960
```

```
gtgcgttcgc tgagtacacc ggcatcccag ttgtcaccac cttgatggct ttgggtactt    1020
tcccagagtc tcacgagctg cacatgggta tgccaggcat gcatggcact gtgtccgctg    1080
ttggtgcact gcagcgcagc gacctgctga ttgctatcgg ctcccgcttt gatgaccgcg    1140
tcaccggtga cgttgacacc ttcgcgcctg acgccaagat cattcacgcc gatattgatc    1200
ctgccgaaat cggaaagatc aagcaggttg aggttccaat cgtgggcgat gcccgcgaag    1260
ttcttgctcg tctgctggaa accaccaagg caagcaaggc agagaccgag gacatctccg    1320
agtgggttga ctacctcaag ggcctcaagg cacgtttccc acgtggctac gacgagcagc    1380
caggcgatct gctggcacca cagtttgtca ttgaaaccct gtccaaggaa gttggccccg    1440 acgcaatttta ctgcgccggc gtcggacagc accaaatgtg gcagctcag ttcgttgact    1500 ttgaaaagcc acgcacctgg ctcaactccg gtggactggg caccatgggc tacgcagttc    1560
ctgcggccct tggagcaaag gctggcgcac ctgacaagga agtctgggct atcgacggcg    1620
acggctgttt ccagatgacc aaccaggaac tcaccaccgc cgcagttgaa ggtttcccca    1680
ttaagatcgc actaatcaac aacggaaacc tgggcatggt tcgccaatgg cagaccctat    1740
tctatgaagg acggtactca aatactaaac ttcgtaacca gggcgagtac atgcccgact    1800
tgttgcccct ttctgaggga cttggctgtg ttgccatccg cgtcaccaaa gcggaggaag    1860
tactgccagc catccaaaag gctcgagaaa tcaacgaccg cccagtagtc atcgacttca    1920
tcgtcggtga agacgcacag gtatggccaa tggtgtctgc tggatcatcc aactccgata    1980
tccagtacgc actcggattg cgcccattct ttgacggcga cgaatcagct gcagaagacc    2040
ctgcagacat tcatgcttcc gttgattcga ccgaggcata aggagagacc caagatggct    2100
aattctgacg tcacccgcca catcctgtcc gtactcgttc aggacgtaga cggaatcatt    2160
tcccgcgtat caggtatgtt cacccgacgc gcattcaacc tcgtgtccct cgtgtctgca    2220
aagaccgaaa cacacggcat caaccgcatc acggttgttg tcgacgccga cgagctcaac    2280
attgagcaga tcaccaagca gctcaacaag ctgatcccgg tgctcaaagt cgtgcgactt    2340
gatgaagaga ccactatcgc ccgcgcaatc atgctggtta aggtctctgc ggacagcacc    2400
aaccgtccgc agatcgtcga cgccgcgaac atcttccgcg cccgagtcgt cgacgtggct    2460
ccagactctg tggttattga atccacaggc accccaggca agctccgcgc tctgcttgat    2520
gtgatggaac cattccggaat ccgcgaactg atccaatccg gacagattgc actcaaccgc    2580
ggtccgaaga ccatggctcc ggccaagatc taaacagcaa ttaatctgat tgcacctgct    2640
gcataaatgt gactagtcaa acaccgtcta attacatgtg tgtggtagaa caataatgta    2700
gttgtctgcc caaccgagtg acactcccac gatttacagt gggggcagac atcttttcac    2760
caaaattttt acgaaaggcg agattttctc ccatggctat tgaactgctt tatgatgctg    2820
acgctgacct ctccttgatc cagggccgta aggttgccat cgttggctac ggctcccagg    2880
gccacgcaca ctcccagaac ctccgcgatt ctggcgttga ggttgtcatt ggtctgcgcg    2940
agggctccaa gtccgcagag aaggcaaagg aagcaggctt cgaagtcaag accaccgctg    3000
aggctgcagc ttgggctgac gtcatcatgc tcctggctcc agacacctcc caggcagaaa    3060
tcttcaccaa cgacatcgag ccaaacctga acgcaggcga cgcactgctg ttcggccacg    3120
gcctgaacat tcacttcgac ctgatcaagc cagctgacga catcatcgtt ggcatggttg    3180
cgccaaaggg cccaggccac ttggttcgcc gtcagttcgt tgatggcaag ggtgttcctt    3240
gcctcatcgc agtcgaccag gacccaaccg gaaccgcaca ggctctgacc ctgtcctacg    3300
```

-continued

```
cagcagcaat cggtggcgca cgcgcaggcg ttatcccaac caccttcgaa gctgagaccg    3360
tcaccgacct cttcggcgag caggctgttc tctgcggtgg caccgaggaa ctggtcaagg    3420
ttggcttcga ggttctcacc gaagctggct acgagccaga gatggcatac ttcgaggttc    3480
ttcacgagct caagctcatc gttgacctca tgttcgaagg tggcatcagc aacatgaact    3540
actctgtttc tgacaccgct gagttcggtg gctacctctc cggcccacgc gtcatcgatg    3600
cagacaccaa gtcccgcatg aaggacatcc tgaccgatat ccaggacggc accttcacca    3660
agcgcctcat cgcaaacgtt gagaacggca caccgagct tgagggtctt cgtgcttcct    3720
acaacaacca cccaatcgag gagaccggcg ctaagctccg cgacctcatg agctgggtca    3780
aggttgacgc tcgcgcagaa accgcttaag tttcaccct ttgacggctt aaccgccgca    3840
taggaaatgc cctccggact aattgtctgg agggcatttt tgctacctgc tgtgcacttt    3900
gtacataagc gaa                                                       3913
```

<210> SEQ ID NO 56
<211> LENGTH: 30
<212> TYPE: DNA
<213> ORGANISM: Artificial Sequence
<220> FEATURE:
<223> OTHER INFORMATION: Synthetic Construct; Primer

<400> SEQUENCE: 56

```
atgcaagctt cggctgtgca ggtcgtaaat                                       30
```

<210> SEQ ID NO 57
<211> LENGTH: 30
<212> TYPE: DNA
<213> ORGANISM: Artificial Sequence
<220> FEATURE:
<223> OTHER INFORMATION: Synthetic Construct; Primer

<400> SEQUENCE: 57

```
acgcaagctt cgcttatgta caaagtgcac                                       30
```

<210> SEQ ID NO 58
<211> LENGTH: 1716
<212> TYPE: DNA
<213> ORGANISM: Bacillus subtilis

<400> SEQUENCE: 58

```
gtgttgacaa aagcaacaaa agaacaaaaa tcccttgtga aaaacagagg ggcggagctt      60
gttgttgatt gcttagtgga gcaaggtgtc acacatgtat ttggcattcc aggtgcaaaa     120
attgatgcgg tatttgacgc tttacaagat aaaggacctg aaattatcgt tgcccggcac     180
gaacaaaacg cagcattcat ggcccaagca gtcggccgtt taactggaaa accgggagtc     240
gtgttagtca catcaggacc gggtgcctct aacttggcaa caggcctgct gacagcgaac     300
actgaaggag accctgtcgt tgcgcttgct ggaaacgtga tccgtgcaga tcgtttaaaa     360
cggacacatc aatctttgga taatgcggcg ctattccagc cgattacaaa atacagtgta     420
gaagttcaag atgtaaaaaa tataccggaa gctgttacaa atgcatttag atagcgtca     480 gcagggcagg ctgggccgc ttttgtgagc tttccgcaag atgttgtgaa tgaagtcaca     540
aatacgaaaa acgtgcgtgc tgttcagcg ccaaaactcg gtcctgcagc agatgatgca     600
atcagtgcgg ccatagcaaa aatccaaaca gcaaaacttc ctgtcgtttt ggtcggcatg     660
aaaggcggaa gaccggaagc aattaaagcg gttcgcaagc ttttgaaaaa ggttcagctt     720
ccatttgttg aaacatatca agctgccggt acccctttcta gagatttaga ggatcaatat     780
```

```
tttggccgta tcggtttgtt ccgcaaccag cctggcgatt tactgctaga gcaggcagat      840
gttgttctga cgatcggcta tgacccgatt gaatatgatc cgaaattctg gaatatcaat      900
ggagaccgga caattatcca tttagacgag attatcgctg acattgatca tgcttaccag      960
cctgatcttg aattgatcgg tgacattccg tccacgatca atcatatcga acacgatgct     1020
gtgaaagtgg aatttgcaga gcgtgagcag aaaatccttt ctgatttaaa acaatatatg     1080
catgaaggtg agcaggtgcc tgcagattgg aaatcagaca gagcgcaccc tcttgaaatc     1140
gttaaagagt tgcgtaatgc agtcgatgat catgttacag taacttgcga tatcggttcg     1200
cacgccattt ggatgtcacg ttatttccgc agctacgagc cgttaacatt aatgatcagt     1260
aacggtatgc aaacactcgg cgttgcgctt ccttgggcaa tcggcgcttc attggtgaaa     1320
ccgggagaaa aagtggtttc tgtctctggt gacggcggtt tcttattctc agcaatggaa     1380
ttagagacag cagttcgact aaaagcacca attgtacaca ttgtatggaa cgacagcaca     1440
tatgacatgt tgcattcca gcaattgaaa aaatataacc gtacatctgc ggtcgatttc      1500
ggaaatatcg atatcgtgaa atatgcggaa agcttcggag caactggctt gcgcgtagaa     1560
tcaccagacc agctggcaga tgttctgcgt caaggcatga acgctgaagg tcctgtcatc     1620
atcgatgtcc cggttgacta cagtgataac attaatttag caagtgacaa gcttccgaaa     1680
gaattcgggg aactcatgaa aacgaaagct ctctag                               1716

<210> SEQ ID NO 59
<211> LENGTH: 63
<212> TYPE: DNA
<213> ORGANISM: Artificial Sequence
<220> FEATURE:
<223> OTHER INFORMATION: Synthetic Construct; Primer

<400> SEQUENCE: 59
ctctcccggg aaacttttta gaaaggtgtg tttcacccgt gttgacaaaa gcaacaaaag       60
aac                                                                    63

<210> SEQ ID NO 60
<211> LENGTH: 39
<212> TYPE: DNA
<213> ORGANISM: Artificial Sequence
<220> FEATURE:
<223> OTHER INFORMATION: Synthetic Construct; Primer

<400> SEQUENCE: 60
ctctcccggg agatctctag agagctttcg ttttcatga                             39

<210> SEQ ID NO 61
<211> LENGTH: 1017
<212> TYPE: DNA
<213> ORGANISM: Corynebacterium glutamicum

<400> SEQUENCE: 61
atggctattg aactgctttta tgatgctgac gctgacctct ccttgatcca gggccgtaag      60
gttgccatcg ttggctacgg ctcccagggc cacgcacact cccagaacct ccgcgattct     120
ggcgttgagg ttgtcattgg tctgcgcgag ggctccaagt ccgcagagaa ggcaaaggaa     180
gcaggcttcg aagtcaagac caccgctgag gctgcagctt gggctgacgt catcatgctc     240
ctggctccag acacctccca ggcagaaatc ttcaccaacg acatcgagcc aaaacctgaac    300 gcaggcgacg cactgctgtt cggccacggc ctgaacattc acttcgacct gatcaagcca     360
```

```
gctgacgaca tcatcgttgg catggttgcg ccaaagggcc caggccactt ggttcgccgt      420
cagttcgttg atggcaaggg tgttccttgc ctcatcgcag tcgaccagga cccaaccgga      480
accgcacagg ctctgaccct gtcctacgca gcagcaatcg gtggcgcacg cgcaggcgtt      540
atcccaacca ccttcgaagc tgagaccgtc accgacctct cggcgagca ggctgttctc       600 tgcggtggca ccgaggaact ggtcaaggtt ggcttcgagg ttctcaccga agctggctac      660
gagccagaga tggcatactt cgaggttctt cacgagctca agctcatcgt tgacctcatg      720
ttcgaaggtg gcatcagcaa catgaactac tctgtttctg acaccgctga gttcggtggc      780
tacctctccg gcccacgcgt catcgatgca gacaccaagt cccgcatgaa ggacatcctg      840
accgatatcc aggacggcac cttcaccaag cgcctcatcg caaacgttga aacggcaac      900 accgagcttg agggtcttcg tgcttcctac aacaaccacc caatcgagga gaccggcgct      960
aagctccgcg acctcatgag ctgggtcaag gttgacgctc gcgcagaaac cgcttaa      1017

<210> SEQ ID NO 62
<211> LENGTH: 1842
<212> TYPE: DNA
<213> ORGANISM: Corynebacterium glutamicum

<400> SEQUENCE: 62
atgatcccac ttcgttcaaa agtcaccacc gtcggtcgca atgcagctgg cgctcgcgcc       60
ctttggcgtg ccaccggcac caaggaaaat gagttcggca agccaattgt tgccatcgtg      120
aactcctaca cccagttcgt gcccggacac gttcaccta agaacgtcgg cgatattgtg       180
gcagatgcag tgcgcaaagc cggtggcgtt ccaaaagaat caacaccat cgccgtcgat       240 gacggcatcg ccatgggaca cggcggcatg ctgtactccc tgccatcccg tgaaatcatc      300
gccgactccg tcgaatacat ggtcaacgca cacaccgccg acgccatggt gtgtatctcc      360
aactgtgaca agatcacccc aggcatgctc aacgcagcaa tgcgcctgaa catcccagtg      420
gtcttcgttt ccggtggccc aatggaagct ggcaaggctg tcgtcgttga cggcgttgca      480
cacgcaccaa ccgacctcat caccgcgatc tccgcatccg caagcgatgc agtcgacgac      540
gcaggccttg cagccgttga agcatccgca tgcccaacct gtggctcctg ctccggtatg      600
ttcaccgcga actccatgaa ctgcctcacc gaagctctgg acttttctct cccaggcaac      660
ggctccaccc tggcaaccca cgcagcacgt gcgcgcactgt ttgaaaaggc cggcgaaacc      720
gtcgttgaac tgtgccgccg ctactacggt gaagaagacg aatccgttct gccacgtggc      780
attgccacca agaaggcatt cgaaaacgca atggcactgg atatggccat gggtggatcc      840
accaacacca tcctccacat cctcgcagct gcccaggaag gcgaagttga cttcgacctc      900
gcagacatcg acgaactgtc caaaaacgtc ccctgcctgt ccaaggttgc accaaactcc      960
gactaccaca tggaagacgt ccaccgcgcc ggtggcattc agcactgct cggcgagctc     1020 aaccgcggtg gcctgctgaa taaggacgtc cactccgttc actccaacga ccttgaaggt     1080
tggttggatg actgggatat ccgctctggc aagaccaccg aagtagcaac cgaactcttc     1140
cacgcagccc aggtggcat ccgcaccacc gaagcattct ccaccgagaa ccgctgggac      1200
gaactcgaca ccgacgctgc caagggctgc atccgcgacg ttgaacacgc ctacaccgcc     1260
gacggcggcc tggttgttct tcgcggcaac atctcccctg acggcgcagt gatcaagtcc     1320
gcaggtatcg aagaagagct gtggaacttc accggaccag cacgagttgt cgaaagccag     1380
gaagaggcag tctctgtcat cctgaccaag accatccaag ctggcgaagt tctggtcgtc     1440
cgctacgaag gccatcagg tggaccaggc atgcaggaaa tgcttcaccc aaccgcattc     1500
```

```
ctcaagggat ccggcctggg caagaagtgt gcactgatca ccgacggccg tttctccgga    1560
ggttcctcag gactgtccat cggccacgtc tccccagaag cagcacacgg cggagtcatt    1620
ggtctgatcg aaaacggcga catcgtttcc atcgacgttc acaaccgcaa gctcgaagtt    1680
caggtctcca acgaggaact ccagcgccgc gcgacgcta tgaacgcctc cgagaagcca     1740
tggcagccag tcaaccgtaa ccgcgttgtc accaaggcac tgcgcgcata cgcaaagatg    1800
gctacctccg ctgataaggg tgcagtccgt caggtcgact aa                       1842
```

<210> SEQ ID NO 63
<211> LENGTH: 31
<212> TYPE: DNA
<213> ORGANISM: Artificial Sequence
<220> FEATURE:
<223> OTHER INFORMATION: Synthetic Construct; Primer

<400> SEQUENCE: 63

```
ctctccatgg ctattgaact gctttatgat g                                   31
```

<210> SEQ ID NO 64
<211> LENGTH: 35
<212> TYPE: DNA
<213> ORGANISM: Artificial Sequence
<220> FEATURE:
<223> OTHER INFORMATION: Synthetic Construct; Primer

<400> SEQUENCE: 64

```
ctctccatgg agatctttaa gcggtttctg cgcga                               35
```

<210> SEQ ID NO 65
<211> LENGTH: 33
<212> TYPE: DNA
<213> ORGANISM: Artificial Sequence
<220> FEATURE:
<223> OTHER INFORMATION: Synthetic Construct; Primer

<400> SEQUENCE: 65

```
gacccgggga gcagatttga aaagcgcatc atg                                 33
```

<210> SEQ ID NO 66
<211> LENGTH: 39
<212> TYPE: DNA
<213> ORGANISM: Artificial Sequence
<220> FEATURE:
<223> OTHER INFORMATION: Synthetic Construct; Primer

<400> SEQUENCE: 66

```
gacccggggg taccgtattt gcaacgggga gctccacca                           39
```

<210> SEQ ID NO 67
<211> LENGTH: 1983
<212> TYPE: DNA
<213> ORGANISM: Escherichia coli

<400> SEQUENCE: 67

```
atggcaagtt cgggcacaac atcgacgcgt aagcgcttta ccggcgcaga atttatcgtt    60
catttcctgg aacagcaggg cattaagatt gtgacaggca ttccgggcgg ttctatcctg    120
cctgtttacg atgccttaag ccaaagcacg caaatccgcc atattctggc ccgtcatgaa    180
cagggcgcgg gctttatcgc tcagggaatg cgcgcaccg acggtaaacc ggcggtctgt    240
atggcctgta gcgaccgggt gcgactaac ctggtgaccg ccattgccga tgcgcggctg    300
```

```
gactccatcc cgctgatttg catcactggt caggttcccg cctcgatgat cggcaccgac    360
gccttccagg aagtggacac ctacggcatc tctatcccca tcaccaaaca caactatctg    420
gtcagacata tcgaagaact cccgcaggtc atgagcgatg ccttccgcat tgcgcaatca    480
ggccgcccag gccggtgtg gatagacatt cctaaggatg tgcaaacggc agttttgag    540
```
(note: line at 540 as printed)
```
attgaaacac agcccgctat ggcagaaaaa gccgccgccc ccgcctttag cgaagaaagc    600
attcgtgacg cagcggcgat gattaacgct gccaaacgcc cggtgcttta tctgggcggc    660
ggtgtgatca atgcgcccgc acgggtgcgt gaactggcgg agaaagcgca actgcctacc    720
accatgactt taatggcgct gggcatgttg ccaaaagcgc atccgttgtc gctgggtatg    780
ctggggatgc acggcgtgcg cagcaccaac tatattttgc aggaggcgga tttgttgata    840
gtgctcggtg cgcgttttga tgaccgggcg attggcaaaa ccgagcagtt ctgtccgaat    900
gccaaaatca ttcatgtcga tatcgaccgt gcagagctgg taaaatcaa gcagccgcac    960
gtggcgattc aggcggatgt tgatgacgtg ctggcgcagt tgatcccgct ggtggaagcg   1020
caaccgcgtg cagagtggca ccagttggta gcggatttgc agcgtgagtt ccgtgtcca   1080
atcccgaaag cgtgcgatcc gttaagccat tacggcctga tcaacgccgt tgccgcctgt   1140
gtcgatgaca atgcaattat caccaccgac gttggtcagc atcagatgtg gaccgcgcaa   1200
gcttatccgc tcaatcgccc acgccagtgg ctgacctccg gtgggctggg cacgatgggt   1260
tttggcctgc ctgcgcgat tggcgctgcg ctggcgaacc cggatcgcaa agtgttgtgt   1320
ttctccggcg acggcagcct gatgatgaat attcaggaga tggcgaccgc cagtgaaaat   1380
cagctggatg tcaaaatcat tctgatgaac aacgaagcgc tggggctggt gcatcagcaa   1440
cagagtctgt tctacgagca aggcgttttt gccgccacct atccgggcaa aatcaacttt   1500
atgcagattg ccgccggatt cggcctcgaa acctgtgatt tgaataacga agccgatccg   1560
caggcttcat tgcaggaaat catcaatcgc cctggcccgg cgctgatcca tgtgcgcatt   1620
gatgccgaag aaaaagttta cccgatggtg ccgccaggtg cggcgaatac tgaaatggtg   1680
ggggaataag ccatgcaaaa cacaactcat gacaacgtaa ttctggagct caccgttcgc   1740
aaccatccgg gcgtaatgac ccacgttgt ggccttttg cccgccgcgc ttttaacgtt   1800
gaaggcattc tttgtctgcc gattcaggac agcgacaaaa gccatatctg gctactggtc   1860
aatgacgacc agcgtctgga gcagatgata agccaaatcg ataagctgga agatgtcgtg   1920
aaagtgcagc gtaatcagtc cgatccgacg atgtttaaca agatcgcggt gttttttcag   1980
taa                                                                  1983
```

<210> SEQ ID NO 68
<211> LENGTH: 1476
<212> TYPE: DNA
<213> ORGANISM: Escherichia coli

<400> SEQUENCE: 68

```
atggctaact acttcaatac actgaatctg cgccagcagc tggcacagct gggcaaatgt     60
cgctttatgg ccgcgatga attcgccgat ggcgcgagct accttcaggg taaaaaagta    120
gtcatcgtcg ctgtggcgc acagggtctg aaccagggcc tgaacatgcg tgattctggt    180
ctcgatatct cctacgctct gcgtaaagaa gcgattgccg agaagcgcgc gtcctggcgt    240
aaagcgaccg aaaatggttt taagtgggt acttacgaag aactgatccc acaggcggat    300
ctggtgatta acctgacgcc ggacaagcag cactctgatg tagtgcgcac cgtacagcca    360
ctgatgaaag acggcgcggc gctgggctac tcgcacggtt tcaacatcgt cgaagtgggc    420
```

```
gagcagatcc gtaaagatat caccgtagtg atggttgcgc cgaaatgccc aggcaccgaa      480
gtgcgtgaag agtacaaacg tgggttcggc gtaccgacgc tgattgccgt tcacccggaa      540
aacgatccga aggcgaagg catggcgatt gccaaagcct gggcggctgc aaccggtggt       600
caccgtgcgg gtgtgctgga atcgtccttc gttgcggaag tgaaatctga cctgatgggc      660
gagcaaacca tcctgtgcgg tatgttgcag gctggctctc tgctgtgctt cgacaagctg      720
gtggaagaag gtaccgatcc agcatacgca gaaaaactga ttcagttcgg ttgggaaacc      780
atcaccgaag cactgaaaca gggcggcatc accctgatga tggaccgtct ctctaacccg      840
gcgaaactgc gtgcttatgc gctttctgaa cagctgaaag agatcatggc accctgttc      900 cagaaacata tggacgacat catctccggc gaattctctt ccggtatgat ggcggactgg      960
gccaacgatg ataagaaact gctgacctgg cgtgaagaga ccggcaaaac cgcgtttgaa     1020
accgcgccgc agtatgaagg caaaatcggc gagcaggagt acttcgataa aggcgtactg     1080
atgattgcga tggtgaaagc gggcgttgaa ctggcgttcg aaaccatggt cgattccggc     1140
atcattgaag agtctgcata ttatgaatca ctgcacgagc tgccgctgat tgccaacacc     1200
atcgcccgta agcgtctgta cgaaatgaac gtggttatct ctgataccgc tgagtacggt     1260
aactatctgt tctcttacgc ttgtgtgccg ttgctgaaac cgtttatggc agagctgcaa     1320
ccgggcgacc tgggtaaagc tattccgaa ggcgcggtag ataacgggca actgcgtgat     1380
gtgaacgaag cgattcgcag ccatgcgatt gagcaggtag gtaagaaact gcgcggctat     1440
atgacagata tgaaacgtat tgctgttgcg ggttaa                               1476

<210> SEQ ID NO 69
<211> LENGTH: 1851
<212> TYPE: DNA
<213> ORGANISM: Escherichia coli

<400> SEQUENCE: 69
atgcctaagt accgttccgc caccaccact catggtcgta atatggcggg tgctcgtgcg       60
ctgtggcgcg ccaccggaat gaccgacgcc gatttcggta agccgattat cgcggttgtg      120
aactcgttca cccaatttgt accgggtcac gtccatctgc gcgatctcgg taaactggtc      180
gccgaacaaa ttgaagcggc tggcggcgtt gccaaagagt tcaacaccat tgcggtggat      240
gatgggattg ccatgggcca cggggggatg ctttattcac tgccatctcg cgaactgatc      300
gctgattccg ttagtatat ggtcaacgcc cactgcgccg acgccatggt ctgcatctct      360
aactgcgaca aaatcacccc ggggatgctg atggcttccc tgcgcctgaa tattccggtg      420
atctttgttt ccggcggccc gatggaggcc gggaaaacca acttccga tcagatcatc        480 aagctcgatc tggttgatgc gatgatccag ggcgcagacc cgaaagtatc tgactcccag      540
agcgatcagg ttgaacgttc cgcgtgtccg acctgcggtt cctgctccgg atgtttacc      600 gctaactcaa tgaactgcct gaccgaagcg ctgggcctgt cgcagccggg caacggctcg      660
ctgctggcaa cccacgccga ccgtaagcag ctgttcctta atgctggtaa acgcattgtt      720
gaattgacca acgttattac gagcaaaac gacgaaagtg cactgccgcg taatatcgcc      780
agtaaggcgg cgtttgaaaa cgccatgacg ctggatatcg cgatgggtgg atcgactaac      840
accgtacttc acctgctggc ggcggcgcag gaagcggaaa tcgacttcac catgagtgat      900
atcgataagc tttcccgcaa ggttccacag ctgtgtaaag ttgcgccgag cacccagaaa      960
taccatatgg aagatgttca ccgtgctggt ggtgttatcg gtattctcgg cgaactggat     1020
```

```
cgcgcggggt tactgaaccg tgatgtgaaa aacgtacttg gcctgacgtt gccgcaaacg    1080
ctggaacaat acgacgttat gctgacccag gatgacgcgg taaaaaatat gttccgcgca    1140
ggtcctgcag gcattcgtac cacacaggca ttctcgcaag attgccgttg ggatacgctg    1200
gacgacgatc gcgccaatgg ctgtatccgc tcgctggaac acgcctacag caaagacggc    1260
ggcctggcgg tgctctacgg taactttgcg gaaaacggct gcatcgtgaa aacggcaggc    1320
gtcgatgaca gcatcctcaa attcaccggc ccggcgaaag tgtacgaaag ccaggacgat    1380
gcggtagaag cgattctcgg cggtaaagtt gtcgccggag atgtggtagt aattcgctat    1440
gaaggcccga aaggcggtcc ggggatgcag gaaatgctct acccaaccag cttcctgaaa    1500
tcaatgggtc tcggcaaagc ctgtgcgctg atcaccgacg gtcgtttctc tggtggcacc    1560
tctggtcttt ccatcggcca cgtctcaccg gaagcggcaa gcggcggcag cattggcctg    1620
attgaagatg gtgacctgat cgctatcgac atcccgaacc gtggcattca gttacaggta    1680
agcgatgccg aactggcggc gcgtcgtgaa gcgcaggacg ctcgaggtga caaagcctgg    1740
acgccgaaaa atcgtgaacg tcaggtctcc tttgccctgc gtgcttatgc cagcctggca    1800
accagcgccg acaaaggcgc ggtgcgcgat aaatcgaaac tgggggggtta a            1851

<210> SEQ ID NO 70
<211> LENGTH: 29
<212> TYPE: DNA
<213> ORGANISM: Artificial Sequence
<220> FEATURE:
<223> OTHER INFORMATION: Synthetic Construct; Primer

<400> SEQUENCE: 70
ctctcccggg atggcaagtt cgggcacaa                                        29

<210> SEQ ID NO 71
<211> LENGTH: 40
<212> TYPE: DNA
<213> ORGANISM: Artificial Sequence
<220> FEATURE:
<223> OTHER INFORMATION: Synthetic Construct; Primer

<400> SEQUENCE: 71
ctctcccggg agatctttac tgaaaaaaca ccgcgatctt                            40

<210> SEQ ID NO 72
<211> LENGTH: 34
<212> TYPE: DNA
<213> ORGANISM: Artificial Sequence
<220> FEATURE:
<223> OTHER INFORMATION: Synthetic Construct; Primer

<400> SEQUENCE: 72
ctctcccggg atggctaact acttcaatac actg                                  34

<210> SEQ ID NO 73
<211> LENGTH: 37
<212> TYPE: DNA
<213> ORGANISM: Artificial Sequence
<220> FEATURE:
<223> OTHER INFORMATION: Synthetic Construct; Primer

<400> SEQUENCE: 73
ctctcccggg agatctttaa cccgcaacag caatacg                               37

<210> SEQ ID NO 74
<211> LENGTH: 29
```

```
<212> TYPE: DNA
<213> ORGANISM: Artificial Sequence
<220> FEATURE:
<223> OTHER INFORMATION: Synthetic Construct; Primer

<400> SEQUENCE: 74
ctcttttaaa atgcctaagt accgttccg                                    29

<210> SEQ ID NO 75
<211> LENGTH: 39
<212> TYPE: DNA
<213> ORGANISM: Artificial Sequence
<220> FEATURE:
<223> OTHER INFORMATION: Synthetic Construct; Primer

<400> SEQUENCE: 75
ctcttttaaa agatctttaa cccccagtt tcgatttat                           39

<210> SEQ ID NO 76
<211> LENGTH: 2166
<212> TYPE: DNA
<213> ORGANISM: Artificial Sequence
<220> FEATURE:
<223> OTHER INFORMATION: Synthetic Construct; Ptac-ilvD

<400> SEQUENCE: 76
ctagcgctgt gcaggtcgta aatcactgca taattcgtgt cgctcaaggc gcactcccgt    60
tctggataat gttttttgcg ccgacatcat aacggttctg gcaaatattc tgaaatgagc   120
tgttgacaat taatcatcgg ctcgtataat gtgtggaatt gtgagcggat aacaatttca   180
cacaggaaac agaattcccg gggagcagat tgaaaagcg catcatgatc ccacttcgtt    240
caaaagtcac caccgtcggt cgcaatgcag ctggcgctcg cgcccttggg cgtgccaccg    300
gcaccaagga aatgagttc ggcaagccaa ttgttgccat cgtgaactcc tacacccagt    360
tcgtgcccgg acacgttcac cttaagaacg tcggcgatat tgtggcagat gcagtgcgca    420
aagccggtgg cgttccaaaa gaattcaaca ccatcgccgt cgatgacggc atcgccatgg    480 gacacgcgg catgctgtac tccctgccat cccgtgaaat catcgccgac tccgtcgaat    540
acatggtcaa cgcacacacc gccgacgcca tggtgtgtat ctccaactgt gacaagatca    600
ccccaggcat gctcaacgca gcaatgcgcc tgaacatccc agtggtcttc gtttccggtg    660
gcccaatgga agctggcaag ctgtcgtcg ttgacgcgt tgcacacgca ccaaccgacc    720
tcatcaccgc gatctccgca tccgcaagcg atgcagtcga cgacgcaggc cttgcagccg    780
ttgaagcatc cgcatgccca acctgtggct cctgctccgg tatgttcacc gcgaactcca    840
tgaactgcct caccgaagct ctgggacttt ctctcccagg caacggctcc accctggcaa    900
cccacgcagc acgtcgcgca ctgtttgaaa aggccggcga aaccgtcgtt gaactgtgcc    960
gccgctacta cggtgaagaa gacgaatccg ttctgccacg tggcattgcc accaagaagg   1020
cattcgaaaa cgcaatggca ctggatatgg ccatgggtgg atccaccaac accatcctcc   1080
acatcctcgc agctgcccag gaaggcgaag ttgacttcga cctcgcagac atcgacgaac   1140
tgtccaaaaa cgtcccctgc ctgtccaagg ttgcaccaaa ctccgactac cacatggaag   1200
acgtccaccg cgccggtggc attccagcac tgctcggcga gctcaaccgc ggtggcctgc   1260
tgaataagga cgtccactcc gttcactcca acgaccttga aggttggttg gatgactggg   1320
atatccgctc tggcaagacc accgaagtag caaccgaact cttccacgca gccccaggtg   1380
gcatccgcac caccgaagca ttctccaccg agaaccgctg ggacgaactc gacaccgacg   1440
```

```
ctgccaaggg ctgcatccgc gacgttgaac acgcctacac cgccgacggc ggcctggttg    1500
ttcttcgcgg caacatctcc cctgacggcg cagtgatcaa gtccgcaggt atcgaagaag    1560
agctgtggaa cttcaccgga ccagcacgag ttgtcgaaag ccaggaagag gcagtctctg    1620
tcatcctgac caagaccatc caagctggcg aagttctggt cgtccgctac gaaggcccat    1680
caggtggacc aggcatgcag gaaatgcttc acccaaccgc attcctcaag ggatccggcc    1740
tgggcaagaa gtgtgcactg atcaccgacg gccgtttctc cggaggttcc tcaggactgt    1800
ccatcggcca cgtctcccca gaagcagcac acggcggagt cattggtctg atcgaaaacg    1860
gcgacatcgt ttccatcgac gttcacaacc gcaagctcga agttcaggtc tccaacgagg    1920
aactccagcg ccgccgcgac gctatgaacg cctccgagaa gccatggcag ccagtcaacc    1980
gtaaccgcgt tgtcaccaag gcactgcgcg catacgcaaa gatggctacc tccgctgata    2040
agggtgcagt ccgtcaggtc gactaaccct ttgtaagtgt ttgagcaccg gttccctact    2100
ttgggttccg gtgcttttc atgtcttggg ctgtgtgggc gtggtggagc tccccgttgc    2160
aaatac                                                              2166

<210> SEQ ID NO 77
<211> LENGTH: 40
<212> TYPE: DNA
<213> ORGANISM: Artificial Sequence
<220> FEATURE:
<223> OTHER INFORMATION: Synthetic Construct; Primer

<400> SEQUENCE: 77
atatcctgca ggctagcgct gtgcaggtcg taaatcaact                           40

<210> SEQ ID NO 78
<211> LENGTH: 38
<212> TYPE: DNA
<213> ORGANISM: Artificial Sequence
<220> FEATURE:
<223> OTHER INFORMATION: Synthetic Construct; Primer

<400> SEQUENCE: 78
atatgctagc tcctgcaggt atttgcaacg gggagctc                             38
```

CORYNEFORM BACTERIUM TRANSFORMANT AND PROCESS FOR PRODUCING ISOBUTANOL USING THE SAME

This application is a U.S. national stage of International Application No. PCT/JP2010/055504 filed Mar. 29, 2010.

TECHNICAL FIELD

The present invention relates to an isobutanol producing technology. In more detail, the present invention relates to a *Corynebacterium glutamicum* transformant capable of producing isobutanol as a result of specific gene recombination, and relates to an efficient process for producing isobutanol using the same.

BACKGROUND ART

Against the backdrop of global warming and exhaustion of fossil resources, "biofuels" obtainable from renewable resources attract attention. Isobutanol and n-butanol, as a next-generation biofuel following bioethanol, have many advantages, such as high heat content, low corrosivity, low water miscibility, capability of being mixed at high concentrations into gasoline, and high miscibility with diesel oil fuel.

Isobutanol is found as one of the by-products called fusel alcohols produced during alcoholic fermentation by yeast. Fusel alcohols are higher alcohols including isobutanol, isoamyl alcohol, active amyl alcohol, and derived from a German word "fusel" meaning "bad alcohol." One century ago, Enrlich first advocated that fusel alcohols are derived from amino acid metabolic system. This metabolic system is called Enrlich pathway where a 2-keto acid, which is a biosynthetic and metabolic intermediate from valine, leucine, isoleucine, methionine, phenylalanine, or the like, is changed into aldehyde by 2-keto acid decarboxylase having broad substrate specificity, and then changed into an alcohol by alcohol dehydrogenase. Isobutanol derives from 2-ketoisovalerate, which is a biosynthetic and metabolic intermediate to valine (Non Patent Literature 1).

Non Patent Literature 2 describes that in alcoholic fermentation by yeast, the amount of isobutanol (fusel alcohol) depends on proliferation of yeast.

Examples of known isobutanol producing technologies with use of recombinant bacteria include the following. For example, Patent Literature 1 discloses an isobutanol producing technology in which an acetohydroxy acid synthase gene derived from *Klebsiella pneumoniae* or *Bacillus subtilis*; an acetohydroxy acid isomeroreductase gene derived from *Bacillus subtilis, Escherichia coli*, or *Saccharomyces cerevisiae*; a dihydroxy acid dehydratase gene derived from *Escherichia coli* or *Saccharomyces cerevisiae*; a 2-keto acid decarboxylase gene derived from *Lactococcus lactis*; and an alcohol dehydrogenase gene derived from *Escherichia coli* or *Clostridium acetobutylicum* are expressed with use of a host, such as *Escherichia coli, Saccharomyces cerevisiae, Bacillus subtilis, Lactococcus plantarum*, or *Enterococcus faecalis*.

However, the technologies described in the literature do not include a butanol producing technology with use of *Corynebacterium glutamicum*, which is a specific species of coryneform bacteria, as a host. The above-described various kinds of genes to be introduced do not include any genes derived from *Corynebacterium glutamicum*, which is the host of the present invention, and the literature does not describe that high expression of the endogenous genes provides a transformant excellent in capability of isobutanol production.

Further, while the above-mentioned technologies are all isobutanol producing technologies involving proliferation of the microorganism to be used, the present invention proposes that a production procedure under reducing conditions involving no substantial proliferation is superior to a procedure involving proliferation (see Comparative Examples below).

Also, Patent literature 2 and Non Patent Literature 3 disclose isobutanol producing technologies in which an acetohydroxy acid synthase gene derived from *Escherichia coli* or *Bacillus subtilis*; an acetohydroxy acid isomeroreductase gene derived from *Escherichia coli*; a dihydroxy acid dehydratase gene derived from *Escherichia coli*; a 2-keto acid decarboxylase gene derived from *Lactococcus lactis, Saccharomyces cerevisiae*, or *Clostridium acetobutylicum*; and an alcohol dehydrogenase gene derived from *Saccharomyces cerevisiae* are expressed with use of *Escherichia coli* as a host.

However, what is disclosed therein does not include any butanol producing technologies in which a microorganism species, *Corynebacterium glutamicum*, is used as a host. Further, the isobutanol producing technologies disclosed therein are inefficient in isobutanol production.

The inventors have already disclosed a technology in which a recombinant *Corynebacterium glutamicum* is made to react in a reaction mixture under reducing conditions without substantial proliferation, for highly efficient production of lactic acid, succinic acid, or ethanol (Patent Literature 3). However, nothing is mentioned regarding isobutanol, whose synthetic and metabolic pathway for production differs from those of the organic compounds described in Patent Literature 3. Further, there is no teaching regarding that highly efficient production of isobutanol can be achieved without proliferation or that such a production process without proliferation is more efficient than the process involving proliferation.

CITATION LIST

Patent Literature

[PTL 1] WO 2007/050671
[PTL 2] WO 2008/098227
[PTL 3] Japanese Patent No. 3869788

Non Patent Literature

[NPL 1] Journal of Biological Chemistry, Vol. 273, 1998, 25751-25756
[NPL 2] Process Biochemistry, Vol. 29, 1994, 303-309
[NPL 3] Nature, Vol. 451, 2008, 86-90

SUMMARY OF INVENTION

Technical Problem

An object of the present invention is to provide a microorganism capable of efficiently producing isobutanol, and a process for efficiently producing isobutanol using the microorganism.

Solution to Problem

The present inventors have wholeheartedly carried out investigations in order to achieve the object described above and obtained the following finding.

A *Corynebacterium glutamicum* transformant having the following genes (1) to (5):
(1) a gene which encodes an enzyme having acetohydroxy acid synthase activity;
(2) a gene which encodes an enzyme having acetohydroxy acid isomeroreductase activity;
(3) a gene which encodes an enzyme having dihydroxy acid dehydratase activity;
(4) a gene which encodes an enzyme having 2-keto acid decarboxylase activity; and
(5) a gene which encodes an enzyme having alcohol dehydrogenase activity,
which genes function in *Corynebacterium glutamicum*, at least one of the genes being endogenous, and at least one of the genes being exogenous, efficiently produces isobutanol.

The present invention, which has been completed based on the above-mentioned findings and further investigations, provides the following microorganism and process for producing isobutanol.

[1] A *Corynebacterium glutamicum* transformant having the capability of producing isobutanol and the following genes (1) to (5):
(1) a gene which encodes an enzyme having acetohydroxy acid synthase activity;
(2) a gene which encodes an enzyme having acetohydroxy acid isomeroreductase activity;
(3) a gene which encodes an enzyme having dihydroxy acid dehydratase activity;
(4) a gene which encodes an enzyme having 2-keto acid decarboxylase activity; and
(5) a gene which encodes an enzyme having alcohol dehydrogenase activity,
at least one of the genes being endogenous, and at least one of the genes being exogenous.
[2] The transformant according to the above [1], wherein the endogenous gene is highly expressed.
[3] The transformant according to the above [1] or [2], wherein the endogenous gene include a gene selected from (1) a gene which encodes an enzyme having acetohydroxy acid synthase activity, (2) a gene which encodes an enzyme having acetohydroxy acid isomeroreductase activity, and (3) a gene which encodes an enzyme having dihydroxy acid dehydratase activity.
[4] The transformant according to any one of the above [1] to [3], wherein the gene which encodes an enzyme having alcohol dehydrogenase activity is a gene derived from *Escherichia coli* or *Pseudomonas putida*.
[5] The transformant according to any one of the above [1] to [4], wherein
the gene which encodes an enzyme having acetohydroxy acid synthase activity is a gene selected from a DNA comprising the base sequence of SEQ ID NO: 34, a DNA comprising the base sequence of SEQ ID NO: 58, and a DNA which hybridizes to a DNA comprising a complementary base sequence of a DNA comprising the base sequence of SEQ ID NO: 34 or 58 under stringent conditions and which encodes a polypeptide having acetohydroxy acid synthase activity;
the gene which encodes an enzyme having acetohydroxy acid isomeroreductase activity is a gene selected from a DNA comprising the base sequence of SEQ ID NO: 61, and a DNA which hybridizes to a DNA comprising a complementary base sequence of a DNA comprising the base sequence of SEQ ID NO: 61 under stringent conditions and which encodes a polypeptide having acetohydroxy acid isomeroreductase activity;
the gene which encodes an enzyme having dihydroxy acid dehydratase activity is a gene selected from a DNA comprising the base sequence of SEQ ID NO: 62, and a DNA which hybridizes to a DNA comprising a complementary base sequence of a DNA comprising the base sequence of SEQ ID NO: 62 under stringent conditions and which encodes a polypeptide having dihydroxy acid dehydratase activity;
the gene which encodes an enzyme having 2-keto acid decarboxylase activity is a gene selected from a DNA comprising the base sequence of SEQ ID NO: 43, a DNA comprising the base sequence of SEQ ID NO: 52, and a DNA which hybridizes to a DNA comprising a complementary base sequence of a DNA comprising the base sequence of SEQ ID NO: 43 or 52 under stringent conditions and which encodes a polypeptide having 2-keto acid decarboxylase activity; and
the gene which encodes an enzyme having alcohol dehydrogenase activity is a gene selected from a DNA comprising the base sequence of SEQ ID NO: 40, a DNA comprising the base sequence of SEQ ID NO: 46, and a DNA which hybridizes to a DNA comprising a complementary base sequence of a DNA comprising the base sequence of SEQ ID NO: 40 or 46 under stringent conditions and which encodes a polypeptide having alcohol dehydrogenase activity.
[6] The transformant according to anyone of the above [1] to [5], wherein the *Corynebacterium glutamicum* used as a host is *Corynebacterium glutamicum* R (FERM BP-18976), ATCC13032, or ATCC13869.
[7] A transformant which is *Corynebacterium glutamicum* IBU1 (Accession Number: NITE BP-718), *Corynebacterium glutamicum* IBU2 (Accession Number: NITE BP-719), *Corynebacterium glutamicum* IBU3 (Accession Number: NITE BP-720), or *Corynebacterium glutamicum* IBU4 (Accession Number: NITE BP-721).
[8] A process for producing isobutanol, which comprises a step of reacting the transformant according to anyone of the above [1] to [7] or treated product thereof in a reaction culture medium containing saccharides under reducing conditions, and a step of collecting the resulting isobutanol.
[9] The process for producing isobutanol according to the above [8], wherein the transformant does not substantially proliferate in the reaction step.
[10] The process for producing isobutanol according to the above [8] or [9], wherein the oxidation-reduction potential (ORP) of the reaction culture medium under reducing conditions is −100 mV to −500 mV.

Advantageous Effects of Invention

The present invention has provided a recombinant isobutanol-producing transformant which produces isobutanol with remarkable efficiency from saccharides. In particular, the transformant of the present invention can produce isobutanol from saccharides without substantial proliferation under reducing conditions. As a result, the carbon to be used is not consumed for proliferation but solely used for production of isobutanol, which is the objective product, achieving high efficiency of isobutanol production. In addition, secretions associated with the proliferation of the microorganism are reduced, and therefore, isobutanol, which is the object product, can be easily collected and purified.

The present invention enables an efficient isobutanol production from renewable resources and achieves a rational process for industrial production.

DESCRIPTION OF EMBODIMENTS

Figure 1:
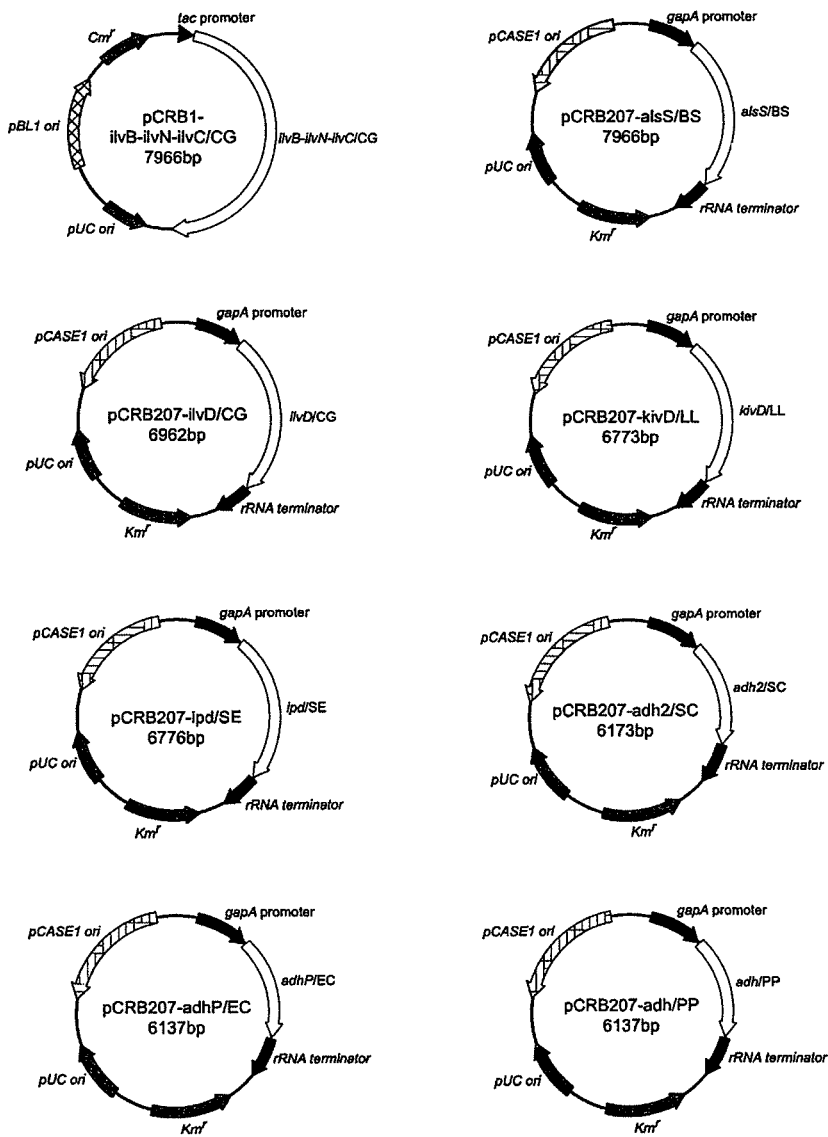
FIG. 1 is a schematic view showing pCRB1-ilvB-ilvN-ilvC/CG, pCRB207-alsS/BS, pCRB207-ilvD/CG, pCRB207-kivD/LL, pCRB207-ipd/SE, pCRB207-adh2/SC, pCRB207-adhP/EC, and pCRB207-adh/PP, prepared in Example 1 (4).

Hereinafter, the present invention will be described in detail.

(I) Transformant Capable of Producing Isobutanol

The transformant of the present invention capable of producing isobutanol is a *Corynebacterium glutamicum* transformant having the above-described genes (1) to (5), which genes function in *Corynebacterium glutamicum*, at least one of the genes being endogenous, and at least one of the genes being exogenous. The endogenous gene is preferably highly expressed. That is, the endogenous gene that *Corynebacterium glutamicum* originally has is preferably highly expressed as a result of further introduction of the same gene as a plasmid etc.

"Function in *Corynebacterium glutamicum*" means that the enzyme encoded by the DNA is expressed in *Corynebacterium glutamicum* to perform catalysis.

Host

The host subjected to transformation in the present invention is not particularly limited as long as it is a *Corynebacterium glutamicum* capable of being transformed by a recombinant vector comprising a group of isobutanol production-related genes, allowing expression of isobutanol production-related enzymes encoded by the genes, and producing isobutanol as a result.

The *Corynebacterium glutamicum* used as a host belongs to a group of microorganisms defined in Bergeys Manual of Determinative Bacteriology, Vol. 8, 599 (1974).

Specific examples thereof include *Corynebacterium glutamicum* R (FERN P-18976), ATCC13032, ATCC13869, ATCC13058, ATCC13059, ATCC13060, ATCC13232, ATCC13286, ATCC13287, ATCC13655, ATCC13745, ATCC13746, ATCC13761, ATCC14020, ATCC31831, MJ-233 (FERN BP-1497), and MJ-233AB-41 (FERN BP-1498).

Since coryneform bacteria, such as *Brevibacterium flavums*, *Brevibacterium lactofermentum*, *Brevibacterium divaricatum*, and *Corynebacterium lilium*, are categorized into *Corynebacterium glutamicum* according to molecular biological classification, such bacteria are also included in the present invention (Liebl, W. et al., Transfer of *Brevibacterium divaricatum* DSM 20297T, "*Brevibacterium flavums*" DSM 20411, "*Brevibacterium lactofermentum*" DSM 20412 and DSM 1412, and *Corynebacterium glutamicum* and their distinction by rRNA, gene restriction patterns. Int J Syst Bacteriol. 41: 255-260. (1991); and Kazuo Komagata et al., "Classification of the cryneform group of bacteria", Fermentation and industry, 45: 944-963 (1987)).

Particularly preferred examples of the host include *Corynebacterium glutamicum* R (FERM P-18976), ATCC13032, and ATCC13869.

The *Corynebacterium glutamicum* may be, let alone a wild strain, a mutant thereof or an artificial recombinant thereof. Examples of such a *Corynebacterium glutamicum* include disruptants in which one or more genes of lactate dehydrogenase, phosphoenolpyruvate carboxylase, malate dehydrogenase, etc. are disrupted. Using such a disruptant as a host can improve isobutanol productivity and reduce production of by-products.

Particularly preferred are *Corynebacterium glutamicum* R (FERM P-18976) and a disruptant thereof in which lactate dehydrogenase (LDH) is disrupted. A lactate dehydrogenase disruptant of *Corynebacterium glutamicum* R (FERM P-18976) is a *Corynebacterium glutamicum* R in which a lactate dehydrogenase gene is disrupted with use of recombination technique so that the metabolic pathway from pyruvic acid to lactic acid is blocked. Such a lactate dehydrogenase disruptant and the preparation method thereof are described in WO 2005/010182 A1.

Isobutanol Production-Related Genes

Herein, the following genes (1) to (5) are also referred to as isobutanol production-related genes.

(1) Gene which Encodes Enzyme Having Acetohydroxy Acid Synthase (AHAS) Activity

Preferred as this gene is at least one kind of DNA selected from the group consisting of a DNA comprising the base sequence of SEQ ID NO: 34, a DNA comprising the base sequence of SEQ ID NO: 58, and a DNA which hybridizes to a DNA comprising a complementary base sequence of a DNA comprising the base sequence of SEQ ID NO: 34 or 58 under stringent conditions and which encodes an enzyme having acetohydroxy acid synthase activity.

(2) Gene which Encodes Enzyme Having Acetohydroxy Acid Isomeroreductase (AHAIR) Activity Preferred as this gene is at least one kind of DNA selected from the group consisting of a DNA comprising the base sequence of SEQ ID NO: 61, and a DNA which hybridizes to a DNA comprising a complementary base sequence of a DNA comprising the base sequence of SEQ ID NO: 61 under stringent conditions and which encodes an enzyme having acetohydroxy acid isomeroreductase activity.

(3) Gene which Encodes Enzyme Having Dihydroxy Acid Dehydratase (DHAD) Activity

Preferred as this gene is at least one kind of DNA selected from the group consisting of a DNA comprising the base sequence of SEQ ID NO: 62, and a DNA which hybridizes to a DNA comprising a complementary base sequence of a DNA comprising the base sequence of SEQ ID NO: 62 under stringent conditions and which encodes an enzyme having dihydroxy acid dehydratase activity.

(4) Gene which Encodes Enzyme Having 2-Keto Acid Decarboxylase (KDC) Activity

Preferred as this gene is at least one kind of DNA selected from the group consisting of a DNA comprising the base sequence of SEQ ID NO: 43, a DNA comprising the base sequence of SEQ ID NO: 52, and a DNA which hybridizes to a DNA comprising a complementary base sequence of a DNA comprising the base sequence of SEQ ID NO: 43 or 52 under stringent conditions and which encodes an enzyme having 2-keto acid decarboxylase activity.

(5) Gene which Encodes Enzyme Having Alcohol Dehydrogenase (ADH) Activity

Preferred as this gene is at least one kind of DNA selected from the group consisting of a DNA comprising the base sequence of SEQ ID NO: 40, a DNA comprising the base sequence of SEQ ID NO: 46, a DNA comprising the base sequence of SEQ ID NO: 49, and a DNA which hybridizes to a DNA comprising a complementary base sequence of a DNA comprising the base sequence of SEQ ID NO: 40, 46, or 49 under stringent conditions and which encodes an enzyme having alcohol dehydrogenase activity.

The gene (1) of the present invention is a gene which encodes an enzyme having acetohydroxy acid synthase activity. The gene (2) of the present invention is a gene which encodes an enzyme having acetohydroxy acid isomeroreductase activity. The gene (3) of the present invention is a gene which encodes an enzyme having dihydroxy acid dehydratase activity. The gene (4) of the present invention is a gene which encodes an enzyme having 2-keto acid decarboxylase activity. The gene (5) of the present invention is a gene which encodes an enzyme having alcohol dehydrogenase activity.

As the above isobutanol production-related genes (1) to (5), DNA fragments synthesized according to the sequences may be used. Alternatively, the fragments can be obtained by a hybridization method and the PCR method based on amino acid sequences conserved among isobutanol production-related enzyme proteins. Further, such fragments can be obtained by degenerate PCR with use of mixed primers designed based on other known isobutanol production-related gene sequences.

In the above isobutanol production-related genes (1) to (5), as long as they function in *Corynebacterium glutamicum* having isobutanol-producing activity, a part of the natural base sequence may be substituted by another base (nucleotide) or deleted. Also, a base (nucleotide) may be newly inserted, and a part of the base sequence may be transposed. Any of these gene derivatives may be used in the present invention. The above-mentioned "a part" may be, for example, one to several (1 to 5, preferably 1 to 3, and more preferably 1 to 2) in terms of amino-acid residues.

The origin of the above genes (1) to (5) may be a bacterium capable or incapable of producing isobutanol.

Isobutanol is found as one of the by-products called fusel alcohols produced during alcoholic fermentation by yeast (Hazelwood, L. A. et al., The Ehrlich pathway for fusel alcohol production: a century of research on *Saccharomyces cerevisiae* metabolism. Appl. Environ. Microbiol. 74: 2259-2266 (2008)). Fusel alcohols are higher alcohols including isobutanol, isoamyl alcohol, active amyl alcohol, and were found by Enrlich one century ago to derive from amino acid metabolic system. This metabolic system is called Enrlich pathway where a 2-keto acid, which is a biosynthetic and metabolic intermediate to valine, leucine, isoleucine, methionine, phenylalanine, or the like, is changed into aldehyde by 2-keto acid decarboxylase having broad substrate specificity, and then changed into an alcohol by alcohol dehydrogenase. Isobutanol derives from 2-ketoisovalerate which is a biosynthetic and metabolic intermediate to valine (Dickinson, J. R. et al., An investigation of the metabolism of valine to isobutyl alcohol in *Saccharomyces cerevisiae*. J., Biol. Chem. 273: 25751-25756 (1998)).

In particular, the isobutanol-producing pathway or the 5-step metabolic pathway from pyruvic acid to isobutanol (the first 3 steps are the same as those of a valine biosynthesis pathway) comprises, (1) acetohydroxy acid synthase that catalyzes the reaction from pyruvic acid to acetolactate (hereafter the enzyme will be abbreviated to "AHAS"), (2) acetohydroxy acid isomeroreductase that catalyzes the reaction from acetolactate to 2,3-dihydroxyisovalerate (hereafter the enzyme will be abbreviated to "AHAIR"), (3) dihydroxy acid dehydratase that catalyzes the reaction from 2,3-dihydroxyisovalerate to 2-ketoisovalerate (hereafter the enzyme will be abbreviated to "DHAD"), (4) 2-keto acid decarboxylase that catalyzes the reaction from 2-ketoisovalerate to isobutyrylaldehyde (hereafter the enzyme will be abbreviated to "KDC"), and (5) alcohol dehydrogenase that catalyzes the reaction from isobutyrylaldehyde to isobutanol (hereafter the enzyme will be abbreviated to "ADH").

These genes may also be obtained from bacteria incapable of producing isobutanol.

The first 3 steps (1) to (3) are the same as those of the biosynthesis pathway of valine, which is an essential amino acid, and therefore widely encoded on the genome of bacteria, archaea, and eukaryote. Genes obtained from any living organism may be used as long as the genes are expressed and function in *Corynebacterium glutamicum*. As for the first step (1), bacteria, such as *Bacillus subtilis*, have acetohydroxy acid synthase, which is considered not as a part of the valine biosynthesis pathway, but as functioning to prevent oxidization by eliminating excessively accumulated pyruvic acid in the bacterial cells (the gene name is alsS) (Cruz Ramos, H. et al., Fermentative metabolism of *Bacillus subtilis*: physiology and regulation of gene expression. J. Bacteriol. 182, 3072-3080 (2000)). This gene may be used.

Inter alia, as the genes regarding steps (1) to (3), it may be preferable to use genes derived from *Corynebacterium glutamicum* as a host.

Specific examples of the other metabolic steps (4) and (5) are shown below.

As the first example, although isobutanol production has not been mentioned, it is reported that *Lactococcus lactis* has a kivD gene which encodes KDC (de la Plaza, M. et al., Biochemical and molecular characterization of α-ketoisovalerate decarboxylase, an enzyme involved in the formation of aldehydes from amino acids by *Lactococcus lactis*. FEMS Microbial., Lett. 238, 367-374 (2004)) and that *Staphylococcus epidermidis* has an ipd gene which encodes KDC (Zhang, Y. Q. et al., Genome-based analysis of virulence genes in a non-biofilm-forming *Staphylococcus epidermidis* strain (ATCC 12228) Mol. Microbial. 49, 1577-1593 (2003)). Therefore, as the gene (4) which encodes an enzyme having 2-keto acid decarboxylase activity, the above-mentioned kivD gene derived from *Lactococcus lactis* or ipd gene derived from *Staphylococcus epidermidis* may be used. The present invention revealed that introduction of a kivD gene derived from *Lactococcus lactis* or an ipd gene derived from *Staphylococcus epidermidis* into *Corynebacterium glutamicum* as a host leads to a high KDC activity (see Examples below).

As the second example, it is known that the ADH in the metabolic step (5), of which the substrate specificity is moderate, reacts with not only isobutyryl aldehyde but also aldehydes, such as acetaldehyde and butyraldehyde. Therefore, the ADH-encoding gene derived from *Escherichia coli* (adhP) (Blattner, F. R. et al., The complete genome sequence of *Escherichia coli* K-12. Science 277, 1453-1474, (1977)) or the ADH-encoding gene derived from *Pseudomonas putida* (adh) (Accession number: YP_001267259), of which isobutanol production has not been reported, may be used. The present invention revealed that, when isobutyryl aldehyde is used as the substrate, introduction of an adhP gene derived from *Escherichia coli* or an adh gene derived from *Pseudomonas putida* into *Corynebacterium glutamicum* as a host leads to a higher ADH activity than introduction of an adh2 gene derived from *Saccharomyces cerevisiae* (see Examples below).

Therefore, the kind and combination of the microorganism of origin, the order of introduction, etc. of the above genes (1) to (5) are not particularly limited as long as at least one of the genes is derived from *Corynebacterium glutamicum* as a host.

The genes (1) to (5) may be any of the following: 1 endogenous gene and 4 exogenous genes, 2 endogenous genes and 3 exogenous genes, 3 endogenous genes and 2 exogenous genes, and 4 endogenous genes and 1 exogenous gene. Particularly preferred is 3 endogenous genes and 2 exogenous genes. Also preferred is that the endogenous genes include genes (1) to (3) and the exogenous genes include genes (4) and (5).

Preferred embodiments of the isobutanol production-related genes (1) to (5) are as follows. As the gene (1), preferred is that the DNA comprising the base sequence of SEQ ID NO: 34 and the DNA comprising the base sequence of SEQ ID NO: 58 are a gene derived from *Corynebacterium glutamicum* (ilvBN) and a gene derived from *Bacillus subtilis* (alsS), respectively.

As the gene (2), preferred is that the DNA comprising the base sequence of SEQ ID NO: 61 is a gene derived from *Corynebacterium glutamicum* (ilvC).

As the gene (3), preferred is that the DNA comprising the base sequence of SEQ ID NO: 62 is a gene derived from *Corynebacterium glutamicum* (ilvD).

As the gene (4), preferred is that the DNA comprising the base sequence of SEQ ID NO: 43 and the DNA comprising the base sequence of SEQ ID NO: 52 are a gene derived from *Lactococcus lactis* (kivD) and a gene derived from *Staphylococcus epidermidis* (ipd), respectively.

As the gene (5), preferred is that the DNA comprising the base sequence of SEQ ID NO: 40 is a gene derived from *Escherichia coli* (adhP), that the DNA comprising the base sequence of SEQ ID NO: 46 is a gene derived from *Pseudomonas putida* (adh), and that the DNA comprising the base sequence of SEQ ID NO: 49 is a gene derived from *Saccharomyces cerevisiae* (adh2).

In the present invention, each of the above-described genes (1) to (5) may be hybridized with a DNA comprising the complementary base sequence of the DNA under stringent conditions.

Preferably, (1) is a DNA comprising the base sequence of SEQ ID NO: 34 derived from *Corynebacterium glutamicum* or a DNA comprising the base sequence of SEQ ID NO: 58 derived from *Bacillus subtilis*; (2) is a DNA comprising the base sequence of SEQ ID NO: 61 derived from *Corynebacterium glutamicum*; (3) is a DNA comprising the base sequence of SEQ ID NO: 62 derived from *Corynebacterium glutamicum*; (4) is a DNA comprising the base sequence of SEQ ID NO: 43 derived from *Lactococcus lactis* or a DNA comprising the base sequence of SEQ ID NO: 52 derived from *Staphylococcus epidermidis*; and (5) is a DNA comprising the base sequence of SEQ ID NO: 40 derived from *Escherichia coli*, a DNA comprising the base sequence of SEQ ID NO: 46 derived from *Pseudomonas putida*, or a DNA comprising the base sequence of SEQ ID NO: 49 derived from *Saccharomyces cerevisiae*.

Herein, for example, "a DNA sequence which hybridizes to a DNA comprising a complementary base sequence of SEQ ID NO: 34 under stringent conditions" means a DNA obtainable by colony hybridization, plaque hybridization, or the like with use of a DNA comprising a complementary base sequence of SEQ ID NO: 34 as a probe.

The "stringent conditions" as used herein means general conditions, for example, the conditions described in Molecular Cloning, A Laboratory Manual, Second Edition, Vol 0.2, p. 11.45 (1989) etc. It means, in particular, conditions where hybridization occurs at a temperature 5 to 10° C. below the melting temperature (Tm) of a perfect hybrid.

Also, in the present invention, for example, a DNA which hybridizes to a DNA comprising a complementary base sequence of SEQ ID NO: 34 under stringent conditions is preferably a DNA having about 90% or more sequence homology with a DNA comprising the base sequence of SEQ ID NO: 34. The DNA has more preferably about 92% or more, further preferably about 95% or more, and particularly preferably about 98% or more sequence homology. The homology values are calculated with use of calculation software GENETYX (registered trademark) Ver. 8 (made by Genetics).

The transformant of the present invention capable of producing isobutanol is obtainable by providing the production capability to *Corynebacterium glutamicum* by introducing at least one exogenous gene of the above DNAs (1) to (5), which function in *Corynebacterium glutamicum*. For high expression of at least one endogenous gene of the above DNAs (1) to (5), the corresponding endogenous gene derived from *Corynebacterium glutamicum* is introduced.

In the polymerase chain reaction (PCR) method, the oligonucleotide primers shown below may be used to amplify the sequences which each encode AHAS, AHAIR, DHAD, KDC, or ADH derived from various kinds of living organisms. Examples of such primers include the primers represented by base sequences of SEQ ID NOs: 36 and 37 for amplifying an AHAS-encoding gene, the primers represented by base sequences of SEQ ID NOs: 63 and 64 for amplifying an AHAIR-encoding gene, the primers represented by base sequences of SEQ ID NOs: 65 and 66 for amplifying a DHAD-encoding gene, the primers represented by base sequences of SEQ ID NOs: 44 and 45 for amplifying a KDC-encoding gene, the primers represented by base sequences of SEQ ID NOs: 41 and 42 for amplifying an ADH-encoding gene, etc.

In the PCR method, a known PCR device, for example a thermal cycler, may be used. The PCR cycle may be set according to known techniques. For example, the condition is a cycle of denaturation, annealing and extension repeated usually 10 to 100 times, preferably about 20 to 50 times. Templates used in the PCR to amplify the genes which encode AHAS, AHAIR, DHAD, KDC, and ADH may be DNAs isolated from a microorganism which exhibits the enzyme activity responsible for the above-mentioned butanol-producing pathway.

A gene obtained by the PCR method may be introduced into a suitable cloning vector. As the cloning method, commercially available PCR cloning systems, such as pGEM-T easy vector system (made by Promega), TOPO TA-cloning system (made by Invitrogen), Mighty Cloning Kit (made by Takara), etc. may be used. Also, by a hybridization method with use of, as a template, synthetic primers suitably designed based on a known base sequence of a gene which encodes AHAS, AHAIR, DHAD, KDC or ADH, a DNA fragment comprising the corresponding region may be obtained. An example of such a method will be described in detail in Examples.

Construction of Vector

Subsequently, a cloning vector comprising a gene obtained by the PCR method is introduced into a microorganism, for example, *Escherichia coli* JM109 strain for transformation. The transformed strain is cultured in a culture medium containing an antibiotic suitable for the marker gene in the vector (for example, ampicillin, chloramphenicol, etc.), and cells are collected from the culture. From the collected cells, plasmid DNA is extracted. The extraction of the plasmid DNA can be performed with use of a known technique. A commercial plasmid extraction kit may also be used for easy extraction. Examples of the commercial plasmid extraction kit include Qiaquick plasmid purification kit (trade name) made by QIAGEN. By determining the base sequence of this extracted plasmid DNA, the sequences of genes encoding AHAS, AHAIR, DHAD, KDC, and ADH can be confirmed. The base sequence of the DNA can be determined by a known method, for example, the dideoxy chain termination method etc. Alternatively, the base sequence can also be determined with use of a capillary electrophoretic system which utilizes multi-fluorescence technique for detection. Alternatively, the base sequence can also be determined with use of a DNA sequencer, for example, ABI PRISM 3730×1 DNA Analyzer (made by Applied Biosystem) etc.

The above-mentioned methods can be performed in the usual manner of genetic engineering experiments. Vectors of various kinds of microorganisms, and methods for introduction and expression of exogenous genes are described in many experimental books (for example, Sambrook, J. & Russell, D. W. Molecular Cloning: A Laboratory Manual (3rd Edition) CSHL Press (2001), or Ausubel, F. et al. Current protocols in molecular biology. Green Publishing and Wiley InterScience, New York (1987), etc). Therefore, selection of vectors, and introduction and expression of genes can be performed according to these books.

A wide variety of promoters can suitably be used in the present invention. Such a promoter may be obtained from many known supply sources including yeast, bacteria, and other cell supply sources and may have any base sequence as long as it has a function to start transcription of a target gene in a coryneform bacterium. As suitable examples of such a promoter, the lac promoter, the trc promoter, the tac promoter, etc. can be used in a coryneform bacterium. The promoter used in the present invention may be modified for change in its regulatory mechanism, if needed. The terminator placed downstream of a target gene under a regulatory sequence may also have any base sequence as long as it has a function to terminate transcription of the gene in a coryneform bacterium.

Genes which each encode AHAS, AHAIR, DHAD, KDC, or ADH are expressed on a plasmid or a chromosome in *Corynebacterium glutamicum* as a host. For example, with use of a plasmid, these genes are introduced under a regulatory sequence so as to be expressible. Herein, "under a regulatory sequence" means that cooperative work of these genes with, for example, a promoter, an inducer, an operator, a ribosome binding site and a transcription terminator can achieve transcription and translation. A plasmid vector used for such a purpose may be any plasmid vector as long as it comprises a gene responsible for autonomously replicating function in a coryneform bacterium. Specific examples of the plasmid vector include pAM330 derived from *Brevibacterium lactofermentum* 2256 (JP 58-67699 A; Miwa, K. et al., Cryptic plasmids in glutamic acid-producing bacteria. Agric. Biol. Chem. 48:2901-2903 (1984); and Yamaguchi, R. et al., Determination of the complete nucleotide sequence of the *Brevibacterium lactofermentum* plasmid pAM330 and the analysis of its genetic information. Nucleic Acids Symp. Ser. 16:265-267 (1985)); pHM1519 derived from *Corynebacterium glutamicum* ATCC13058 (Miwa, K. et al., Cryptic plasmids in glutamic acid-producing bacteria. Agric., Biol., Chem. 48:2901-2903 (1984)) and pCRY30 derived from the same (Kurusu, Y. et al., Identification of plasmid partition function in coryneform bacteria. Appl. Environ. Microbiol. 57:759-764 (1991)); pCG4 derived from *Corynebacterium glutamicum* T250 (JP 57-183799 A; and Katsumata, R. et al., Protoplast transformation of glutamate-producing bacteria with plasmid DNA. J. Bacteriol., 159:306-311 (1984)), pAG1, pAG3, pAG14 and pAG50 derived from the same (JP 62-166890 A), and pEK0, pEC5 and pEKEx1 derived from the same (Eikmanns, B. J. et al., A family of *Corynebacterium glutamicum*/*Escherichia coli* shuttle vectors for cloning, controlled gene expression, and promoter probing. Gene, 102: 93-98 (1991)); derivatives thereof; etc. Phage DNA etc. are also included, and any other vector can be used as long as it can replicate itself in a host. The vector preferably comprises a multicloning site which comprises various kinds of restriction enzyme sites inside, or a single restriction enzyme site.

The plasmid vector used for transformation, for example in the case where each of ilvBN, ilvC, and ilvD derived from *Corynebacterium glutamicum*, kivD derived from *Lactococcus* lactis, and adh derived from *Pseudomonas putida* is used, can be constructed by ligating each of the genes whose base sequences have already been confirmed to a suitable regulatory sequence such as promoters and terminators, and subsequently inserting the ligated genes in a suitable restriction enzyme site of one of the above-mentioned plasmid vectors. Details are described in Examples.

Transformation

As the method for introducing a plasmid vector comprising a target gene into *Corynebacterium glutamicum*, any known method may be used without limitation. Examples of the known method include electroporation and the conjugation method. Specifically, an electric pulse method may be performed by a known method (Kurusu, Y. et al., Electroporation-transformation system for Coryne form bacteria by auxotrophic complementation., Agric., Biol. Chem. 54:443-447 (1990); and Vertes A. A. et al., Presence of mrr- and mcr-like restriction systems in Coryneform bacteria. Res. Microbiol. 144:181-185 (1993)).

The above methods may be performed based on a conventional method for gene engineering experiments. Information on vectors of various kinds of microorganisms, such as *Escherichia coli* and actinomycetes, and methods for introduction and expression of exogenous genes are described in many experimental books (for example, Sambrook, J. & Russell, D. W. Molecular Cloning: A Laboratory Manual, 3rd Edition, CSHL Press, 2001; Hopwood, D. A., Bibb, M. J., Charter, K. F., Bruton, C. J., Kieser, H. M., Lydiate, D. J., Smith, C. P., Ward, J. M., Schrempf, H. Genetic manipulation of *Streptomyces*: A Laboratory manual, The John Innes institute, Norwich, UK, 1985; etc.). Therefore, selection of vectors, and introduction and expression of genes can be performed by suitably applying such a method.

Specific examples of the *Corynebacterium glutamicum* transformant created by the above-mentioned method include *Corynebacterium glutamicum* IBU1 (Accession Number NITE BP-718), *Corynebacterium glutamicum* IBU2 (Accession Number NITE BP-719), *Corynebacterium glutamicum* IBU3 (Accession Number NITE BP-720), and *Corynebacterium glutamicum* IBU4 (Accession Number NITE BP-721), all of which were deposited in Incorporated Administrative Agency National Institute of Technology and Evaluation, NITE Patent Microorganisms Depositary (2-5-8 Kazusakamatari, Kisarazu-shi, Chiba 292-0818 Japan) on Mar. 17, 2009, and the acceptance was notified on Mar. 26, 2009.

For improving production of isobutanol, the transformant of the present invention may include genetic modification which leads to one or more characteristics selected from the group consisting of increased flow in glycolytic system, increased resistance to isobutanol, osmotic pressure, or organic acids, and reduced production of by-products (carbon-containing molecules other than the target product). Such genetic modification can be achieved, in particular, by overexpression of an exogenous gene and/or inactivation of an endogenous gene, classic mutagenesis, screening and/or target mutant selection.

A transformant may be mutated by artificial mutagenesis with use of ultraviolet, X-rays, an agent, or the like. Any mutant obtained in such a way may be used as a transformed microorganism of the present invention, as long as it is capable of producing isobutanol, achieving the object of the present invention.

The thus created transformant of *Corynebacterium glutamicum* of the present invention (hereinafter referred to simply as the transformant) may be cultured with use of a culture medium commonly used for culture of microorganisms. The culture medium may be a natural medium or a synthetic medium containing a carbon source, a nitrogen source, inorganic salts, other nutritional substances, etc.

Examples of the carbon source include, for example, carbohydrates and sugar alcohols such as glucose, fructose, sucrose, mannose, maltose, mannitol, xylose, galactose, starch, molasses, sorbitol and glycerol; organic acids such as acetic acid, citric acid, lactic acid, fumaric acid, maleic acid and gluconic acid; and alcohols such as ethanol and propanol. Hydrocarbons, such as normal paraffin, etc. may be used if desired. These carbon sources may be used alone or as a mixture of two or more thereof. The concentration of the carbon source in a culture medium is usually about 0.1 to 10% by weight.

Examples of the nitrogen source include nitrogen compounds including inorganic or organic ammonium compounds such as ammonium chloride, ammonium sulfate, ammonium nitrate, and ammonium acetate; urea; aqueous ammonia; sodium nitrate; and potassium nitrate, but the nitrogen source is not limited thereto. Nitrogen-containing organic compounds such as corn steep liquor, meat extract, peptone, N—Z-amine, protein hydrolysate, amino acid, etc. may be used. These nitrogen sources may be used alone or as a mixture of two or more thereof. The concentration of the nitrogen source in a culture medium varies depending on the kind of the nitrogen compound, but is usually about 0.1 to 10% by weight.

Examples of the inorganic salts include, potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of the inorganic salt in a culture medium varies depending on the kind of the inorganic salt, but is usually about 0.01 to 1.0% by weight.

Examples of the nutritional substances include, meat extract, peptone, poly peptone, yeast extract, dry yeast, corn steep liquor, skim milk powder, defatted soybean hydrochloric acid hydrolysate, and extract from animals, plants or microorganisms, and degradation products thereof. The concentration of the nutritional substance in a culture medium varies depending on the kind of the nutritional substance, but is usually about 0.1 to 10% by weight. Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 5 to 8.

Examples of preferable culture medium for microorganisms include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)) etc.

The culture temperature is about 15 to 45° C., and the culture period is about 1 to 7 days.

Subsequently, cultured bacterial cells of the transformant are collected. The method for collecting and isolating cultured bacterial cells from the culture obtained as described above is not particularly limited, and any known method, such as centrifugal separation and membrane separation, may be used.

The collected bacterial cells may be subjected to some treatment and then the resulting treated bacterial cells may be used in the next step. As long as the cultured bacterial cells have undergone some treatment, they can be used as the treated bacterial cells. Examples of the treated bacterial cells include immobilized bacterial cells obtained by treatment with, for example, acrylamide, carrageenan, or the like.

(II) Process for Producing Isobutanol

The cultured bacterial cells of the transformant collected and isolated from the culture or treated bacterial cells thereof obtained as described above are subjected to isobutanol-producing reaction in a reaction culture medium under reducing conditions. Examples of the treated bacterial cells include immobilized bacterial cells obtained by treatment with, for example, acrylamide, carrageenan, or the like. A process for producing isobutanol comprising a step of having the above-mentioned transformant or treated bacterial cells thereof produce isobutanol in a culture medium containing saccharides (reaction culture medium) and a step of collecting produced isobutanol is also comprised in the present invention.

The process for producing isobutanol may be any of a batch process, a fed-batch process, and a continuous process.

The reaction culture medium may be any culture medium as long as it contains an organic carbon source (for example, saccharides) as a raw material of isobutanol. The organic carbon source may be any substance as long as the transformant of the present invention can utilize the substance for a biochemical reaction. Specific examples of saccharides include monosaccharides such as glucose, xylose, arabinose, galactose, fructose and mannose; disaccharides such as cellobiose, sucrose, lactose and maltose; polysaccharides such as dextrin and soluble starch; etc. In particular, monosaccharides and disaccharides are preferred, monosaccharides are more preferred, and inter alia, glucose is further more preferred. In the present invention, a mixture of two or more kinds of saccharides may also be used. The concentration of the carbon source is preferably about 0.1 to 10% by weight and more preferably about 0.5 to 10% by weight.

The reaction culture medium may further contain ingredients necessary for the transformant or treated transformant to maintain its metabolic functions, that is, carbon sources such as various saccharides; nitrogen sources necessary for protein synthesis; and others including salts of phosphorus, potassium, sodium, etc. and salts of trace metals such as iron, manganese and calcium. The amounts of such ingredients may be suitably determined depending on the necessary reaction time, the target organic compound, or the transformant to be used. Depending on the transformant to be used, addition of certain vitamins may be preferred. The carbon source, the nitrogen source, the inorganic salts, the vitamin, and the trace metal salt to be used may be known ingredients, for example, those illustrated in the step of proliferation and culturing of the transformant.

The pH of the reaction culture medium is preferably about 6 to 8.

The reaction of the transformant or treated bacterial cells thereof with saccharides is preferably performed under temperature conditions in which the transformant of the present invention or treated bacterial cells thereof can work. The temperature may be suitably determined depending on the transformant or treated bacterial cells thereof, etc., and is usually about 25 to 35° C.

The isobutanol production of the present invention is performed under reducing conditions. In the present invention, "reducing conditions" is defined based on the ORP of the reaction culture medium. The ORP of the reaction culture medium is preferably about −100 mV to −500 mV, more preferably about −200 mV to −500 mV. The ORP can be determined with an ORP meter (for example, ORP Electrodes made by BROADLEY JAMES).

The above-mentioned reducing conditions can be obtained by suitably setting the oxygen concentration, temperature, and pH of the reaction culture medium. As for the oxygen concentration, anaerobic conditions can be achieved by hermetically sealing the reaction culture medium or injecting nitrogen gas with subsequent sealing, etc.

One of the characteristics of the isobutanol production process of the present invention is that the transformant used in the reaction culture medium containing saccharides under reducing conditions does not substantially proliferate. The fact that the transformant in the reaction culture medium does not proliferate during isobutanol production can be confirmed by measuring suitably collected reaction medium for isobutanol concentration and bacterial cell concentration (for example, optical density of the bacterial cells) over time.

The culture period is, for example, about 2 to 72 hours.

The isobutanol produced in the reaction culture medium as described above is collected. The collection method may be a well known method used in the bioprocess. Examples of such a known method include distillation, membrane permeation method, organic solvent extraction method, etc. The method for separation, purification and collection may be suitably determined depending on the composition of the reaction mixture, the kinds and amounts of by-products, etc.

EXAMPLES

Hereinafter, the present invention will be illustrated in more detail by Examples, but is not limited thereto.

Example 1

Cloning and Expression of Isobutanol-Producing Genes (1) Extraction of Chromosomal DNA from Microorganisms To extract chromosomal DNA from *Bacillus subtilis* 168 NBRC14144, the bacterium was inoculated in NBRC Medium No. 802 (10 g of polypeptone, 2 g of yeast extract, and 1 g of $MnSO_4.7H_2O$ were dissolved in 1 L of distilled water) with use of a platinum loop, and cultured with shaking at 37° C. until logarithmic growth phase. Then, according to the instruction manual, chromosomal DNA was recovered from the collected cells with use of a DNA extraction kit (trade name: GenomicPrep Cells and Tissue DNA Isolation Kit, made by Amersham).

To extract chromosomal DNA from *Corynebacterium glutamicum* R (FERN P-18976) and total DNA from *Corynebacterium casei* JCM12072, the bacterium was inoculated, with use of a platinum loop, in A Medium (2 g of $(NH_2)_2CO_3$ 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+ 0.042% (w/v) $MnSO_4.2H_2O$, 1 mL of 0.02% (w/v) biotin solution, 2 mL of 0.01% (w/v) thiamin solution, 2 g of yeast extract, and 7 g of vitamin assay casamino acid were dissolved in 1 L of distilled water), which was supplemented with 50% (w/v) glucose as a carbon source to a final concentration of 4%, and cultured with shaking at 33° C. until logarithmic growth phase. Then, according to the instruction manual, chromosomal DNA was recovered from the collected cells with use of a DNA extraction kit (trade name: GenomicPrep Cells and Tissue DNA Isolation Kit, made by Amersham).

To extract chromosomal DNA from *Escherichia coli* K12 MG1655, the bacterium was inoculated in LB Medium (10 g of tryptone, 5 g of yeast extract, and 5 g of NaCl were dissolved in 1 L of distilled water) with use of a platinum loop, and cultured with shaking at 37° C. until logarithmic growth phase. Then, according to the instruction manual, chromosomal DNA was recovered from the collected cells with use of a DNA extraction kit (trade name: GenomicPrep Cells and Tissue DNA Isolation Kit, made by Amersham).

To extract chromosomal DNA from *Lactococcus lactis* NBRC100933, the bacterium was inoculated in MRS Medium (made by DIFCO) with use of a platinum loop, and cultured with shaking at 30° C. until logarithmic growth phase. Then, according to the instruction manual, chromosomal DNA was recovered from the collected cells with use of a DNA extraction kit (trade name: GenomicPrep Cells and Tissue DNA Isolation Kit, made by Amersham).

To extract chromosomal DNA from *Pseudomonas putida* F1 ATCC700007, the bacterium was inoculated in Nutrient Broth Medium (made by DIFCO) with use of a platinum loop, and cultured with shaking at 30° C. until logarithmic growth phase. Then, according to the instruction manual, chromosomal DNA was recovered from the collected cells with use of a DNA extraction kit (trade name: GenomicPrep Cells and Tissue DNA Isolation Kit, made by Amersham).

To extract chromosomal DNA from *Saccharomyces cerevisiae* NBRC2376, the bacterium was inoculated in YM Medium (10 g of glucose, 5 g of peptone, 3 g of yeast extract, and 3 g of malt extract were dissolved in 1 L of distilled water) with use of a platinum loop, and cultured with shaking at 28° C. until logarithmic growth phase. Then, according to the instruction manual, chromosomal DNA was recovered from the collected cells with use of a DNA extraction kit (trade name: GenomicPrep Cells and Tissue DNA Isolation Kit, made by Amersham).

To extract chromosomal DNA from *Staphylococcus epidermidis* NBRC12993, the bacterium was inoculated in NBRC Medium No. 802 (10 g of polypeptone, 2 g of yeast extract, and 1 g of $MnSO_4.7H_2O$ were dissolved in 1 L of distilled water) with use of a platinum loop, and cultured with shaking at 30° C. until logarithmic growth phase. Then, according to the instruction manual, chromosomal DNA was recovered from the collected cells with use of a DNA extraction kit (trade name: GenomicPrep Cells and Tissue DNA Isolation Kit, made by Amersham).

(2) Construction of Cloning Vectors Construction of Cloning Vector pCRB22

A DNA fragment comprising a DNA replication origin sequence of pCASE1, which is a plasmid derived from *Corynebacterium casei* JCM12072 (hereinafter abbreviated as pCASE1-ori) (SEQ ID NO: 1) and a DNA fragment comprising a cloning vector pHSG298 (made by Takara Bio, Inc.) were amplified by the following PCR method.

In the PCR, the following sets of primers were synthesized based on SEQ ID NO: 1 (pCASE1-ori sequence) and SEQ ID NO: 2 (cloning vector pHSG298) for cloning of the pCASE1-ori sequence and the cloning vector pHSG298, and were used.

Primers for pCASE1-Ori Sequence Amplification

```
                                          (SEQ ID NO: 3)
    (a-1):    5'-AT AGATCT AGAACGTCCGTAGGAGC-3'

(SEQ ID NO: 4)
    (b-1):    5'-AT AGATCT GACTTGGTTACGATGGAC-3'
```

Primers (a-1) and (b-1) each have a BglII restriction enzyme site added thereto.

Primers for Cloning Vector pHSG298 Amplification

```
                                          (SEQ ID NO: 5)
    (a-2):    5'-AT AGATCT AGGTTTCCCGACTGGAAAG-3

(SEQ ID NO: 6)
    (b-2):    5'-AT AGATCT CGTGCCAGCTGCATTAATGA-3'
```

Primers (a-2) and (b-2) each have a BglII restriction enzyme site added thereto.

As the template DNA, total DNA extracted from *Corynebacterium casei* JCM12072 obtained from Japan Collection of Microorganisms (JCM) and cloning vector pHSG298 (made by Takara Bio, Inc.) were used.

Actual PCR was performed with use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*$^)$ | 0.5 μL each (final conc.: 1 μM) |
| Sterile distilled water: | 25.5 μL |
| The above ingredients were mixed, and 50 μL of the reaction mixture was subjected to PCR. | |

*$^)$For amplification of the pCASE1-ori sequence, a combination of primers (a-1) and (b-1), and for amplification of the cloning vector pHSG298, a combination of primers (a-2) and (b-2) was used.

PCR Cycle:
Denaturation step: 94° C., 60 seconds
Annealing step: 52° C., 60 seconds
Extension step: 72° C.
pCASE1-ori sequence: 150 seconds
Cloning vector pHSG298: 180 seconds
A cycle consisting of the above 3 steps was repeated 30 times.

Using 10 μL of the above-produced reaction mixture, 0.8% agarose gel electrophoresis was performed. In the case of the pCASE1-ori sequence, an about 1.4-kb fragment was detected. In the case of the cloning vector pHSG298, an about 2.7-kb DNA fragment was detected.

10 μL of the about 1.4-kb DNA fragment comprising the pCASE1-ori sequence; which is a plasmid derived from *Corynebacterium casei* amplified by the above PCR, and 10 μL of the about 2.7-kb DNA fragment comprising the cloning vector pHSG298 were each cut with use of a restriction enzyme BglII and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation. This was named Ligation Liquid A.

With use of the Ligation Liquid A, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 μg/mL of kanamycin.

A growing strain on the culture medium was subjected to liquid culture in the usual manner. Plasmid DNA was extracted from the culture medium and cut with use of a restriction enzyme BglII to confirm the inserted fragment. As a result, in addition to an about 2.7-kb DNA fragment of the cloning vector pHSG298, an about 1.4-kb DNA fragment of pCASE-ori sequence was confirmed.

The plasmid comprising the pCASE1-ori sequence was named pCRB22.

Construction of Cloning Vector pCRB11

A DNA fragment comprising a DNA replication origin sequence of pCG1 (JP 57-134500 A), which is a plasmid replicable in *Corynebacterium glutamicum* (hereinafter abbreviated as pCG1-ori) and a DNA fragment comprising a cloning vector pHSG398 (made by Takara Bio, Inc.) were amplified by the following PCR method.

In the PCR, the following sets of primers were synthesized based on SEQ ID NO: 7 (pCG1-ori sequence) and SEQ ID NO: 8 (cloning vector pHSG398) for cloning of the pCG1-ori sequence and the cloning vector pHSG398, and were used.

Primers for pCG1-Ori Sequence Amplification

```
                                          (SEQ ID NO: 9)
    (a-3):    5'- AT AGATCT AGCATGGTCGTCACAGAG -3'

(SEQ ID NO: 10)
    (b-3):    5'- AT AGATCT GGAACCGTTATCTGCCTATG -3'
```

Primers (a-3) and (b-3) each have a BglII restriction enzyme site added thereto.

Primers for Cloning Vector pHSG398 Amplification

```
                                          (SEQ ID NO: 11)
    (a-4):    5'-AT AGATCT GTCGAACGGAAGATCACTTC-3'

(SEQ ID NO: 12)
    (b-4):    5'-AT AGATCT AGTTCCACTGAGCGTCAG-3'
```

Primers (a-4) and (b-4) each have a BglII restriction enzyme site added thereto.

As the template DNA, pCG1 (JP 57-134500 A) and cloning vector pHSG398 (made by Takara Bio, Inc.) were used.

Actual PCR was performed with use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |

| | |
|---|---|
| dNTP Mixture (2.5 mM each) | 8 µL |
| Template DNA | 5 µL (DNA content: 1 µg or less) |
| The above 2 primers*⁾ | 0.5 µL each (final conc.: 1 µM) |
| Sterile distilled water: | 25.5 µL |
| The above ingredients were mixed, and 50 µL of the reaction mixture was subjected to PCR. | |

*⁾For amplification of the pCG1-ori sequence, a combination of primers (a-3) and (b-3), and for amplification of the cloning vector pHSG398, a combination of primers (a-4) and (b-4) was used.

PCR Cycle:

Denaturation step: 94° C., 60 seconds

Annealing step: 52° C., 60 seconds

Extension step: 72° C.

pCG1-ori sequence: 120 seconds

Cloning vector pHSG398: 150 seconds

A cycle consisting of the above 3 steps was repeated 30 times.

Using 10 µL of the above-produced reaction mixture, 0.8% agarose gel electrophoresis was performed. In the case of the pCG1-ori sequence, an about 1.9-kb fragment was detected. In the case of the cloning vector pHSG398, an about 2.2-kb DNA fragment was detected.

10 µL of the about 1.9-kb DNA fragment comprising the pCG1-ori gene, which is derived from a plasmid pCG1, and 10 µL of the about 2.2-kb DNA fragment comprising the cloning vector pHSG398, both amplified by the above PCR, were each cut with use of a restriction enzyme BglII and processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation. This was named Ligation Liquid B.

With use of the Ligation Liquid B, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 µg/mL of chloramphenicol.

A growing strain on the culture medium was subjected to liquid culture in the usual manner. Plasmid DNA was extracted from the culture medium and cut with use of a restriction enzyme BglII to confirm the inserted fragment. As a result, in addition to an about 2.2-kb DNA fragment of the cloning vector pHSG398, an about 1.9-kb DNA fragment of pCG1-ori sequence was confirmed.

The plasmid comprising the pCG1-ori sequence was named pCRB11.

Construction of Cloning Vector pCRB15

A DNA fragment comprising a cloning vector pCRB11 and a DNA fragment comprising a zeocin resistance gene derived from pSELECT-zeo-mcs (made by Invitrogen Corp.) were amplified by the following PCR method.

In the PCR, the following sets of primers were synthesized based on SEQ ID NO: 13 (pCRB11) and SEQ ID NO: 14 (zeocin resistance gene) for cloning of the cloning vector pCRB11 and the zeocin resistance gene, and were used.

Primers for Cloning Vector pCRB11 Amplification (SEQ ID NO: 15)
(a-5): 5'-AT GATATC CGAAGTGATCTTCCGTTCGA-3'

(SEQ ID NO: 16)
(b-5): 5'-AT GATATC AAGGCAGTTATTGGTGCCCT-3'

Primers (a-5) and (b-5) each have an EcoRV restriction enzyme site added thereto.

Primers for Zeocin Resistance Gene Amplification (SEQ ID NO: 17)
(a-6): 5'-AT GATATC TAGCTTATCCTCAGTCCTGC-3'

(SEQ ID NO: 18)
(b-6): 5'-AT GATATC CCATCCACGCTGTTTTGACA-3'

Primers (a-6) and (b-6) each have an EcoRV restriction enzyme site added thereto.

As the template DNA, cloning vector pCRB11 and pSELECT-zeo-mcs (made by Invitrogen Corp.) were used.

Actual PCR was performed with use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/µL) | 0.5 µL |
| 10× LA PCR ™ Buffer II (Mg²⁺ free) | 5 µL |
| 25 mM MgCl₂ | 5 µL |
| dNTP Mixture (2.5 mM each) | 8 µL |
| Template DNA | 5 µL (DNA content: 1 µg or less) |
| The above 2 primers*⁾ | 0.5 µL each (final conc.: 1 µM) |
| Sterile distilled water: | 25.5 µL |
| The above ingredients were mixed, and 50 µL of the reaction mixture was subjected to PCR. | |

*⁾For amplification of the cloning vector pCRB11 sequence, a combination of primers (a-5) and (b-5), and for amplification of the zeocin resistance gene, a combination of primers (a-6) and (b-6) was used.

PCR cycle:

Denaturation step: 94° C., 60 seconds

Annealing step: 52° C., 60 seconds

Extension step: 72° C.

pCRB11 sequence: 200 seconds

Zeocin resistance gene: 45 seconds

A cycle consisting of the above 3 steps was repeated 30 times.

Using 10 µL of the above-produced reaction mixture, 0.8% agarose gel electrophoresis was performed. In the case of the cloning vector pCRB11 sequence, an about 3.3-kb fragment was detected. In the case of the zeocin resistance gene, an about 0.5-kb DNA fragment was detected.

10 µL of the about 3.3-kb DNA fragment comprising the cloning vector pCRB11 and 10 µL of the about 0.5-kb DNA fragment comprising the zeocin resistance gene derived from a plasmid pSELECT-zeo-mcs, both amplified by the above PCR, were each cut with use of a restriction enzyme EcoRV and processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µl, and the mixture was allowed to react at 15° C. for 3 hours for ligation. This was named Ligation Liquid C.

With use of the Ligation Liquid C, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 25 μg/mL of zeocin.

A growing strain on the culture medium was subjected to liquid culture in the usual manner. Plasmid DNA was extracted from the culture medium and cut with use of a restriction enzyme EcoRV to confirm the inserted fragment. As a result, in addition to an about 3.3-kb DNA fragment derived from the cloning vector pCRB11, an about 0.5-kb DNA fragment was confirmed in the case of the zeocin resistance gene.

The cloning vector comprising the zeocin resistance gene was named pCRB15.

Construction of Cloning Vector pCRB205

A DNA fragment comprising a cloning vector pCRC200 (Yasuda, K. et al., Analyses of the acetate-producing pathways in *Corynebacterium glutamicum* under oxygen-deprived conditions. Applied Microbiology and Biotechnology. 77: 853-860 (2007)) was amplified by the following PCR method.

In the PCR, the following set of primers was synthesized based on SEQ ID NO: 19 (pCRC200) for cloning of the pCRC200, and was used.

Primers for pCRC200 Amplification

```
                                               (SEQ ID NO: 20)
(a-7):  5'-CTCT ACTAGT GTCGAC GGATCC TTGTGTGGAATTG
        TGAGCGG-3'

(SEQ ID NO: 21)
(b-7):  5'-CTCT ACTAGT CATACGAGCCGGAAGCATAA-3'
```

Primer (a-7) has SpeI, SalI, and BamHI restriction enzyme sites added thereto, and primer (b-7) has a SpeI restriction enzyme site added thereto.

As the template DNA, a cloning vector pCRC200 comprising a tac promoter was used.

Actual PCR was performed with use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg²⁺ free) | 5 μL |
| 25 mM MgCl₂ | 5 μL |
| dNTP Mixture (2.5 mM each) | 8 μL |
| Template DNA | 5 μL (DNA content: 1 μg or less) |
| The above 2 primers*⁾ | 0.5 μL each (final conc.: 1 μM) |
| Sterile distilled water: | 25.5 μL |
| The above ingredients were mixed, and 50 μL of the reaction mixture was subjected to PCR. | |

*⁾For amplification of pCR200, a combination of primers (a-7) and (b-7) was used.

PCR Cycle:
Denaturation step: 94° C., 60 seconds
Annealing step: 52° C., 60 seconds
Extension step: 72° C., 300 seconds A cycle consisting of the above 3 steps was repeated 30 times.

Using 10 μL of the above-produced reaction mixture, 0.8% agarose gel electrophoresis was performed, and an about 5.0-kb fragment of the cloning vector pCRC200 was detected.

10 μL of the about 5.0-kb DNA fragment comprising a gene derived from pCRC200, amplified by the above PCR, was cut with use of a restriction enzyme SpeI and processed at 70° C. for 10 minutes for deactivation of the restriction enzyme. To this, 1 μL of T4 DNA ligase 10× buffer solution and 1 unit of T4 DNA ligase (made by Takara Bio, Inc.) were added. Sterile distilled water was added thereto so that the total amount was 10 μL, and the mixture was allowed to react at 15° C. for 3 hours for ligation. This was named Ligation Liquid D.

With use of the Ligation Liquid D, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 μg/mL of chloramphenicol.

A growing strain on the culture medium was subjected to liquid culture in the usual manner. Plasmid DNA was extracted from the culture medium and cut with use of a restriction enzyme SpeI to confirm the inserted restriction enzyme site.

The cloning vector pCRC200 to which restriction enzyme sites SpeI, SalI, and BamHI were added was named pCRB205.

Construction of Cloning Vector pCRB207

A DNA fragment comprising a promoter sequence of the gapA gene (hereinafter abbreviated as PgapA), which encodes the glyceraldehyde-3-phosphate dehydrogenase derived from *Corynebacterium glutamicum* R, and a DNA fragment comprising an rrnBT1T2 bidirectional terminator sequence (hereinafter abbreviated as terminator sequence) derived from a cloning vector pKK223-3 (made by Pharmacia) were amplified by the following method.

In the PCR, the following sets of primers were synthesized based on SEQ ID. NO: 22 (PgapA sequence) and SEQ ID NO: 23 (terminator sequence) for cloning of the PgapA sequence and the terminator sequence, and were used.

Primers for PgapA Sequence Amplification

```
                                               (SEQ ID NO: 24)
(a-8):  5'-CTCT GTCGAC CCGAAGATCTGAAGATTCCTG-3'

(SEQ ID NO: 25)
(b-8):  5'-CTCT GTCGAC GGATCC CCATGG TGTGTCTCCTCT
        AAAGATTGTAGG-3'
```

Primer (a-8) has a SalI restriction enzyme site added thereto, and primer (b-8) has SalI, BamHI, and NcoI restriction enzyme sites added thereto.

Primers for Terminator Sequence Amplification

```
                                               (SEQ ID NO: 26)
(a-9):  5'-CTCT GCATGC CCATGG CTGTTTTGGCGGATGAGAG
        A-3'

(SEQ ID NO: 27)
(b-9):  5'-CTCT GCATGC TCATGA AAGAGTTTGTAGAAACGCA
        AAAAGG-3
```

Primer (a-9) has SphI and NcoI restriction enzyme sites added thereto, and primer (b-9) has SphI and BspHI restriction enzyme sites added thereto.

As the template DNA, chromosomal DNA extracted from *Corynebacterium glutamicum* R (FERN P-18976) and a plasmid pKK223-3 (made by Pharmacia) were used.

Actual PCR was performed with use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*) | 0.5 μL each (final conc.: 1 μM) |
| Sterile distilled water: | 25.5 μL |
| The above ingredients were mixed, and 50 μL of the reaction mixture was subjected to PCR. | |

*) For amplification of the PgapA sequecne, a combination of primers (a-8) and (b-8), and for amplification of the terminator sequence, a combination of primers (a-9) and (b-9) was used.

PCR Cycle:
  Denaturation step: 94° C., 60 seconds
  Annealing step: 52° C., 60 seconds
  Extension step: 72° C.
  PgapA sequence: 45 seconds
  Terminator sequence: 30 seconds
  A cycle consisting of the above 3 steps was repeated 30 times.

Using 10 μL of the above-produced reaction mixture, 0.8% agarose gel electrophoresis was performed. In the case of the PgapA sequence, an about 0.6-kb fragment was detected. In the case of the terminator sequence, an about 0.4-kb DNA fragment was detected.

10 μL of the about 0.6-kb DNA fragment comprising the PgapA sequence derived from *Corynebacterium glutamicum* R amplified by the above PCR, and 10 μL of the about 4.1-kb cloning vector pCRB22 were each cut with use of a restriction enzyme SalI and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation. This was named Ligation Liquid E.

With use of the Ligation Liquid E, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 μg/mL of kanamycin.

A growing strain on the culture medium was subjected to liquid culture in the usual manner. Plasmid DNA was extracted from the culture medium and cut with use of a restriction enzyme SalI to confirm the inserted fragment. As a result, in addition to an about 4.1-kb DNA fragment of the cloning vector pCRB22, an about 0.6-kb fragment of PgapA sequence was confirmed.

The cloning vector comprising the PgapA sequence was named pCRB206.

10 μL of the about 0.4-kb DNA fragment comprising the terminator sequence derived from a plasmid pKK223-3 amplified by the above PCR, was cut with use of restriction enzymes NcoI and BspHI, and 2 μL of the above-mentioned cloning vector pCRB206 was cut with use of a restriction enzyme NcoI. Then, both were processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation. This was named Ligation Liquid F.

With use of the Ligation Liquid F, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 μg/mL of kanamycin.

A growing strain on the culture medium was subjected to liquid culture in the usual manner. Plasmid DNA was extracted from the culture medium and cut with use of a restriction enzyme to confirm the inserted fragment. As a result, in addition to an about 4.7-kb DNA fragment of the cloning vector pCRB206, an about 0.4-kb DNA fragment of the terminator sequence was confirmed.

The cloning vector comprising the rrnBT1T2 terminator sequence was named pCRB207.

Construction of Cloning Vector pCRB208

A DNA fragment comprising a promoter sequence of the ldhA gene (hereinafter abbreviated as PldhA), which encodes the L-lactate dehydrogenase derived from *Corynebacterium glutamicum* R, was amplified by the following method.

In the PCR, the following set of primers was synthesized based on SEQ ID NO: 28 (PldhA sequence) for cloning of the PldhA sequence, and was used.

Primers for PldhA Sequence Amplification

```
                                      (SEQ ID NO: 29)
(a-10):  5'-CTCT GTCGAC CGGAACTAGCTCTGCAATGA-3'

(SEQ ID NO: 30)
(b-10):  5'-CTCT GTCGAC GGATCC CATATG CGATCCCACTT
         CCTGATTTC-3'
```

Primer (a-10) has a SalI restriction enzyme site added thereto, and primer (b-10) has SalI, BamHI, and NcoI restriction enzyme sites added thereto.

As the template DNA, the chromosomal DNA extracted from *Corynebacterium glutamicum* R (FERN P-18976) was used.

Actual PCR was performed with use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*) | 0.5 μL each (final conc.: 1 μM) |
| Sterile distilled water: | 25.5 μL |
| The above ingredients were mixed, and 50 μL of the reaction mixture was subjected to PCR. | |

*) For amplification of the PldhA sequence, a combination of primers (a-10) and (b-10) was used.

PCR Cycle:
  Denaturation step: 94° C., 60 seconds
  Annealing step: 52° C., 60 seconds
  Extension step: 72° C., 30 seconds
  A cycle consisting of the above 3 steps was repeated 30 times.

Using 10 μL of the above-produced reaction mixture, 0.8% agarose gel electrophoresis was performed, and an about 0.4-kb fragment of the PldhA sequence was detected.

10 μL of the about 0.4-kb DNA fragment comprising the PldhA sequence derived from *Corynebacterium glutamicum* R amplified by the above PCR, and 2 μL of about 4.1-kb DNA fragment comprising the cloning vector pCRB22 were each cut with use of a restriction enzyme SalI and processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation. This was named Ligation Liquid G.

With use of the Ligation Liquid G, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 µg/mL of kanamycin.

A growing strain on the culture medium was subjected to liquid culture in the usual manner. Plasmid DNA was extracted from the culture medium and cut with use of a restriction enzyme SalI to confirm the inserted fragment. As a result, in addition to an about 4.1-kb DNA fragment of the cloning vector pCRB22, an about 0.4-kb DNA fragment of PldhA sequence was confirmed.

The cloning vector comprising the PldhA sequence was named pCRB208.

(3) Cloning of Isobutanol-Producing Genes Cloning of Isobutanol-Producing Gene Derived from Bacillus subtilis A DNA fragment comprising the alsS gene which encodes acetohydroxy acid synthase derived from *Bacillus subtilis* was amplified by the PCR method as described below.

In the PCR, the following set of primers was synthesized based on SEQ ID NO: 31 (the alsS gene of *Bacillus subtilis*) with use of "394 DNA/RNA Synthesizer" made by Applied Biosystems for cloning of the alsS gene, and was used.

Primer Set for alsS Gene Amplification

```
                                            (SEQ ID NO: 32)
(a-11):     5'-CTCT CCATGG TGACAAAAGCAACAAAAGAACAAA
            AATCC-3'

(SEQ ID NO: 33)
(b-11):     5'-CTCT CCATGG AGATCT CTAGAGAGCTTTCGTTT
            TCATGAG-3'
```

Primer (a-11) has an NcoI restriction enzyme site added thereto, and primer (b-11) has NcoI and BglII restriction enzyme sites added thereto.

Cloning of Isobutanol-Producing Genes Derived from Corynebacterium glutamicum

A DNA fragment comprising the ilvB-ilvN gene which encodes acetohydroxy acid synthase, a DNA fragment comprising the ilvC gene which encodes acetohydroxy acid isomeroreductase, and a DNA fragment comprising the ilvD gene which encodes dihydroxy acid dehydratase, derived from *Corynebacterium glutamicum*, were amplified by the PCR method as described below.

In the PCR, the following sets of primers were synthesized based on SEQ ID NO: 34 (the ilvB-ilvN-ilvC gene of *Corynebacterium glutamicum*) and SEQ ID NO: 35 (the ilvD gene of *Corynebacterium glutamicum*) with use of "394 DNA/RNA Synthesizer" made by Applied Biosystems for cloning of the ilvB-ilvN-ilvC gene and the ilvD gene, and were used.

Primers for ilvB-ilvN-ilvC Gene Amplification

```
                                            (SEQ ID NO: 36)
(a-12):     5'-GA CCCGGG AGTAAAGGAGCCAGAAAGTCGTGAA-3'

(SEQ ID NO: 37)
(b-12):     5'-GA CCCGGG CCTGCAGG TGCCTTATGTACAAAGTGC
            ACAGCA-3'
```

Primer (a-12) has a SmaI restriction enzyme site added thereto, and primer (b-12) has SmaI and Sse8387I restriction enzyme sites added thereto.

Primers for ilvD Gene Amplification

```
                                            (SEQ ID NO: 38)
(a-13):     5'-CTCT TCATGA TCCCACTTCGTTCAAAAGTC-3'

(SEQ ID NO: 39)
(b-13):     5'-CTCT TCATGA TTAGTCGACCTGACGGAC-3'
```

Primers (a-13) and (b-13) each have a BspHI restriction enzyme site added thereto.

Cloning of Isobutanol-Producing Gene Derived from Escherichia coli

A DNA fragment comprising the adhP gene which encodes alcohol dehydrogenase derived from *Escherichia coli* was amplified by the PCR method as described below.

In the PCR, the following set of primers was synthesized based on SEQ ID NO: 40 (the adhP gene of *Escherichia coli*) with use of "394 DNA/RNA Synthesizer" made by Applied Biosystems for cloning of the adhP gene, and was used.

Primer Set for adhP Gene Amplification

```
                                            (SEQ ID NO: 41)
(a-14):     5'-CTCT CCATGG AGGCTGCAGTTGTTACGAAG-3'

(SEQ ID NO: 42)
(b-14):     5'-CTCT CCATGG AGATCT TTAGTGACGGAAATCA
            ATCACCAT-3'
```

Primer (a-14) has an NcoI restriction enzyme site added thereto, and primer (b-14) has NcoI and BglII restriction enzyme sites added thereto.

Cloning of a Group of Isobutanol-Producing Genes Derived from Lactococcus lactis A DNA fragment comprising the kivD gene which encodes 2-keto acid decarboxylase derived from *Lactococcus lactis* was amplified by the PCR method as described below.

In the PCR, the following set of primers was synthesized based on SEQ ID NO: 43 (the kivD gene of *Lactococcus lactis*) with use of "394 DNA/RNA Synthesizer" made by Applied Biosystems for cloning of the kivD gene, and was used.

Primer Set for kivD Gene Amplification

```
                                            (SEQ ID NO: 44)
(a-15):     5'-CTCT CCATGG ATACAGTAGGAGATTACCTATTA
            GAC-3'

(SEQ ID NO: 45)
(b-15):     5'-CTCT CCATGG AGATCT TTATGATTTATTTTGT
            TCAGCAAATAGTTTGCC-3'
```

Primer (a-15) has an NcoI restriction enzyme site added thereto, and primer (b-15) has NcoI and BglII restriction enzyme sites added thereto.

Cloning of Isobutanol-Producing Gene Derived from Pseudomonas putida

A DNA fragment comprising the adh gene which encodes alcohol dehydrogenase derived from *Pseudomonas putida* was amplified by the PCR method as described below.

In the PCR, the following set of primers was synthesized based on SEQ ID NO: 46 (the adh gene of *Pseudomonas putida*) with use of "394 DNA/RNA Synthesizer" made by Applied Biosystems for cloning of the adh gene, and was used.

Primers for adh Gene Amplification

```
(a-16):    5'-CTCT TCATGA AAGCTGCTGTCGTTGC-3'        (SEQ ID NO: 47)

(b-16):    5'-CTCT TCATGA CTCGAG TCAGCCTTCGAACTGTA   (SEQ ID NO: 48)
           TCAC-3'
```

Primer (a-16) has a BspHI restriction enzyme site added thereto, and primer (b-16) has BspHI and XhoI restriction enzyme sites added thereto.

Cloning of Isobutanol-Producing Gene Derived from Saccharomyces cerevisiae

A DNA fragment comprising the adh2 gene which encodes alcohol dehydrogenase derived from *Saccharomyces cerevisiae* was amplified by the PCR method as described below.

In the PCR, the following set of primers was synthesized based on SEQ ID NO: 49 (the adh2 gene of *Saccharomyces cerevisiae*) with use of "394 DNA/RNA Synthesizer" made by Applied Biosystems for cloning of the adh2 gene, and was used.

Primers for adh2 Gene Amplification

```
(a-17):    5'-CTCT CCATGG CTATTCCAGAAACTCAAAAGCCA    (SEQ ID NO: 50)
           TTAT-3'

(b-17):    5'-CTCT CCATGG AGATCT TTATTTAGAAGTGTCAA   (SEQ ID NO: 51)
           CAACGTATCTAC-3
```

Primer (a-17) has an NcoI restriction enzyme site added thereto, and primer (b-17) has NcoI and BglII restriction enzyme sites added thereto.

Cloning of a Group of Isobutanol-Producing Genes Derived from Staphylococcus epidermidis A DNA fragment comprising the ipd gene (locus tag: NP_765765) which encodes 2-keto acid decarboxylase (also known as indole-3-pyruvate decarboxylase) derived from *Staphylococcus epidermidis* was amplified by the PCR method as described below.

In the PCR, the following set of primers was synthesized based on SEQ ID NO: 52 (ipd gene of *Staphylococcus epidermidis*) for cloning of the ipd gene, and was used.

Primers for ipd Gene Amplification

```
(a-18):    5'-CTCT CCATGG AACAACGCGTAGGACAATATTTA    (SEQ ID NO: 53)
           ATG-3'

(b-18):    5'-CTCT CCATGG AGATCT TTAAGATGATTTGTTT    (SEQ ID NO: 54)
           TGTGATGCGAATG-3
```

Primer (a-18) has an NcoI restriction enzyme site added thereto, and primer (b-18) has NcoI and BglII restriction enzyme sites added thereto.

The template DNAs used are as follows. For *Bacillus subtilis*, the chromosomal DNA extracted from *Bacillus subtilis* 168 NBRC14144 obtained from NITE Biological Resource Center (NBRC) was used. For *Corynebacterium glutamicum*, the chromosomal DNA extracted from *Corynebacterium glutamicum* R was used. For *Escherichia coli*, the chromosomal DNA extracted from *Escherichia coli* K12 MG1655 was used. For *Lactococcus lactis*, the chromosomal DNA extracted from *Lactococcus lactis* NBRC100933 obtained from NITE Biological Resource Center (NBRC) was used. For *Saccharomyces cerevisiae*, the chromosomal DNA extracted from *Saccharomyces cerevisiae* NBRC 2376 obtained from NITE Biological Resource Center (NBRC) was used. For *Staphylococcus epidermidis*, the chromosomal DNA extracted from *Staphylococcus epidermidis* NBRC12993 obtained from NITE Biological Resource Center (NBRC) was used. For *Pseudomonas putida*, the chromosomal DNA extracted from *Pseudomonas putida* F1 ATCC700007 obtained from American Type Culture Collection (ATCC) was used.

Actual PCR was performed with use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*⁾ | 0.5 μL each (final conc.: 1 μM) |
| Sterile distilled water: | 25.5 μL |

The above ingredients were mixed, and 50 μL of the reaction mixture was subjected to PCR.

*⁾For amplification of the alsS gene of *Bacillus subtilis*, a combination of primers (a-11) and (b-11); for amplification of the ilvB-ilvN-ilvC gene of *Corynebacterium glutamicum*, a combination of primers (a-12) and (b-12); for amplification of the ilvD gene of *Corynebacterium glutamicum*, a combination of primers (a-13) and (b-13); for amplification of the adhP gene of *Escherichia coli*, a combination of primers (a-14) and (b-14); for amplification of the kivD gene of *Lactococcus lactis*, a combination of primers (a-15) and (b-15); for amplification of the adh gene of *Pseudomonas putida*, a combination of primers (a-16) abd (b-16); for amplification of the adh2 gene of *Saccharomyces cerevisiae*, a combination of primers (a-17) and (b-17); and for amplification of the ipd gene of *Staphylococcus epidermidis*, a combination of primers (a-18) and (b-18) were used.

PCR Cycle:

Denaturation step: 94° C., 60 seconds
Annealing step: 52° C., 60 seconds
Extension step: 72° C.
  *Bacillus subtilis* alsS gene: 120 seconds
  *Corynebacterium glutamicum* ilvB-ilvN-ilvC gene: 240 seconds
  *Corynebacterium glutamicum* ilvD gene: 120 seconds
  *Escherichia coli* adhP gene: 60 seconds
  *Lactococcus lactis* kivD gene 120 seconds
  *Pseudomonas putida* adh gene: 60 seconds
  *Saccharomyces cerevisiae* adh2 gene: 70 seconds
  *Staphylococcus epidermidis* ipd gene: 120 seconds A cycle consisting of the above 3 steps was repeated 30 times.

Using 10 μL of each of the above produced reaction mixtures, 0.8% agarose gel electrophoresis was performed. Detected were, about a 1.8-kb DNA fragment in the case of the alsS gene of *Bacillus subtilis*, about a 3.7-kb DNA fragment in the case of the ilvB-ilvN-ilvC gene of *Corynebacterium glutamicum*, about a 2.0-kb DNA fragment in the case of the ilvD gene of *Corynebacterium glutamicum*, about a 1.0-kb DNA fragment in the case of the adhP gene of *Escherichia coli*, about a 1.7-kb DNA fragment in the case of the kivD gene of *Lactococcus lactis*, about a 1.0-kb DNA fragment in the case of the adh gene of *Pseudomonas putida*, about a 1.1-kb DNA fragment in the case of the adh2 gene of *Saccharomyces cerevisiae*, and about a 1.7-kb DNA fragment in the case of the ipd gene of *Staphylococcus epidermidis*.

(4) Construction of Isobutanol-Production Gene Expression Plasmids

Cloning of Isobutanol-Production Gene to pKK223-3

10 µL of the about 3.7-kb DNA fragment comprising the ilvB-ilvN-ilvC gene derived from *Corynebacterium glutamicum* amplified by the PCR in the above (3) and 2 µL of the cloning vector pKK233-3 (made by Pharmacia) comprising a tac promoter were each cut with use of a restriction enzyme SmaI and processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µL and the mixture was allowed to react at 15° C. for 3 hours for ligation. This was named Ligation Liquid H.

With use of the Ligation Liquid H, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 µg/mL of ampicillin.

A growing strain on the culture medium was subjected to liquid culture in the usual manner. Plasmid DNA was extracted from the culture medium and cut with use of a restriction enzyme SmaI to confirm the inserted fragment. As a result, in addition to an about 4.6-kb DNA fragment of the plasmid pKK223-3, an about 3.7-kb inserted fragment was confirmed in the case of the ilvB-ilvN-ilvC gene derived from *Corynebacterium glutamicum* (Ligation Liquid H).

The plasmid comprising the ilvB-ilvN-ilvC gene derived from *Corynebacterium glutamicum* was named pKK223-3-ilvB-ilvN-ilvC/CG.

Cloning of Isobutanol-Production Gene to pCRB1

From the above plasmid pKK223-3-ilvB-ilvN-ilvC/CG, a DNA fragment comprising the tac promoter and the ilvB-ilvN-ilvC gene derived from *Corynebacterium glutamicum* R was amplified by the PCR method as described below.

In the PCR, the following set of primers was synthesized based on the tac promoter and the ilvB-ilvN-ilvC gene derived from *Corynebacterium glutamicum* (SEQ ID NO: 55 (Ptac-ilvB-ilvN-ilvC sequence)), and was used.

Primers for Ptac-ilvB-ilvN-ilvC Sequence Amplification (a-19):  5'-AT GCAAGC TTCGGCTGTGCAGGTCGTAAAT-3'  (SEQ ID NO: 56)

(b-19):  5'-AC GCAAGC TTCGCTTATGTACAAAGTGCAC-3'  (SEQ ID NO: 57)

Primers (a-19) and (b-19) each have a HindIII restriction enzyme site added thereto.

As the template DNA, the above-mentioned plasmid pKK223-3-ilvB-ilvN-ilvC/CG was used.

Actual PCR was performed with use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/µL) | 0.5 µL |
| 10× LA PCR ™ Buffer II (Mg²⁺ free) | 5 µL |
| 25 mM MgCl$_2$ | 5 µL |
| dNTP Mixture (2.5 mM each) | 8 µL |
| Template DNA | 5 µL (DNA content: 1 µg or less) |
| The above 2 primers*⁾ | 0.5 µL each (final conc.: 1 µM) |
| Sterile distilled water: | 25.5 µL |
| The above ingredients were mixed, and 50 µL of the reaction mixture was subjected to PCR. | |

*⁾For amplification of the Ptac-ilvB-ilvN-ilvC sequence, a combination of primers (a-19) and (b-19) was used.

PCR Cycle:
  Denaturation step: 94° C., 60 seconds
  Annealing step: 52° C., 60 seconds
  Extension step: 72° C., 240 seconds
  A cycle consisting of the above 3 steps was repeated 30 times.

Using 10 µL of the above-produced reaction mixture, 0.8% agarose gel electrophoresis was performed, and an about 3.9-kb fragment of the Ptac-ilvB-ilvN-ilvC sequence was detected.

10 µL of the about 3.9-kb DNA fragment comprising the tac promoter sequence and the ilvB-ilvN-ilvC sequence derived from *Corynebacterium glutamicum* R amplified by the above PCR, and 2 µL of about 4.1-kb cloning vector pCRB1 (Nakata, K. et al., Vectors for the genetics engineering of corynebacteria; in Saha, B. C. (ed.) Fermentation Biotechnology, ACS Symposium Series 862. Washington, American Chemical Society: 175-191 (2003)) were each cut with use of a restriction enzyme HindIII and processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation. This was named Ligation Liquid I.

With use of the Ligation Liquid I, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 µg/mL of chloramphenicol.

A growing strain on the culture medium was subjected to liquid culture in the usual manner. Plasmid DNA was extracted from the culture medium and cut with use of a restriction enzyme HindIII to confirm the inserted fragment. As a result, in addition to an about 4.1-kb DNA fragment of the cloning vector pCRB1, an about 3.9-kb DNA fragment was confirmed in the case of the Ptac-ilvB-ilvN-ilvC sequence (Ligation Liquid I).

The plasmid comprising the ilvB-ilvN-ilvC gene derived from *Corynebacterium glutamicum* was named pCRB1-ilvB-ilvN-ilvC/CG (FIG. 1).

Cloning of Isobutanol-Production Gene to pCRB207

10 µL of the about 1.8-kb DNA fragment comprising the alsS gene derived from *Bacillus subtilis*, the about 1.0-kb DNA fragment comprising the adhP gene derived from *Escherichia coli*, the about 1.7-kb DNA fragment comprising the kivD gene derived from *Lactococcus lactis*, the about 1.1-kb DNA fragment comprising the adh2 gene derived from *Saccharomyces cerevisiae*, or the about 1.7-kb DNA fragment comprising the ipd gene derived from *Staphylococcus epidermidis* amplified by the PCR in the above (3) and 2 µL of the cloning vector pCRB207 comprising a PgapA promoter were each cut with use of a restriction enzyme NcoI and processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation. Thus obtained were named Ligation Liquids J, K, L, M, and N.

Similarly, 10 µL of the about 2.0-kb DNA fragment comprising the ilvD gene derived from *Corynebacterium glutamicum* or the about 1.0-kb DNA fragment comprising the adh gene derived from *Pseudomonas putida* amplified by the PCR in the above (3) was each cut with use of a restriction enzyme BspHI, and 2 µL of the cloning vector pCRB207 comprising a PgapA promoter was cut with use of a restriction enzyme NcoI. After deactivation of the restriction enzyme at 70° C. for 10 minutes, both were mixed, and 1 µl of T4 DNA ligase 10× buffer solution and 1 unit of T4 DNA ligase (made by Takara Bio, Inc.) were added thereto. Sterile distilled water was added thereto so that the total amount was 10 µl, and the mixture was allowed to react at 15° C. for 3 hours for ligation. Thus obtained were named Ligation Liquids O and P.

With use of each of the obtained seven kinds of Ligation Liquids J, K, L, M, N, O, and P, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 µg/mL of kanamycin.

A growing strain on the culture medium was subjected to liquid culture in the usual manner. Plasmid DNA was extracted from the culture medium and cut with use of restriction enzymes to confirm the inserted fragments. As a result, in addition to an about 5.1-kb DNA fragment of the plasmid pCRB207, confirmed was an about 1.8-kb inserted fragment comprising the alsS gene derived from *Bacillus subtilis* (Ligation Liquid J), an about 1.0-kb inserted fragment comprising the adhP gene derived from *Escherichia coli* (Ligation Liquid K), an about 1.7-kb inserted fragment comprising the kivD gene derived from *Lactococcus lactis* (Ligation Liquid L), an about 1.1-kb inserted fragment comprising the adh2 gene derived from *Saccharomyces cerevisiae* (Ligation Liquid M), an about 1.7-kb inserted fragment comprising the ipd gene derived from *Staphylococcus epidermidis* (Ligation Liquid N), an about 2.0-kb inserted fragment comprising the ilvD gene derived from *Corynebacterium glutamicum* (Ligation Liquid O), or an about 1.0-kb inserted fragment comprising the adh gene derived from *Pseudomonas putida* (Ligation Liquid P).

The plasmid comprising the alsS gene derived from *Bacillus subtilis* was named pCRB207-alsS/BS, the plasmid comprising the adhP gene derived from *Escherichia coli* was named pCRB207-adhP/EC, the plasmid comprising the kivD gene derived from *Lactococcus lactis* was named pCRB207-kivD/LL, the plasmid comprising the adh2 gene derived from *Saccharomyces cerevisiae* was named pCRB207-adh2/SC, the plasmid comprising the ipd gene derived from *Staphylococcus epidermidis* was named pCRB207-ipd/SE, the plasmid comprising the ilvD gene derived from *Corynebacterium glutamicum* was named pCRB207-ilvD/CG, and the plasmid comprising the adh gene derived from *Pseudomonas putida* was named pCRB207-adh/PP (FIG. 1).

(5) Construction of Strain for Butanol-Production Gene Activity Measurement

With use of one of the above plasmids pCRB1-ilvB-ilvN-ilvC/CG, transformation of *Corynebacterium glutamicum* R ldhA mutant (J. Mol. Microbiol. Biotechnol., Vol. 8, 243-254 (2004)) was performed by the electric pulse method (Agric. Biol. Chem., Vol. 54, 443-447 (1990) and Res. Microbiol., Vol. 144, 181-185 (1993)), and the strain was applied to A agar medium containing 5 µg/mL of chloramphenicol.

With use of each of the seven kinds of the above plasmids pCRB207-alsS/BS, pCRB207-adhP/EC, pCRB207-kivD/LL, pCRB207-adh2/SC, pCRB207-ipd/SE, pCRB207-ilvD/CG, and pCRB207-adh/PP, transformation of *Corynebacterium glutamicum* R ldhA mutant (J. Mol. Microbiol. Biotechnol., Vol. 8, 243-254 (2004)) was performed by the electric pulse method (Agric. Biol. Chem., Vol. 54, 443-447 (1990) and Res. Microbiol., Vol. 144, 181-185 (1993)), and the strain was applied to A agar medium containing 50 µg/mL of kanamycin.

A growing strain on the culture medium was subjected to liquid culture in the usual manner. Plasmid DNA was extracted from the culture medium and cut with use of restriction enzymes to confirm the inserted fragments. As a result, introduction of the above-prepared plasmids pCRB1-ilvB-ilvN-ilvC/CG-ilvD/CG, pCRB207-alsS/BS, pCRB207-adhP/EC, pCRB207-kivD/LL, pCRB207-adh2/SC, pCRB207-ipd/SE, pCRB207-ilvD/CG, and pCRB207-adh/PP was confirmed.

The obtained strains were named *Corynebacterium glutamicum* R ldhA mutant/pCRB1-ilvB-ilvN-ilvC/CG, ldhA mutant/pCRB207-alsS/BS, ldhA mutant/pCRB207-adhP/EC, ldhA mutant/pCRB207-kivD/LL, ldhA mutant/pCRB207-adh2/SC, ldhA mutant/pCRB207-ipd/SE, ldhA mutant/pCRB207-ilvD/CG, and ldhA mutant/pCRB207-adh/PP.

Example 2

Enzyme Activity Measurement in Corynebacterium glutamicum to Which Isoisobutanol-Producing Gene has Introduced The activity of isoisobutanol production-related enzymes, namely acetohydroxy acid synthase (AHAS), acetohydroxy acid isomeroreductase (AHAIR), dihydroxy acid dehydratase (DHAD), 2-keto acid decarboxylase (KDC), and alcohol dehydrogenase (ADH), in *Corynebacterium glutamicum* R ldhA mutant into which one of the isoisobutanol-producing genes constructed in Example 1 had been introduced (hereinafter referred to as *Corynebacterium glutamicum* single-gene transgenic strain) (however, ilvB, ilvN, and ilvC are ligated to each other on the same plasmid as a special case) was measured by the following methods. As a control, the *Corynebacterium glutamicum* R ldhA mutant used as a host was also measured for the activity in the similar way.

(1) Activity Measurement of AHAS, AHAIR, DHAD, and ADH

*Corynebacterium glutamicum* single-gene transgenic strain was applied to A agar medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4 \cdot 7H_2O$, 1 mL of 0.06% (w/v) $Fe_2SO_4 \cdot 7H_2O + 0.042\%$ (w/v) $MnSO_4 \cdot 2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar suspended in 1 L of distilled water) containing 50 µg/mL of kanamycin, and left stand in the dark at 28° C. for 20 hours.

An inoculation loop of the *Corynebacterium glutamicum* single-gene transgenic strain grown on a plate as above was inoculated in a test tube containing 10 mL of A liquid medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4 \cdot 7H_2O$, 1 mL of 0.06% (w/v) $Fe_2SO_4 \cdot 7H_2O$+0.042% (w/v) $MnSO_4 \cdot 2H_2O$, 1 mL of 0.02% (w/v) biotin solution, 2 mL of 0.01% (w/v) thiamin solution, 2 g of yeast extract, 7 g of vitamin assay casamino acid, and 40 g of glucose suspended in 1 L of distilled water) containing 50 μg/mL of kanamycin, and aerobically cultured with shaking at 28° C. for 15 hours.

The *Corynebacterium glutamicum* single-gene transgenic strain grown in the above conditions was inoculated in 100 mL of A liquid medium containing 50 μg/mL of kanamycin, and aerobically cultured with shaking at 28° C. for 15 hours. *Corynebacterium glutamicum* R ldhA mutant was cultured in the same conditions except that the A medium did not contain kanamycin.

The bacterial cells cultured and proliferated as above were collected by centrifugation (8,000×g at 4° C. for 10 minutes). The obtained bacterial cells were washed with Homogenate 1 (100 mM tris-hydrochloric acid buffer solution at pH 7.5, 2 mM dithiothreitol). Centrifugation was performed again, and then the collected bacterial cells were suspended in 1 mL of Homogenate 1. To this, 1 g of glass beads were added and homogenized with an ultrasonic disruptor (Bioruptor made by Cosmo Bio) for 30 minutes. Then, centrifugation (15,000×g at 4° C. for 10 minutes) was performed to remove insoluble substances, and Enzyme Liquid 1 was thus obtained. The protein content was determined with. Bio-Rad protein assay (made by Bio-Rad). With use of the thus obtained enzyme liquid, the activity of AHAS, AHAIR, DHAD, and ADH were determined by the methods shown below.

For measuring the AHAS activity, pyruvic acid was used as a substrate, and decrease in absorbance at 333 nm associated with the decrease in pyruvic acid was used as an index (Craig M. et. al., Mutagenesis of *Escherichia coli* acetohydroxyacid synthase isoenzyme II and characterization of three herbicide-insensitive forms. Biochem. J., 335: 653-661 (1998)). The reaction mixture used for the activity measurement was composed of 50 mM potassium phosphate at pH 8.0, 10 mM magnesium chloride, 0.1 mM TPP, 0.1 mM FAD, and 50 mM sodium pyruvate, and spectrophotometer DU-800 (made by BECKMAN) was used for the absorption spectrometry. To the reaction mixture, Enzyme Liquid 1 was added at 30° C., and the mixture was left stand for 10 minutes. Then, sodium pyruvate was added thereto to the concentration of 50 mM. From the difference of the slope of decrease in absorbance between the reaction mixture and a reaction mixture without sodium pyruvate, the activity value was calculated with use of molar absorbance coefficient of 17.5 $M^{-1}cm^{-1}$.

The results of AHAS activity measurement of *Corynebacterium glutamicum* R ldhA mutant/pCRB1-ilvB-ilvN-ilvC/CG and ldhA mutant/pCRB207-alsS/BS, both of which were constructed in Example 1 by introducing an AHAS-encoding gene thereinto, and of *Corynebacterium glutamicum* R ldhA mutant used as a control are shown in the table below (1 U means the amount of enzyme which consumes 1 μmol of substrate per minute).

TABLE 1

| *Corynebacterium glutamicum* AHAS recombinant strain activity measurement | | |
|---|---|---|
| Strain | | AHAS activity |
| Plasmid | Introduced gene | (U/mg-protein) |
| pCRB1-ilvB-ilvN-ilvC/CG | ilvBN (*Corynebacterium glutamicum* R) | 1.15 |

TABLE 1-continued

| *Corynebacterium glutamicum* AHAS recombinant strain activity measurement | | |
|---|---|---|
| Strain | | AHAS activity |
| Plasmid | Introduced gene | (U/mg-protein) |
| pCRB207-alsS/BS | alsS (*Bacillus subtilis*) | 1.26 |
| *Corynebacterium glutamicum* R ldhA mutant | | 0.07 |

For measuring the AHAIR activity, decrease in absorbance at 340 nm associated with the decrease in NADPH during the formation of 2,3-dihydroxyisovaleric acid from acetolactic acid and NADPH was used as an index (Ruyex., et. al., Characterization of enzymes of the branched-chain amino acid biosynthetic pathway in *Methanococcus* spp. J. Bacteriol., 173: 2086-2092 (1991)). The reaction mixture used for the activity measurement was composed of 100 mM tris-hydrochloric acid buffer solution at pH 7.6, 10 mM magnesium chloride, 0.15 mM NADPH, and 10 mM acetolactic acid, and spectrophotometer DU-800 (made by BECKMAN) was used for the absorption spectrometry. To the reaction mixture, Enzyme Liquid 1 was added at 30° C. to start the reaction. From the difference of the slope of decrease in absorbance between the reaction mixture and a reaction mixture without acetolactic acid, the activity value was calculated with use of molar absorbance coefficient of 6.22 $M^{-1}cm^{-1}$.

The results of AHAIR activity measurement of *Corynebacterium glutamicum* R ldhA mutant/pCRB1-ilvB-ilvN-ilvC/CG, which was constructed in Example 1 by introducing an AHAIR-encoding gene thereinto, and of *Corynebacterium glutamicum* R ldhA mutant used as a control are shown in the table below (1 U means the amount of enzyme which consumes 1 μmol of substrate per minute).

TABLE 2

| *Corynebacterium glutamicum* AHAIR recombinant strain activity measurement | | |
|---|---|---|
| Strain | | AHAIR activity |
| Plasmid | Introduced gene | (U/mg-protein) |
| pCRB1-ilvB-ilvN-ilvC/CG | ilvC (*Corynebacterium glutamicum* R) | 0.13 |
| *Corynebacterium glutamicum* R ldhA mutant | | 0.01 |

For measuring the DHAD activity, increase in absorbance at 340 nm associated with the increase in 2-ketoisovaleric acid during the formation of 2-ketoisovaleric acid from 2,3-dihydroxyisovaleric acid was used as an index (Dennis H. F., et. al., The role and properties of the iron-sulfur cluster in *Escherichia coli* dihydroxy-acid dehydratase. J. Biol. Chem., 268: 14732-14742 (1993)). The reaction mixture used for the activity measurement was composed of 50 mM tris-hydrochloric acid buffer solution at pH 8.0, 10 mM magnesium chloride, and 6 mM 2,3-dihydroxyisovaleric acid, and spectrophotometer DU-800 (made by BECKMAN) was used for the absorption spectrometry. To the reaction mixture, Enzyme Liquid 1 was added at 30° C. to start the reaction. From the difference of the slope of decrease in absorbance between the reaction mixture and a reaction mixture without 2,3-dihydroxyisovaleric acid, the activity value was calculated with use of molar absorbance coefficient of 190 $M^{-1}cm^{-1}$.

The results of DHAD activity measurement of *Corynebacterium glutamicum* R ldhA mutant/pCRB207-ilvD/CG, which was constructed in Example 1 by introducing an DHAD-encoding gene thereinto, and of *Corynebacterium glutamicum* R ldhA mutant used as a control are shown in the table below (1 U means the amount of enzyme which consumes 1 µmol of substrate per minute).

TABLE 3

*Corynebacterium glutamicum* DHAD recombinant strain activity measurement

| Strain | | DHAD activity |
|---|---|---|
| Plasmid | Introduced gene | (U/mg-protein) |
| pCRB207-ilvD/CG | ilvD (*Corynebacterium glutamicum* R) | 0.74 |
| *Corynebacterium glutamicum* R ldhA mutant | | 0.01 |

For measuring the ADH activity, decrease in absorbance at 340 nm associated with the decrease in NADH during the formation of isobutanol from isobutyraldehyde was used as an index (Durre, P. et al., Enzymatic investigations on butanol dehydrogenase and butyraldehyde dehydrogenase in extracts of *Clostridium acetobutylicum*. Appl. Microbiol. Biotechnol. 26: 268-272 (1987)). The reaction mixture was composed of 50 mM MES buffer solution (pH 6.0), 0.15 mM NADH, and 40 mM isobutyraldehyde. Spectrometry was performed with use of a spectrophotometer Ultrospec 2100 pro (made by GE Healthcare Bioscience) in an anaerobic chamber (made by COY) filled with 95% $N_2$ and 5% $H_2$. To the reaction mixture, Enzyme Liquid 2 was added at 30° C., and the mixture was left stand for 10 minutes. Then, isobutyraldehyde was added thereto to the concentration of 40 mM, or pure water was added thereto for a control sample. From the difference in absorbance decrease between the two, the activity value was calculated with use of molar absorbance coefficient of 6,220 $M^{-1}cm^{-1}$.

The results of ADH activity measurement of *Corynebacterium glutamicum* R ldhA mutant/pCRB207-adh2/SC, ldhA mutant/pCRB207-adhP/EC, and ldhA mutant/pCRB207-adh/PP, all of which were constructed in Example 1 by introducing an ADH-encoding gene thereinto, and of *Corynebacterium glutamicum* R ldhA mutant used as a control are shown in the table below (1 U means the amount of enzyme which consumes 1 µmol of substrate per minute).

TABLE 4

*Corynebacterium glutamicum* ADH recombinant strain activity measurement

| Strain | | ADH activity |
|---|---|---|
| Plasmid | Introduced gene | (U/mg-protein) |
| pCRB207-adh2/SC | adh2 (*Saccharomyces cerevisiae*) | 2.4 |
| pCRB207-adhP/EC | adhP (*Escherichia coli*) | 7.7 |
| pCRB207-adh/PP | adh (*Pseudomonas putida*) | 14.6 |
| *Corynebacterium glutamicum* R ldhA mutant | | ND |

ND: Not detectable (2) Activity Measurement of KDC

*Corynebacterium glutamicum* single-gene transgenic strain was applied to A agar medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O+0.042\%$ (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar suspended in 1 L of distilled water) containing 50 µg/mL of kanamycin, and left stand in the dark at 28° C. for 20 hours.

An inoculation loop of the *Corynebacterium glutamicum* single-gene transgenic strain grown on a plate as above was inoculated in a test tube containing 10 mL of A liquid medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O+0.042\%$ (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, and 40 g of glucose suspended in 1 L of distilled water) containing 50 µg/mL of kanamycin, and aerobically cultured with shaking at 28° C. for 15 hours.

The *Corynebacterium glutamicum* single-gene transgenic strain grown in the above conditions was inoculated in 100 mL of A liquid medium containing 50 µg/mL of kanamycin, and aerobically cultured with shaking at 28° C. for 15 hours. *Corynebacterium glutamicum* R ldhA mutant was cultured in the same conditions except that the A medium did not contain kanamycin.

The bacterial cells cultured and proliferated as above were collected by centrifugation (8,000×g at 4° C. for 10 minutes). The obtained bacterial cells were suspended in 40 mL of BT (-glucose) liquid medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O+0.042\%$ (w/v) $MnSO_4.2H_2O$, 1 mL of 0.02% (w/v) biotin solution, and 2 mL of 0.01% (w/v) thiamin solution dissolved in 1 L of distilled water), and moved into a 50-mL medium bottle. The following operations were performed in an anaerobic chamber (made by COY) filled with 95% $N_2$ and 5% $H_2$. The medium bottle was opened in the anaerobic chamber and stirring was continued for 2 hours so that anaerobic replacement in the culture medium and the bacterial cells was achieved. The bacterial cells were collected by centrifugation (5,000×g at 4° C. for 10 minutes) and then washed with Homogenate 2 (50 mM MOPS buffer solution at pH 7.0). Centrifugation was performed again, and the collected bacterial cells were suspended in 1 mL of Homogenate 2. To this, 2 g of glass beads were added and then 1-minute homogenization with a vortex mixer and 1-minute standing on ice were repeated 10 times to disrupt the bacterial cells. Then, centrifugation (5,000×g at 4° C. for 10 minutes) was performed to remove insoluble substances, and Enzyme Liquid 2 was thus obtained. With use of the obtained Enzyme Liquid 2, the activity of KDC was determined by the method shown below.

The KDC activity was determined with use of a 2-step reaction involving alcohol dehydrogenase from yeast (made by Roche). That is, in addition to the conversion from 2-ketoisovaleric acid to isobutyraldehyde, conversion from isobutyraldehyde to isobutanol by the alcohol dehydrogenase from yeast was performed. Since one molecule of NADH is consumed when isobutanol is formed from one molecule of 2-ketoisovaleric acid in this reaction, decrease in absorbance at 340 nm associated with the decrease in NADH was used as an index for measuring the KDC activity. The reaction mixture was composed of 50 mM MES buffer solution at pH 6.0, 0.5 mM magnesium chloride, 1.5 mM TPP, 0.2 mM 2-ketoisovaleric acid, 0.15 mM NADH, and 20 U of alcoholic dehydrogenase from yeast. Spectrometry was performed with use of a spectrophotometer Ultrospec 2100 pro (made by GE Healthcare Bioscience) in an anaerobic chamber (made by COY) filled with 95% $N_2$ and 5% $H_2$. To the reaction mixture, Enzyme Liquid 2 was added at 30° C., and the mixture was left stand for 10 minutes. Then, 6 mM of 2-ketoisovaleric acid, or pure water for a control sample, was added thereto. From the difference in absorbance decrease between the two, the activity value was calculated with use of molar absorbance coefficient of 6,220 $M^{-1}cm^{-1}$.

The results of KDC activity measurement of *Corynebacterium glutamicum* R ldhA mutant/pCRB207-kivD/LL and ldhA mutant/pCRB207-ipd/SE, both of which were constructed in Example 1 by introducing a KDC-encoding gene thereinto, and of *Corynebacterium glutamicum* R ldhA mutant used as a control are shown in the table below (1 U means the amount of enzyme which consumes 1 µmol of substrate per minute).

TABLE 5

*Corynebacterium glutamicum* KDC recombinant strain activity measurement

| Strain | | KDC activity |
|---|---|---|
| Plasmid | Introduced gene | (U/mg-protein) |
| pCRB207-kivD/LL | kivD (*Lactococcus lactis*) | 0.12 |
| pCRB207-ipd/SE | ipd (*Staphylococcus epidermidis*) | 0.05 |
| *Corynebacterium glutamicum* R ldhA mutant | | 0 |

Example 3

Creation of Corynebacterium glutamicum IBU1, IBU2, IBU3, IBU4, and IBU5

(1) Cloning of Butanol-Producing Genes Cloning of Isobutanol-Producing Gene Derived from Bacillus subtilis A DNA fragment comprising the alsS gene which encodes acetohydroxy acid synthase derived from *Bacillus subtilis* was amplified by the PCR method as described below.

In the PCR, the following set of primers was synthesized based on the sequence from *Bacillus subtilis* (SEQ ID NO: 58 (the alsS gene)) with use of "394 DNA/RNA Synthesizer" made by Applied Biosystems for cloning of the alsS gene, and was used.

Primers for alsS Gene Amplification

```
                                        (SEQ ID NO: 59)
(a-20):   5'-CTCT CCCGGG
          AAACTTTTTAGAAAGGTGTGTTTCACCCGTGTTGACAAAA
          GCAACAAAAGAAC-3'

(SEQ ID NO: 60)
(b-20):   5'-CTCT CCCGGG AGATCT CTAGAGAGCTTTCGTTTT
          CATGA-3'
```

Primer (a-20) has a SmaI restriction enzyme site added thereto, and primer (b-20) has SmaI and BglII restriction enzyme sites added thereto.

Cloning of Isobutanol-Producing Genes Derived from Corynebacterium glutamicum

A DNA fragment comprising the ilvB-ilvN gene which encodes acetohydroxy acid synthase, a DNA fragment comprising the ilvC gene which encodes acetohydroxy acid isomeroreductase, and a DNA fragment comprising the ilvD gene which encodes dihydroxy acid dehydratase, derived from *Corynebacterium glutamicum*, were amplified by the PCR method as described below.

In the PCR, the following sets of primers were synthesized based on the sequence from *Corynebacterium glutamicum* (SEQ ID NO: 34 (the ilvB-ilvN-ilvC gene)), (SEQ ID NO: 61 (the ilvC gene)), and (SEQ ID NO: 62 (the ilvD gene)) with use of "394 DNA/RNA Synthesizer" made by Applied Biosystems for cloning of the ilvB-ilvN-ilvC gene, the ilvC gene, and the ilvD gene, and were used.

Primers for ilvB-ilvN-ilvC Gene Amplification

```
                                        (SEQ ID NO: 36)
(a-12):   5'-GA CCCGGG AGTAAAGGAGCCAGAAAGTCGTGAA-3'

(SEQ ID NO: 37)
(b-12):   5'-GA CCCGGG CCTGCAGG TGCCTTATGTACAAAGTGC
          ACAGCA-3'
```

Primer (a-12) has a SmaI restriction enzyme site added thereto, and primer (b-12) has SmaI and Sse8387I restriction enzyme sites added thereto.

Primers for ilvC Gene Amplification

```
                                        (SEQ ID NO: 63)
(a-21):   5'-CTCT CCATGG CTATTGAACTGCTTTATGATG-3'

(SEQ ID NO: 64)
(b-21):   5'-CTCT CCATGG AGATCT TTAAGCGGTTTCTGCGC
          GA-3'
```

Primer (a-21) has an NcoI restriction enzyme site added thereto, and primer (b-21) has NcoI and BglII restriction enzyme sites added thereto.

Primers for ilvD Gene Amplification

```
                                        (SEQ ID NO: 65)
(a-22):   5'-GA CCCGGG GAGCAGATTTGAAAAGCGCATCATG-3'

(SEQ ID NO: 66)
(b-22):   5'-GA CCCGGG GGTACC GTATTTGCAACGGGGAGCTCC
          ACCA-3'
```

Primer (a-22) has a SmaI restriction enzyme site added thereto, and primer (b-22) has SmaI and KpnI restriction enzyme sites added thereto.

Cloning of Isobutanol-Producing Genes Derived from *Escherichia coli*

A DNA fragment comprising the ilvB-ilvN gene which encodes acetohydroxy acid synthase, a DNA fragment comprising the ilvC gene which encodes acetohydroxy acid isomeroreductase, a DNA fragment comprising the ilvD gene which encodes dihydroxy acid dehydratase, and a DNA fragment comprising the adhP gene which encodes alcohol dehydrogenase, derived from *Escherichia coli*, were amplified by the PCR method as described below.

In the PCR, the following sets of primers were synthesized based on the sequence from *Escherichia coli* (SEQ ID NO: 67 (the ilvB-ilvN gene)), (SEQ ID NO: 68 (the ilvC gene)), (SEQ ID NO: 69 (the ilvD gene)), and (SEQ ID NO: 40 (the adhP gene)) with use of "394 DNA/RNA Synthesizer" made by Applied Biosystems for cloning of the ilvB-ilvN gene, the ilvC gene, the ilvD gene, and the adhP gene, and were used.

Primers for ilvB-ilvN Gene Amplification

```
                                        (SEQ ID NO: 70)
(a-23):   5'-CTCT CCCGGG ATGGCAAGTTCGGGCACAA-3'

(SEQ ID NO: 71)
(b-23):   5'-CTCT CCCGGG AGATCT TTACTGAAAAAACACC
          GCGATCTT-3'
```

Primer (a-23) has a SmaI restriction enzyme site added thereto, and primer (b-23) has SmaI and BglII restriction enzyme sites added thereto.

Primers for ilvC Gene Amplification (SEQ ID NO: 72)
(a-24):  5'-CTCT CCCGGG ATGGCTAACTACTTCAATACACTG-3'

(SEQ ID NO: 73)
(b-24):  5'-CTCT CCCGGG AGATCT TTAACCCGCAACAGCAATACG-3'

Primer (a-24) has a SmaI restriction enzyme site added thereto, and primer (b-24) has SmaI and BglII restriction enzyme sites added thereto.

Primers for ilvD Gene Amplification (SEQ ID NO: 74)
(a-25):  5'-CTCT TTTAAA ATGCCTAAGTACCGTTCCG-3'

(SEQ ID NO: 75)
(b-25):  5'-CTCT TTTAAA AGATCT TTAACCCCCCAGTTTCGATTTAT-3'

Primer (a-25) has a DraI restriction enzyme site added thereto, and primer (b-25) has DraI and BglII restriction enzyme sites added thereto.

Primers for adhP Gene Amplification (SEQ ID NO: 41)
(a-14):  5'-CTCT CCATGG AGGCTGCAGTTGTTACGAAG-3'

(SEQ ID NO: 42)
(b-14):  5'-CTCT CCATGG AGATCT TTAGTGACGGAAATCAATCACCAT-3'

Primer (a-14) has an NcoI restriction enzyme site added thereto, and primer (b-14) has NcoI and BglII restriction enzyme sites added thereto.

Cloning of a Group of Butanol-Producing Genes Derived from *Lactococcus lactis*

A DNA fragment comprising the kivD gene which encodes 2-keto acid decarboxylase derived from *Lactococcus lactis* was amplified by the PCR method as described below.

In the PCR, the following set of primers was synthesized based on the sequence from *Lactococcus lactis* (SEQ ID NO: 43 (the kivD gene)) with use of "394 DNA/RNA Synthesizer" made by Applied Biosystems for cloning of the kivD gene, and was used.

Primers for kivD Gene Amplification (SEQ ID NO: 44)
(a-15):  5'-CTCT CCATGG ATACAGTAGGAGATTACCTATTAGAC-3'

(SEQ ID NO: 45)
(b-15):  5'-CTCT CCATGG AGATCT TTATGATTTATTTTGTTCAGCAAATAGTTTGCC-3'

Primer (a-15) has an NcoI restriction enzyme site added thereto, and primer (b-15) has NcoI and BglII restriction enzyme sites added thereto.

Cloning of Isobutanol-Producing Gene Derived from *Pseudomonas Putida*

A DNA fragment comprising the adh gene which encodes alcohol dehydrogenase derived from *Pseudomonas putida* was amplified by the PCR method as described below.

In the PCR, the following set of primers was synthesized based on the sequence from *Pseudomonas putida* (SEQ ID NO: 46 (the adh gene)) with use of "394 DNA/RNA Synthesizer" made by Applied Biosystems for cloning of the adh gene, and was used.

Primers for adh Gene Amplification (SEQ ID NO: 47)
(a-16):  5'-CTCT TCATGA AAGCTGCTGTCGTTGC-3'

(SEQ ID NO: 48)
(b-16):  5'-CTCT TCATGA CTCGAG TCAGCCTTCGAACTGTATCAC-3'

Primer (a-16) has a BspHI restriction enzyme site added thereto, and primer (b-16) has BspHI and XhoI restriction enzyme sites added thereto.

Cloning of Isobutanol-Producing Gene Derived from *Saccharomyces cerevisiae*

A DNA fragment comprising the adh2 gene which encodes alcohol dehydrogenase derived from *Saccharomyces cerevisiae* was amplified by the PCR method as described below.

In the PCR, the following set of primers was synthesized based on the sequence from *Saccharomyces cerevisiae* (SEQ ID NO: 49 (the adh2 gene)) with use of "394 DNA/RNA Synthesizer" made by Applied Biosystems for cloning of the adh2 gene, and was used.

Primers for adh2 Gene Amplification (SEQ ID NO: 50)
(a-17):  5'-CTCT CCATGG CTATTCCAGAAACTCAAAAAGCCATTAT-3'

(SEQ ID NO: 51)
(b-17):  5'-CTCT CCATGG AGATCT TTATTTAGAAGTGTCAACAACGTATCTAC-3

Primer (a-17) has an NcoI restriction enzyme site added thereto, and primer (b-17) has NcoI and BglII restriction enzyme sites added thereto.

The template DNAs used are as follows. For *Bacillus subtilis*, the chromosomal DNA extracted from *Bacillus subtilis* 168 NBRC14144 obtained from NITE Biological Resource Center (NBRC) was used. For *Corynebacterium glutamicum*, the chromosomal DNA extracted from *Corynebacterium glutamicum* R was used. For *Escherichia coli*, the chromosomal DNA extracted from *Escherichia coli* K12 MG1655 was used. For *Lactococcus lactis*, the chromosomal DNA extracted from *Lactococcus lactis* NBRC100933 obtained from NITE Biological Resource Center (NBRC) was used. For *Pseudomonas putida*, the chromosomal DNA extracted from *Pseudomonas putida* F1 ATCC700007 obtained from American Type Culture Collection (ATCC) was used. For *Saccharomyces cerevisiae*, the chromosomal DNA extracted from *Saccharomyces cerevisiae* NBRC 2376 obtained from NITE Biological Resource Center (NBRC) was used.

Actual PCR was performed with use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |

-continued

| | |
|---|---|
| The above 2 primers*⁾ | 0.5 µL each (final conc.: 1 µM) |
| Sterile distilled water: | 25.5 µL |

The above ingredients were mixed, and 50 µL of the reaction mixture was subjected to PCR.

*⁾For amplification of the alsS gene of *Bacillus subtilis*, a combination of primers (a-20) and (b-20); for amplification of the ilvB-ilvN-ilvC gene of *Corynebacterium glutamicum*, a combination of primers (a-12) and (b-12); for amplification of the ilvC gene of *Corynebacterium glutamicum*, a combination of primers (a-21) and (b-21); for amplification of the ilvD gene of *Corynebacterium glutamicum*, a combination of primers (a-22) and (b-22); for amplification of the ilvB-ilvN gene of *Escherichia coli*, a combination of primers (a-23) and (b-23); for amplification of the ilvC gene of *Escherichia coli*, a combination of primers (a-24) and (b-24); for amplification of the ilvD gene of *Escherichia coli*, a combination of primers (a-25) and (b-25); for amplification of the adhP gene of *Escherichia coli*, a combination of primers (a-14) and (b-14); for amplification of the kivD gene of *Lactococcus lactis*, a combination of primers (a-15) and (b-15); for amplification of the adh gene of *Pseudomonas putida*, a combination of primers (a-16) and (b-16); and for amplification of the adh2 gene of *Saccharomyces cerevisiae*, a combination of primers (a-17) and (b-17) was used.

PCR Cycle:
Denaturation step: 94° C., 60 seconds
Annealing step: 52° C., 60 seconds
Extension step: 72° C.
  *Bacillus subtilis* alsS gene: 120 seconds
  *Corynebacterium glutamicum* ilvB-ilvN-ilvC gene: 240 seconds
  *Corynebacterium glutamicum* ilvC gene: 60 seconds
  *Corynebacterium glutamicum* ilvD gene: 120 seconds
  *Escherichia coli* ilvB-ilvN gene: 120 seconds
  *Escherichia coli* ilvC gene: 90 seconds
  *Escherichia coli* ilvD gene: 120 seconds
  *Escherichia coli* adhP gene: 60 seconds
  *Lactococcus lactis* kivD gene 120 seconds
  *Pseudomonas putida* adh gene: 60 seconds
  *Saccharomyces cerevisiae* adh2 gene: 70 seconds A cycle consisting of the above 3 steps was repeated 30 times.

Using 10 µL of each of the above produced reaction mixtures, 0.8% agarose gel electrophoresis was performed. Detected were, about a 1.8-kb DNA fragment in the case of the alsS gene of *Bacillus subtilis*, about a 3.7-kb DNA fragment in the case of the ilvB-ilvN-ilvC gene of *Corynebacterium glutamicum*, about a 1.0-kb DNA fragment in the case of the ilvC gene of *Corynebacterium glutamicum*, about a 2.0-kb DNA fragment in the case of the ilvD gene of *Corynebacterium glutamicum*, about a 2.0-kb DNA fragment in the case of the ilvB-ilvN gene of *Escherichia coli*, about a 1.5-kb DNA fragment in the case of the ilvC gene of *Escherichia coli*, about a 1.9-kb DNA fragment in the case of the ilvD gene of *Escherichia coli*, about a 1.0-kb DNA fragment in the case of the adhP gene of *Escherichia coli*, about a 1.7-kb DNA fragment in the case of the kivD gene of *Lactococcus lactis*, about a 1.0-kb DNA fragment in the case of the adh gene of *Pseudomonas putida*, and about a 1.1-kb DNA fragment in the case of the adh2 gene of *Saccharomyces cerevisiae*.

(2) Construction of Isobutanol-Production Gene Expression Plasmids

Cloning of Isobutanol-Production Gene to pKK223-3

10 µL of the about 3.7-kb DNA fragment comprising the ilvB-ilvN-ilvC gene derived from *Corynebacterium glutamicum*, the about 2.0-kb DNA fragment comprising the ilvD gene derived from *Corynebacterium glutamicum*, the about 2.0-kb DNA fragment comprising the ilvB-ilvN gene derived from *Escherichia coli*, and the about 1.5-kb DNA fragment comprising the ilvC gene derived from *Escherichia coli*, all of which amplified by the PCR in the above (1), and 2 µL of the cloning vector pKK233-3 (made by Pharmacia) comprising a tac promoter were each cut with use of a restriction enzyme SmaI and processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation. Thus obtained were named Ligation Liquids Q, R, S, and T.

Similarly, 10 µL of the about 1.9-kb DNA fragment comprising the ilvD gene derived from *Escherichia coli* amplified by the above PCR was cut with use of a restriction enzyme DraI and 2 µL of the cloning vector pKK233-3 (made by Pharmacia) comprising a tac promoter was cut with use of a restriction enzyme SmaI, and both were processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation. This was named Ligation Liquid U.

With use of each of the obtained five kinds of Ligation Liquids Q, R, S, T, and U, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 µg/mL of ampicillin.

A growing strain on the culture medium was subjected to liquid culture in the usual manner. Plasmid DNA was extracted from the culture medium and cut with use of restriction enzymes to confirm the inserted fragments. As a result, in addition to an about 4.6-kb DNA fragment of the plasmid pKK223-3, confirmed was an about 3.7-kb inserted fragment comprising the ilvB-ilvN-ilvC gene derived from *Corynebacterium glutamicum* (Ligation Liquid Q), an about 2.0-kb inserted fragment comprising the ilvD gene derived from *Corynebacterium glutamicum* (Ligation Liquid R), an about 2.0-kb inserted fragment comprising the ilvB-ilvN gene derived from *Escherichia coli* (Ligation Liquid S), an about 1.5-kb inserted fragment comprising the ilvC gene derived from *Escherichia coli* (Ligation Liquid T), or an about 1.9-kb inserted fragment comprising the ilvD gene derived from *Escherichia coli* (Ligation Liquid U).

The plasmid comprising the ilvB-ilvN-ilvC gene derived from *Corynebacterium glutamicum* was named pKK223-3-ilvB-ilvN-ilvC/CG, the plasmid comprising the ilvD gene derived from *Corynebacterium glutamicum* was named pKK223-3-ilvD/CG, the plasmid comprising the ilvB-ilvN gene derived from *Escherichia coli* was named pKK223-3-ilvB-ilvN/EC, the plasmid comprising the ilvC gene derived from *Escherichia coli* was named pKK223-3-ilvC/EC, and the plasmid comprising the ilvD gene derived from *Escherichia coli* was named pKK223-3-ilvD/EC.

Cloning of Isobutanol-Production Genes to pCRB1

From the above plasmids pKK223-3-ilvB-ilvN-ilvC/CG and pKK223-3-ilvD/CG, a DNA fragment comprising the tac promoter and the ilvB-ilvN-ilvC gene derived from *Corynebacterium glutamicum* R, and a DNA fragment comprising the tac promoter and the ilvD gene derived from *Corynebacterium glutamicum* R were amplified by the PCR method as described below.

In the PCR, the following sets of primers were synthesized based on the tac promoter and the ilvB-ilvN-ilvC gene (SEQ ID NO: 55 (Ptac-ilvB-ilvN-ilvC sequence)), and the ilvD gene (SEQ ID NO: 76 (Ptac-ilvD sequence)) derived from *Corynebacterium glutamicum* R, and were used.

Primers for Ptac-ilvB-ilvN-ilvC Sequence Amplification

```
                                      (SEQ ID NO: 56)
(a-19):   5' '-AT GCAAGC TTCGGCTGTGCAGGTCGTAAAT-3'

(SEQ ID NO: 57)
(b-19):   5'-AC GCAAGC TTCGCTTATGTACAAAGTGCAC-3'
```

Primers (a-19) and (b-19) each have a HindIII restriction enzyme site added thereto.

Primers for Ptac-ilvD Sequence Amplification

```
                                      (SEQ ID NO: 77)
(a-26):   5'-ATAT CCTGCAGG CTAGCGCTGTGCAGGTCGTAAAT
          CAACT-3'

(SEQ ID NO: 78)
(b-26);   5'-ATATGCTAGCT CCTGCAGG TATTTGCAACGGGGAG
          CTC-3'
```

Primers (a-26) and (b-26) each have a Sse8387I restriction enzyme site added thereto.

As the template DNA, the above-mentioned plasmid pKK223-3-ilvB-ilvN-ilvC/CG and pKK223-3-ilvD/CG were used.

Actual PCR was performed with use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/µL) | 0.5 µL |
| 10× LA PCR ™ Buffer II (Mg$^{2+}$ free) | 5 µL |
| 25 mM MgCl$_2$ | 5 µL |
| dNTP Mixture (2.5 mM each) | 8 µL |
| Template DNA | 5 µL (DNA content: 1 µg or less) |
| The above 2 primers*$^)$ | 0.5 µL each (final conc.: 1 µM) |
| Sterile distilled water: | 25.5 µL |
| The above ingredients were mixed, and 50 µL of the reaction mixture was subjected to PCR. | |

*$^)$For amplification of the Ptac-ilvB-ilvN-ilvC sequence, a combination of primers (a-19) and (b-19), and for amplification of the Ptac-ilvD sequence, a combination of primers (a-26) and (b-26) was used.

PCR Cycle:
Denaturation step: 94° C., 60 seconds
Annealing step: 52° C., 60 seconds
Extension step: 72° C.
Ptac-ilvB-ilvN-ilvC sequence: 240 seconds
Ptac-ilvD sequence: 150 seconds A cycle consisting of the above 3 steps was repeated 30 times.

Using 10 µL of the above-produced reaction mixture, 0.8% agarose gel electrophoresis was performed. In the case of the Ptac-ilvB-ilvN-ilvC sequence, an about 3.9-kb fragment was detected. In the case of the Ptac-ilvD sequence, an about 2.2-kbp DNA fragment was detected.

10 µl, of the about 3.9-kb DNA fragment comprising the tac promoter sequence and the ilvB-ilvN-ilvC sequence derived from *Corynebacterium glutamicum* R amplified by the above PCR, and 2 µL of about 4.1-kb cloning vector pCRB1 (Nakata, K. et al., Vectors for the genetics engineering of *corynebacteria*; in Saha, B. C. (ed.): Fermentation Biotechnology, ACS Symposium Series 862. Washington, American Chemical Society: 175-191 (2003)) were each cut with use of a restriction enzyme HindIII and processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µl, and the mixture was allowed to react at 15° C. for 3 hours for ligation. This was named Ligation Liquid V.

With use of the Ligation Liquid V, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 µg/mL of chloramphenicol.

A growing strain on the culture medium was subjected to liquid culture in the usual manner. Plasmid DNA was extracted from the culture medium and cut with use of a restriction enzyme HindIII to confirm the inserted fragment. As a result, in addition to an about 4.1-kb DNA fragment of the plasmid pCRB1, an about 3.9-kb inserted fragment was confirmed in the case of the ilvB-ilvN-ilvC gene derived from *Corynebacterium glutamicum* (Ligation Liquid V).

The plasmid comprising the ilvB-ilvN-ilvC gene derived from *Corynebacterium glutamicum* was named pCRB1-ilvB-ilvN-ilvC/CG.

10 µL of the about 2.2-kb DNA fragment comprising the tac promoter sequence and the ilvD sequence derived from *Corynebacterium glutamicum* R amplified by the above PCR, and 2 µL of the about 8.0-kb pCRB1-ilvB-ilvN-ilvC/CG were each cut with use of a restriction enzyme Sse8387I and processed at 70° C. for 10 minutes for deactivation of the restriction enzyme. Both were mixed, and 1 µl of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation. This was named Ligation Liquid W.

With use of the Ligation Liquid W, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 µg/mL of chloramphenicol.

A growing strain on the culture medium was subjected to liquid culture in the usual manner. Plasmid DNA was extracted from the culture medium and cut with use of a restriction enzyme Sse8387I to confirm the inserted fragment. As a result, in addition to an about 8.0-kb DNA fragment of the plasmid pCRB1-ilvB-ilvN-ilvC/CG, an about 2.2-kb inserted fragment was confirmed in the case of the ilvD gene derived from *Corynebacterium glutamicum* (Ligation Liquid W).

Figure 2:
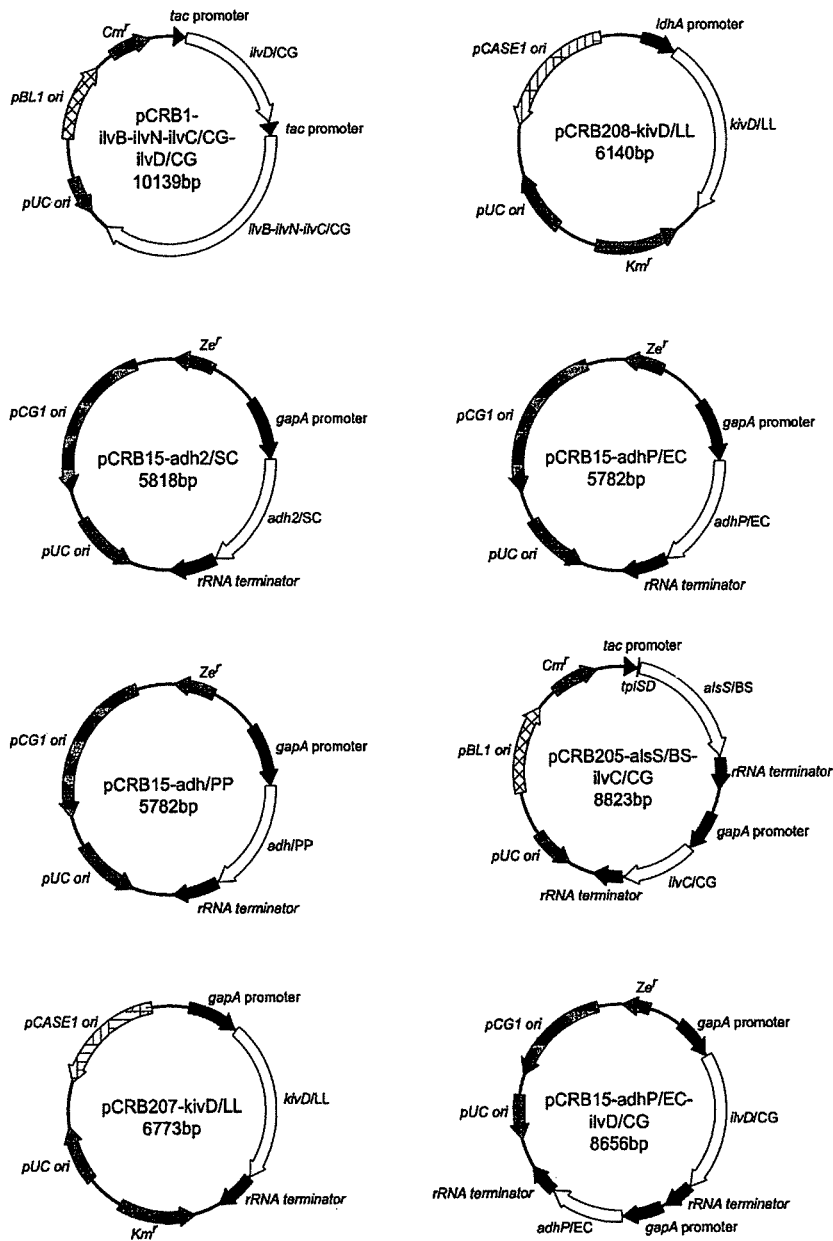
FIG. 2 is a schematic view showing pCRB1-ilvB-ilvN-ilvC/CG-ilvD/CG, pCRB208-kivD/LL, pCRB15-adh2/SC, pCRB15-adhP/EC, pCRB15-adh/PP, pCRB205-alsS/BS-ilvC/CG, pCRB207-kivD/LL, and pCRB15-adhP/EC-ilvD/CG, prepared in Example 3 (2).

The plasmid comprising the ilvB-ilvN-ilvC gene and the ilvD gene derived from *Corynebacterium glutamicum* was named pCRB1-ilvB-ilvN-ilvC/CG-ilvD/CG (FIG. 2).

The above-mentioned plasmid pKK223-3-ilvB-ilvN/EC was cut with use of restriction enzymes BamHI and BglII. After agarose gel electrophoresis, an about 2.3-kb DNA fragment collected from the agarose gel with use of QIAquick Gel Extraction Kit (made by QIAGEN), in which fragment a tac promoter and the ilvB-ilvN gene derived from *Escherichia coli* were ligated, was mixed with the cloning vector pCRB1 cut with use of BamHI. To this, 1 µL of T4 DNA ligase 10× buffer solution and 1 unit of T4 DNA ligase (made by Takara Bio, Inc.) were added. Sterile distilled water was added thereto so that the total amount was 10 µL, and the mixture was allowed to react at 15° C. for 3 hours for ligation. This was named Ligation Liquid X.

With use of the Ligation Liquid X, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 µg/mL of chloramphenicol.

A growing strain on the culture medium was subjected to liquid culture in the usual manner. Plasmid DNA was extracted from the culture medium and cut with use of a restriction enzyme to confirm the inserted fragment. As a result, in addition to an about 4.1-kb DNA fragment of the plasmid pCRB1, an about 2.3-kb inserted fragment was confirmed in the case of the ilvB-ilvN gene derived from *Escherichia coli* (Ligation Liquid X).

The plasmid comprising the ilvB-ilvN gene derived from *Escherichia coli* was named pCRB1-ilvB-ilvN/EC.

This plasmid has only 1 site of restriction enzyme BamHI.

The above-mentioned plasmid pKK223-3-ilvC/EC was cut with use of restriction enzymes BamHI and BglII. After agarose gel electrophoresis, an about 1.7-kb DNA fragment collected from the agarose gel with use of QIAquick Gel Extraction Kit (made by QIAGEN), in which fragment a tac promoter and the ilvC gene derived from *Escherichia coli* were ligated, was mixed with the above-mentioned plasmid pCRB1-ilvB-ilvN/EC cut with use of BamHI. To this, 1 µL of T4 DNA ligase 10× buffer solution and 1 unit of T4 DNA ligase (made by Takara Bio, Inc.) were added. Sterile distilled water was added thereto so that the total amount was 10 µL, and the mixture was allowed to react at 15° C. for 3 hours for ligation. This was named. Ligation Liquid Y.

With use of the Ligation Liquid Y, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 µg/mL of chloramphenicol.

A growing strain on the culture medium was subjected to liquid culture in the usual manner. Plasmid DNA was extracted from the culture medium and cut with use of a restriction enzyme to confirm the inserted fragment. As a result, in addition to an about 6.4-kb DNA fragment of the plasmid pCRB1-ilvB-ilvN/EC, an about 1.7-kb inserted fragment was confirmed in the case of the ilvC gene derived from *Escherichia coli* (Ligation Liquid Y).

The plasmid comprising the ilvB-ilvN gene derived from *Escherichia coli* and the ilvC gene derived from *Escherichia coli* was named pCRB1-ilvB-ilvN/EC-ilvC/EC.

This plasmid has only 1 site of restriction enzyme BamHI.

The above-mentioned plasmid pKK223-3-ilvD/EC was cut with use of restriction enzymes BamHI and BglII. After agarose gel electrophoresis, an about 2.1-kb DNA fragment collected from the agarose gel with use of QIAquick Gel Extraction Kit (made by QIAGEN), in which fragment a tac promoter and the ilvD gene derived from *Escherichia coli* were ligated, was mixed with the above-mentioned plasmid pCRB1-ilvB-ilvN/EC-ilvC/EC cut with use of BamHI. To this, 1 µl of T4 DNA ligase 10× buffer solution and 1 unit of T4 DNA ligase (made by Takara Bio, Inc.) were added. Sterile distilled water was added thereto so that the total amount was 10 µl, and the mixture was allowed to react at 15° C. for 3 hours for ligation. This was named Ligation Liquid Z.

With use of the Ligation Liquid Z, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 µg/mL of chloramphenicol.

A growing strain on the culture medium was subjected to liquid culture in the usual manner. Plasmid DNA was extracted from the culture medium and cut with use of a restriction enzyme to confirm the inserted fragment. As a result, in addition to an about 8.1-kb DNA fragment of the plasmid pCRB1-ilvB-ilvN/EC-ilvC/EC, confirmed was about 2.1-kb inserted fragment comprising the ilvD gene derived from *Escherichia coli* (Ligation Liquid Z).

The plasmid comprising the ilvB-ilvN gene derived from *Escherichia coli*, the ilvC gene derived from *Escherichia coli*, and the ilvD gene derived from *Escherichia coli* was named pCRB1-ilvB-ilvN/EC-ilvC/EC-ilvD/EC.

This plasmid has only 1 site of restriction enzyme BamHI.

Cloning of Isobutanol-Production Gene to pCRB207

10 µL of the about 1.0-kb DNA fragment comprising the ilvC gene derived from *Corynebacterium glutamicum*, the about 1.0-kb DNA fragment comprising the adhP gene derived from *Escherichia coli*, the about 1.7-kb DNA fragment comprising the kivD gene derived from *Lactococcus lactis*, or the about 1.1-kb DNA fragment comprising the adh2 gene derived from *Saccharomyces cerevisiae*, amplified by the PCR in the above (1) and 2 µL of the cloning vector pCRB207 comprising a PgapA promoter were each cut with use of a restriction enzyme NcoI and processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation. Thus obtained were named Ligation Liquids AA, AB, AC, and AD.

Similarly, 10 µL of the about 2.0-kb DNA fragment comprising the ilvD gene derived from *Corynebacterium glutamicum* or the about 1.0-kb DNA fragment comprising the adh gene derived from *Pseudomonas putida* amplified by the PCR in the above (1) was each cut with use of BspHI and 2 µL of the cloning vector pCRB207 comprising a PgapA promoter was cut with use of a restriction enzyme NcoI. After deactivation of the restriction enzyme at 70° C. for 10 minutes, both were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation. Thus obtained were named Ligation Liquids AE and AF.

With use of each of the obtained six kinds of Ligation Liquids AA, AB, AC, AD, AE, and AF, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 µg/mL of kanamycin.

A growing strain on the culture medium was subjected to liquid culture in the usual manner. Plasmid DNA was extracted from the culture medium and cut with use of restriction enzymes to confirm the inserted fragments. As a result, in addition to an about 5.1-kb DNA fragment of the plasmid pCRB207, confirmed was an about 1.0-kb DNA fragment comprising the ilvC gene derived from *Corynebacterium glutamicum* (Ligation Liquid AA), an about 1.0-kb inserted fragment comprising the adhP gene derived from *Escherichia coli* (Ligation Liquid AB), an about 1.7-kb inserted fragment comprising the kivD gene derived from *Lactococcus lactis* (Ligation Liquid AC), an about 1.1-kb inserted fragment comprising the adh2 gene derived from *Saccharomyces cerevisiae* (Ligation Liquid AD), an about 2.0-kb inserted fragment comprising the ilvD gene derived from *Corynebacterium glutamicum* (Ligation Liquid AE), or an about 1.0-kb inserted fragment comprising the adh gene derived from *Pseudomonas putida* (Ligation Liquid AF).

The plasmid comprising the ilvC gene derived from *Corynebacterium glutamicum* was named pCRB207-ilvC/CG, the plasmid comprising the adhP gene derived from *Escherichia coli* was named pCRB207-adhP/EC, the plasmid comprising the kivD gene derived from *Lactococcus lactis* was named pCRB207-kivD/LL, the plasmid comprising the adh2 gene derived from *Saccharomyces cerevisiae* was named pCRB207-adh2/SC, the plasmid comprising the ilvD gene derived from *Corynebacterium glutamicum* was named pCRB207-ilvD/CG, and the plasmid comprising the adh gene derived from *Pseudomonas putida* was named pCRB207-adh/PP.

Cloning of Isobutanol-Production Genes to pCRB205

10 μL of the about 1.8-kb DNA fragment comprising the alsS gene derived from *Bacillus subtilis* amplified by the PCR in the above (1) and 2 μl of the cloning vector pCRB205 comprising a tac promoter were each cut with use of a restriction enzyme SmaI and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation. This was named Ligation Liquid AG.

With use of the Ligation Liquid AG, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 μg/mL of chloramphenicol.

A growing strain on the culture medium was subjected to liquid culture in the usual manner. Plasmid DNA was extracted from the culture medium and cut with use of a restriction enzyme SmaI to confirm the inserted fragment. As a result, in addition to an about 5.0-kb DNA fragment of the plasmid pCRB205, an about 1.8-kb inserted fragment was confirmed in the case of the alsS gene derived from *Bacillus subtilis* (Ligation Liquid AG).

The plasmid comprising the alsS gene derived from *Bacillus subtilis* was named pCRB205-alsS/BS.

The above-mentioned plasmid pCRB207-ilvC/CG was cut with use of a restriction enzyme BamHI. After agarose gel electrophoresis, an about 2.0-kb DNA fragment collected from the agarose gel with use of QIAquick Gel Extraction Kit (made by QIAGEN), in which fragment a gapA promoter, the ilvC gene derived from *Corynebacterium glutamicum*, and a terminator sequence were ligated, and the above-mentioned plasmid pCRB205-alsS/BS cut with use of SghI were blunted with use of DNA Blunting Kit (made by Takara Bio, Inc.). The DNA fragments were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μl, and the mixture was allowed to react at 15° C. for 3 hours for ligation. This was named Ligation Liquid AH.

With use of the Ligation Liquid AH, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 μg/mL of chloramphenicol.

A growing strain on the culture medium was subjected to liquid culture in the usual manner. Plasmid DNA was extracted from the culture medium and cut with use of a restriction enzyme to confirm the inserted fragment. As a result, in addition to an about 6.8-kb DNA fragment of the plasmid pCRB205-alasS/BS, an about 2.0-kb inserted fragment was confirmed in the case of the ilvC gene derived from *Corynebacterium glutamicum* (Ligation Liquid AH).

The plasmid comprising the alsS gene derived from *Bacillus subtilis* and the ilvC gene derived from *Corynebacterium glutamicum* was named pCRB205-alsS/BS-ilvC/CG (FIG. 2).

Cloning of Isobutanol-Production Gene to pCRB208

10 μL of the about 1.7-kb DNA fragment comprising the kivD gene derived from *Lactococcus lactis* amplified by the PCR in the above (1) and 2 μL of the cloning vector pCRB208 comprising a ldhA promoter were each cut with use of a restriction enzyme NcoI and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation. This was named Ligation Liquid AI.

use of the Ligation Liquid AI, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 50 μg/mL of kanamycin.

A growing strain on the culture medium was subjected to liquid culture in the usual manner. Plasmid DNA was extracted from the culture medium and cut with use of a restriction enzyme NcoI to confirm inserted fragment. As a result, in addition to an about 4.5-kb DNA fragment of the plasmid pCRB208, an about 1.7-kb inserted fragment was confirmed in the case of the kivD gene derived from *Lactococcus lactis* (Ligation Liquid AI).

The plasmid comprising the kivD gene derived from *Lactococcus lactis* was named pCRB208-kivD/LL (FIG. 2).

Cloning of Isobutanol-Production Gene to pCRB15

The above-mentioned plasmids pCRB207-adhP/EC, pCRB207-adh/PP, and pCRB207-adh2/SC were each cut with use of a restriction enzyme BamHI. After agarose gel electrophoresis, an about 2.0-kb DNA fragment, in which fragment a gapA promoter, the adhP gene derived from *Escherichia coli*, and a terminator sequence were ligated; an about 2.0-kb DNA fragment, in which fragment a gapA promoter, the adh gene derived from *Pseudomonas putida*, and a terminator sequence were ligated; and an about 2.1-kb DNA fragment, in which fragment a gapA promoter, the adh2 gene derived from *Saccharomyces cerevisiae*, and a terminator sequence were ligated, all collected from the agarose gel with use of QIAquick Gel Extraction Kit (made by QIAGEN), and the above-mentioned about 3.8-kb plasmid pCRB15 cut with use of a restriction enzyme BamHI, were each processed at 70° C. for 10 minutes for deactivation of the restriction enzyme. The DNA fragments were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation. These were named Ligation Liquids AJ, AK, and AL.

With use of each of the obtained three kinds of Ligation Liquids AJ, AK, and AL, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 25 μg/mL of zeocin.

A growing strain on the culture medium was subjected to liquid culture in the usual manner. Plasmid DNA was extracted from the culture medium and cut with use of a restriction enzyme BamHI to confirm the inserted fragments. As a result, in addition to an about 3.8-kb DNA fragment of the plasmid pCRB15, confirmed was an about 2.0-kb inserted fragment in the case of the adhP gene derived from *Escherichia coli* (Ligation Liquid AJ), an about 2.0-kb inserted fragment in the case of the adh gene derived from *Pseudomonas putida* (Ligation Liquid AK), or an about 2.1-kb inserted fragment in the case of the adh2 gene derived from *Saccharomyces cerevisiae* (Ligation Liquid AL).

The plasmid comprising the adhP gene derived from *Escherichia coli* was named pCRB15-adhP/EC, the plasmid comprising the adh gene derived from *Pseudomonas putida* was named pCRB15-adh/PP, and the plasmid comprising the adh2 gene derived from *Saccharomyces cerevisiae* was named pCRB15-adh2/SC (FIG. 2).

The above-mentioned plasmid pCRB207-ilvD/CG was cut with use of restriction enzymes KpnI and PstI. After agarose gel electrophoresis, an about 2.9-kb DNA fragment collected from the agarose gel with use of QIAquick Gel Extraction Kit (made by QIAGEN), in which fragment a gapA promoter and the ilvD gene derived from *Corynebacterium glutamicum*, and a terminator sequence were ligated, and the above-mentioned about 5.8-kb plasmid pCRB15-adhP/EC cut with use of KpnI were blunted with use of DNA Blunting Kit (made by Takara Bio, Inc.). The DNA fragments were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation. This was named Ligation Liquid AM.

With use of the Ligation Liquid AM, *Escherichia coli* JM109 was transformed by the calcium chloride method (Journal of Molecular Biology, 53, 159 (1970)) and was applied to LB agar medium (1% of polypeptone, 0.5% of yeast extract, 0.5% of sodium chloride, and 1.5% of agar) containing 25 μg/mL of zeocin.

A growing strain on the culture medium was subjected to liquid culture in the usual manner. Plasmid DNA was extracted from the culture medium and cut with use of a restriction enzyme to confirm the inserted fragment. As a result, in addition to an about 5.8-kb DNA fragment of the plasmid pCRB15-adhP/EC, an about 2.9-kb inserted fragment was confirmed in the case of the ilvD gene derived from *Corynebacterium glutamicum* (Ligation Liquid AM).

The plasmid comprising the adhP gene derived from *Escherichia coli* and the ilvD gene derived from *Corynebacterium glutamicum* was named pCRB15-adhP/EC-ilvD/CG (FIG. 2).

(3) Preparation of Isobutanol Producing Strains

Further, with use of the plasmids pCRB1-ilvB-ilvN-ilvC/CG-ilvD/CG, pCRB208-kivD/LL and pCRB15-adh2/SC, transformation of *Corynebacterium glutamicum* R ldhA mutant (J. Mol. Microbiol. Biotechnol., Vol. 8, 243-254 (2004)) was performed by the electric pulse method (Agric. Biol. Chem., Vol. 54, 443-447 (1990) and Res. Microbiol., Vol. 144, 181-185 (1993)), and the strain was applied to A agar medium containing 5 μg/mL of chloramphenicol, 50 μg/mL of kanamycin, and 25 μg/mL of zeocin. These three kinds of plasmids can coexist in *Corynebacterium glutamicum*.

A growing strain on the culture medium was subjected to liquid culture in the usual manner. Plasmid DNA was extracted from the culture medium and cut with use of restriction enzymes to confirm the inserted fragments. As a result, introduction of the above-prepared plasmids pCRB1-ilvB-ilvN-ilvC/CG-ilvD/CG, pCRB208-kivD/LL, and pCRB15-adh2/SC was confirmed. The obtained strain was named *Corynebacterium glutamicum* IBU1. The outline of gene recombination in this strain is shown in Table 6. *Corynebacterium glutamicum* IBU1 was deposited in Incorporated Administrative Agency National Institute of Technology and Evaluation, NITE Patent Microorganisms Depositary (2-5-8 Kazusakamatari, Kisarazu-shi, Chiba 292-0818 Japan) under Accession Number NITE BP-718 on Mar. 17, 2009.

In a similar manner, with use of the plasmids pCRB1-ilvB-ilvN-ilvC/CG-ilvD/CG, pCRB208-kivD/LL, and pCRB15-adhP/EC, transformation of *Corynebacterium glutamicum* R ldhA mutant (J. Mol. Microbiol. Biotechnol., Vol. 8, 243-254 (2004)) was performed by the electric pulse method (Agric. Biol. Chem., Vol. 54, 443-447 (1990) and Res. Microbiol., Vol. 144, 181-185 (1993)), and the strain was applied to A agar medium containing 5 μg/mL of chloramphenicol, 50 μg/mL of kanamycin, and 25 μg/mL of zeocin. These three kinds of plasmids can coexist in *Corynebacterium glutamicum*.

A growing strain on the culture medium was subjected to liquid culture in the usual manner. Plasmid DNA was extracted from the culture medium and cut with use of restriction enzymes to confirm the inserted fragments. As a result, introduction of the above-prepared plasmids pCRB1-ilvB-ilvN-ilvC/CG-ilvD/CG, pCRB208-kivD/LL, and pCRB15-adhP/EC was confirmed. The obtained strain was named *Corynebacterium glutamicum* IBU2. The outline of gene recombination in this strain is shown in Table 6. *Corynebacterium glutamicum* IBU2 was deposited in Incorporated Administrative Agency National Institute of Technology and Evaluation, NITE Patent Microorganisms Depositary (2-5-8 Kazusakamatari, Kisarazu-shi, Chiba 292-0818 Japan) under Accession Number NITE BP-719 on Mar. 17, 2009.

Further, with use of the plasmids pCRB1-ilvB-ilvN-ilvC/CG-ilvD/CG, pCRB208-kivD/LL and pCRB15-adh/PP, transformation of *Corynebacterium glutamicum* R ldhA mutant (J. Mol. Microbiol. Biotechnol., Vol. 8, 243-254 (2004)) was performed by the electric pulse method (Agric. Biol. Chem., Vol. 54, 443-447 (1990) and Res. Microbiol., Vol. 144, 181-185 (1993)), and the strain was applied to A agar medium containing 5 μg/mL of chloramphenicol, 50 μg/mL of kanamycin, and 25 μg/mL of zeocin. These three kinds of plasmids can coexist in *Corynebacterium glutamicum*.

A growing strain on the culture medium was subjected to liquid culture in the usual manner. Plasmid DNA was extracted from the culture medium and cut with use of restriction enzymes to confirm the inserted fragments. As a result, introduction of the above-prepared plasmids pCRB1-ilvB-ilvN-ilvC/CG-ilvD/CG, pCRB208-kivD/LL, and pCRB15-adh/PP was confirmed. The obtained strain was named *Corynebacterium glutamicum* IBU3. The outline of gene recombination in this strain is shown in Table 6. *Corynebacterium glutamicum* IBU3 was deposited in Incorporated Administrative Agency National Institute of Technology and Evaluation, NITE Patent Microorganisms Depositary (2-5-8 Kazusakamatari, Kisarazu-shi, Chiba 292-0818 Japan) under Accession Number NITE BP-720 on Mar. 17, 2009.

Further, with use of the plasmids pCRB205-alsS/BS-ilvC/CG, pCRB207-kivD, and pCRB15-adhP/EC-ilvD/CG, transformation of *Corynebacterium glutamicum* R ldhA mutant (J. Mol. Microbiol. Biotechnol., Vol. 8, 243-254 (2004)) was performed by the electric pulse method (Agric. Biol. Chem., Vol. 54, 443-447 (1990) and Res. Microbiol., Vol. 144, 181-185 (1993), and the strain was applied to A agar medium containing 5 μg/mL of chloramphenicol, 50 μg/mL of kanamycin, and 25 μg/mL of zeocin. These three kinds of plasmids can coexist in *Corynebacterium glutamicum*.

A growing strain on the culture medium was subjected to liquid culture in the usual manner. Plasmid DNA was extracted from the culture medium and cut with use of restriction enzymes to confirm the inserted fragments. As a result, introduction of the above-prepared plasmids pCRB205-alsS/BS-ilvC/CG, pCRB207-kivD/LL, and pCRB15-adhP/EC-ilvD/CG was confirmed. The obtained strain was named *Corynebacterium glutamicum* IBU4. The outline of gene recombination in this strain is shown in Table 6. *Corynebacterium glutamicum* IBU4 was deposited in Incorporated Administrative Agency National Institute of Technology and Evaluation, NITE Patent Microorganisms Depositary (2-5-8 Kazusakamatari, Kisarazu-shi, Chiba 292-0818 Japan) under Accession Number NITE BP-721 on Mar. 17, 2009.

TABLE 6

Recombination outline of isobutanol-producing strains and comparative strains

| Strain | Introduced genes (gene name/gene origin (gene recombination))* | | | | |
|---|---|---|---|---|---|
| Name | AHAS | AHAIR | DHAD | KDC | ADH |
| IBU1 | ilvB-ilvN/CG | ilvC/CG | ilvD/CG | kivD/LL | adh2/SC |
| IBU2 | ilvB-ilvN/CG | ilvC/CG | ilvD/CG | kivD/LL | adhP/EC |
| IBU3 | ilvB-ilvN/CG | ilvC/CG | ilvD/CG | kivD/LL | adh/PP |
| IBU4 | alsS/BS | ilvC/CG | ilvD/CG | kivD/LL | adhP/EC |

*Abbreviations in the table are defined as follows.
<Abbreviations of original genes>
BS: *Bacillus subtilis*
CG: *Corynebacterium glutamicum* R
EC: *Escherichia coli*
LL: *Lactococcus lactis*
PP: *Pseudomonas putida*
SC: *Saccharomyces cerevisiae*

(4) Preparation of Comparative Isobutanol Producing Strain

With use of the plasmids pCRB1-ilvB-ilvN/EC-ilvC/EC-ilvD/EC, pCRB208-kivD/LL, and pCRB15-adh2/SC, transformation of *Corynebacterium glutamicum* R ldhA mutant (J. Mol. Microbiol. Biotechnol., Vol. 8, 243-254 (2004)) was performed by the electric pulse method (Agric. Biol. Chem., Vol. 54, 443-447 (1990) and Res. Microbiol., Vol. 144, 181-185 (1993)), and the strain was applied to A agar medium containing 5 μg/mL of chloramphenicol, 50 μg/mL of kanamycin, and 25 μg/mL of zeocin. These three kinds of plasmids can coexist in *Corynebacterium glutamicum*.

A growing strain on the culture medium was subjected to liquid culture in the usual manner. Plasmid DNA was extracted from the culture medium and cut with use of restriction enzymes to confirm the inserted fragments. As a result, introduction of the above-prepared plasmids pCRB1-ilvB-ilvN/EC-ilvC/EC-ilvD/EC, pCRB208-kivD/LL, and pCRB15-adh2/SC was confirmed. The obtained strain was named *Corynebacterium glutamicum* IBU5.

Example 4

Experiment of Isobutanol Production with Use of Corynebacterium glutamicum IBU1, IBU2, and IBU3 Under Reducing Conditions The *Corynebacterium glutamicum* IBU1, IBU2, and IBU3 created in Example 3 were separately applied to A agar medium containing 5 μg/mL of chloramphenicol, 50 μg/mL of kanamycin, and 25 μg/mL of zeocin, and left stand in the dark at 28° C. for 20 hours.

An inoculation loop of the *Corynebacterium glutamicum* IBU1, IBU2, and IBU3 each grown on a plate as above was separately inoculated in a test tube containing 10 mL of A liquid medium containing 5 μg/mL of chloramphenicol, 50 μg/mL of kanamycin, and 25 μg/mL of zeocin, and aerobically cultured with shaking at 28° C. for 15 hours.

The *Corynebacterium glutamicum* IBU1, IBU2, and IBU3 each grown in the above conditions were separately inoculated in a 2-L conical flask containing 500 mL of A liquid medium containing 5 μg/mL of chloramphenicol, 50 μg/mL of kanamycin, and 25 μg/mL of zeocin, and aerobically cultured with shaking at 28° C. for 15 hours.

Each kind of the bacterial cells cultured and proliferated as above was collected by centrifugation (5,000×g at 4° C. for 15 minutes). Each kind of the obtained bacterial cells was separately suspended in BT (-urea) liquid medium (0.7% ammonium sulfate, 0.05% potassium dihydrogen phosphate, 0.05% dipotassium hydrogen phosphate, 0.05% magnesium sulfate heptahydrate, 0.0006% iron sulfate heptahydrate, 0.00042% manganese sulfate hydrate, 0.00002% biotin and 0.00002% thiamine hydrochloride) so that the final concentration of the bacterial cell was $OD_{610}=35$. To a 100-mL medium bottle containing 60 mL of the cell suspensions, glucose was added so as to be 8% in concentration, and the reaction to produce isobutanol was allowed to proceed under reducing conditions (the ORP of the reaction medium determined with ORP Electrode made by James Corp. was between −420 mV to −450 mV) in a water bath kept at 33° C. with stirring. During the reaction for isobutanol production, 2.5 N aqueous ammonia was added with use of a pH controller (Type: DT-1023 made by Able Corp.) to avoid the pH of the reaction mixture falling below 7.0. In the reducing conditions as above, none of *Corynebacterium glutamicum* IBU1, IBU2, and IBU3 proliferated.

For quantitative determination of isobutanol, the reaction mixture sampled was centrifuged (15,000×g at 4° C. for 10 minutes), and obtained supernatant was analyzed by gas chromatography. The gas chromatography analysis was performed with use of a gas chromatography (GC-2014, made by Shimadzu) equipped with a capillary column (Stabilwax, 60 m×0.53 mm (ID)×1 μm (ID), made by RESTEK). The analysis was performed under the following conditions: the flow rate of the carrier gas and the split ratio were set to 318 mL/min and 1:20, respectively. The GC oven conditions were as follows: the temperature was first kept at 40° C. for 5 minutes, and then raised from 40° C. to 120° C. at a heating rate of 20° C./min, from 120° C. to 220° C. at a heating rate of 50° C./min, and finally kept at 220° C. for 4 minutes.

As a result, *Corynebacterium glutamicum* IBU1 produced 184 mM of isobutanol 22 hours after the start of the reaction and 251 mM of isobutanol 36 hours after the start under reducing conditions; *Corynebacterium glutamicum* IBU2 produced 252 mM of isobutanol 22 hours after the start of the reaction and 365 mM of isobutanol 36 hours after the start under reducing conditions; and *Corynebacterium glutamicum* IBU3 produced 255 mM of isobutanol 22 hours after the start of the reaction and 370 mM of isobutanol 36 hours after the start under reducing conditions in the respective reaction mixtures. *Corynebacterium glutamicum* IBU1, IBU2, and IBU3 are similar in that the same AHAS-encoding gene, AHAIR-encoding gene, DHAD-encoding gene, and KDC-encoding gene are introduced thereinto. The only difference is that, as an ADH-encoding gene, introduced are an adh2 gene derived from *Saccharomyces cerevisiae* (adh2/SC)

into IBU1, an adhP gene derived from *Escherichia coli* (adhP/EC) into IBU2, and an adh gene derived from *Pseudomonas putida* (adh/PP) into IBU3 (see Table 6), and the ADH activity in *Corynebacterium glutamicum* with isobutyraldehyde as a substrate was adh2/SC<adhP/EC<adh/PP (see Table 4). The difference in the isobutanol productivity can be attributed to the difference in the ADH activity.

Example 5

Experiment of Isobutanol Production with Use of *Corynebacterium Glutamicum* IBU4 Under Reducing Conditions Isobutanol production was evaluated in the same manner as in Example 4 except that *Corynebacterium glutamicum* IBU4 was used.

As a result, *Corynebacterium glutamicum* IBU4 produced 97 mM of isobutanol 22 hours after the start of the reaction and 146 mM of isobutanol 36 hours after the start in the respective reaction mixtures under reducing conditions.

*Corynebacterium glutamicum* IBU2 and IBU4 are similar in that the same AHAIR-encoding gene, DHAD-encoding gene, KDC-encoding gene, and ADH-encoding gene are introduced thereinto. The only difference is that, as an AHAS-encoding gene, introduced are an ilvBN (ilvB-ilvN) gene derived from *Corynebacterium glutamicum* into IBU2, and an alsS gene derived from *Bacillus subtilis* into IBU4 (see Table 6).

This Example is an experimental example showing that, as an AHAS-encoding gene, introduction of an endogenous ilvBN gene derived from *Corynebacterium glutamicum* provides a higher productivity than introduction of an exogenous alsS gene derived from *Bacillus subtilis*.

Comparative Example 1

Experiment of Isobutanol Production with Use of *Corynebacterium glutamicum* IBU5 Under Reducing Conditions Isobutanol production was evaluated in the same manner as in Example 4 except that *Corynebacterium glutamicum* IBU5 was used.

As a result, *Corynebacterium glutamicum* IBU5 produced 72 mM of isobutanol 22 hours after the start of the reaction and 97 mM of isobutanol 36 hours after the start in the respective reaction mixtures under reducing conditions.

*Corynebacterium glutamicum* IBU2 and IBU5 are similar in that the same KDC-encoding gene and ADH-encoding gene are introduced thereinto. The difference is that, as an AHAS-encoding gene, an AHAIR-encoding gene, and a DHAD-encoding gene, introduced are ilvBN, ilvC, and ilvD genes derived from *Corynebacterium glutamicum* into IBU2, and ilvBN, ilvC, and ilvD genes derived from *Escherichia coli* into IBU5. That is, while the ilvBN, ilvC, and ilvD genes introduced into IBU2 are endogenous, all the five genes introduced into IBU5 are exogenous. As a result, IBU2, into which endogenous ilvBN, ilvC, and ilvD genes from *Corynebacterium glutamicum* were introduced, showed a higher productivity compared with IBU5, into which exogenous ilvBN, ilvC, and ilvD genes from *Escherichia coli* were introduced.

Comparative Example 2

Experiment of Isobutanol Production with Use of *Corynebacterium glutamicum* IBU2 Under Aerobic Proliferation Conditions The *Corynebacterium glutamicum* IBU2 created in Example 3 was applied to A agar medium containing 5 µg/mL of chloramphenicol, 50 µg/mL of kanamycin, and 25 µg/mL of zeocin, and left stand in the dark at 28° C. for 20 hours.

An inoculation loop of the *Corynebacterium glutamicum* IBU2 grown on a plate as above was inoculated in a test tube containing 10 mL of A liquid medium containing 5 µg/mL of chloramphenicol, 50 µg/mL of kanamycin, and 25 µg/mL of zeocin, and aerobically cultured with shaking at 28° C. for 15 hours.

The *Corynebacterium glutamicum* IBU2 grown in the above conditions was moved into a 1-L jar fermentor containing 500 mL of A (-urea) liquid medium (350 mM (5.22%) glucose, 0.7% ammonium sulfate, 0.05% potassium dihydrogen phosphate, 0.05% dipotassium hydrogen phosphate, 0.05% magnesium sulfate heptahydrate, 0.2% yeast extract, 0.7% casamino acid, 0.0006% iron sulfate heptahydrate, 0.00042% manganese sulfate hydrate, 0.00002% biotin and 0.00002% thiamine hydrochloride) containing 5 µg/mL of chloramphenicol, 50 µg/mL of kanamycin, and 25 µg/mL of zeocin, and aerobically cultured for proliferation with sterile-air aeration at 0.5 L/min at 1000 rpm at 28° C. for 16 hours. In the culture proliferation, the pH in the jar fermenter was kept at 7.0 with use of 5 N aqueous ammonia solution.

In the aerobic culture proliferation, the reaction mixture was sampled, and quantitative determination of isobutanol was performed in the same manner as in Example 4. The bacterial cell concentration was determined by absorbance measurement at $OD_{610}$.

Figure 3:
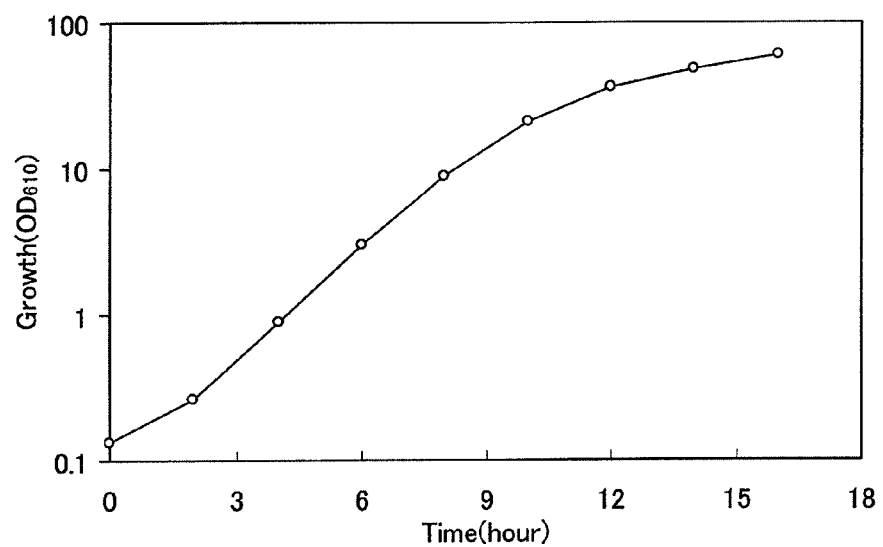
FIG. 3 shows an aerobic proliferation curve of *Corynebacterium glutamicum* IBU2 described in Comparative Example 3.

As a result, *Corynebacterium glutamicum* IBU2 proliferated as shown in FIG. 3. In this case, *Corynebacterium glutamicum* IBU2 produced 0 mM of isobutanol 4 hours after the start of the aerobic culture, 0 mM of isobutanol 10 hours after the start, and 0.3 mM 16 hours after the start. After 16 hours, the concentration of produced isobutanol hardly increased. *Corynebacterium glutamicum* IBU2, which hardly produced isobutanol under aerobic conditions involving proliferation, produced a significant amount of isobutanol under reducing conditions without proliferation (see Example 4).

Comparative Example 3

Experiment of Isobutanol Production with Use of *Corynebacterium* Other than *Corynebacterium glutamicum* Under Reducing Conditions Isobutanol production was evaluated in the same manner as in Example 4 except that, instead of *Corynebacterium glutamicum*, *Corynebacterium capitovis*, *Corynebacterium casei*, *Corynebacterium halotolerans*, and *Corynebacterium terpenotabidum* were used as a host producing isobutanol. As the plasmid to be introduced, pCRB1-ilvB-ilvN-ilvC/CG-ilvD/CG, pCRB208-kivD/LL, and pCRB15-adhP/EC were used as in *Corynebacterium glutamicum* IBU2.

As a result, *Corynebacterium casei* as a host produced 5 mM of isobutanol 22 hours after the start of the reaction and 7 mM of isobutanol 36 hours after the start in the respective reaction mixtures under reducing conditions. However, when *Corynebacterium capitovis, Corynebacterium halotolerans,* and *Corynebacterium terpenotabidum* were used as a host, no significant production of isobutanol could be observed in the respective reaction mixtures.

Consequently, it was clarified that as a host for producing isobutanol, *Corynebacterium glutamicum* is the most excellent in *Corynebacterium.*

Industrial Applicability

The use of the transformant of the present invention enables efficient production of isobutanol from saccharides.
Reference To Deposited Biological Material
*Corynebacterium glutamicum* IBU1 NITE BP-718
*Corynebacterium glutamicum* IBU2 NITE BP-719
*Corynebacterium glutamicum* IBU3 NITE BP-720
*Corynebacterium glutamicum* IBU4 NITE BP-721

The invention claimed is:

1. A transformant which is *Corynebacterium glutamicum* IBU1 (Accession Number: NITE BP-718), *Corynebacterium glutamicum* IBU2 (Accession Number: NITE BP-719), *Corynebacterium glutamicum* IBU3 (Accession Number: NITE BP-720), or *Corynebacterium glutamicum* IBU4 (Accession Number: NITE BP-721).

2. A process for producing isobutanol, which comprises a step of reacting the transformant as defined in claim 1, in a reaction culture medium containing saccharides under reducing conditions, and a step of collecting the resulting isobutanol.

3. The process for producing isobutanol as defined in claim 2, wherein the transformant does not substantially proliferate in the reaction step.

4. The process for producing isobutanol as defined in claim 2, wherein the oxidation-reduction potential of the reaction culture medium under reducing conditions is −100 mV to −500 mV.

* * * * *